US012064309B2

(12) United States Patent
Wucher et al.

(10) Patent No.: US 12,064,309 B2
(45) Date of Patent: *Aug. 20, 2024

(54) ORTHODONTIC TREATMENT USING AN ORTHODONTIC TREATMENT PLAN

(71) Applicant: Ortho Future Technologies (Pty) Ltd, Windhoek (NA)

(72) Inventors: Tim Wucher, Windhoek (NA); Martin Wucher, Windhoek (NA); Alfred Meyer Dippenaar, Windhoek (NA)

(73) Assignee: ORTHO FUTURE TECHNOLOGIES (PTY) LTD, Windhoek (NA)

(*) Notice: Subject to any disclaimer, the term of this patent is extended or adjusted under 35 U.S.C. 154(b) by 212 days.

This patent is subject to a terminal disclaimer.

(21) Appl. No.: 17/587,920

(22) Filed: Jan. 28, 2022

(65) Prior Publication Data

US 2022/0265391 A1 Aug. 25, 2022

Related U.S. Application Data

(63) Continuation of application No. 17/143,907, filed on Jan. 7, 2021, now Pat. No. 11,278,376.

(51) Int. Cl.
*A61C 7/00* (2006.01)
(52) U.S. Cl.
CPC .................................. *A61C 7/002* (2013.01)
(58) Field of Classification Search
CPC .................................. A61C 7/002; A61C 7/02
(Continued)

(56) References Cited

U.S. PATENT DOCUMENTS

| 3,885,310 A | 5/1975 | Northcutt |
| 6,832,912 B2 | 12/2004 | Mao |

(Continued)

FOREIGN PATENT DOCUMENTS

| CN | 111046451 A | 4/2020 |
| EP | 2791642 B1 | 6/2019 |

(Continued)

OTHER PUBLICATIONS

Konermann, A, et al., "In vivo determination of tooth mobility after fixed orthodontic appliance therapy with a novel intraoral measurement device," Clinical Oral Investigations, 2017, vol. 21(4), pp. 1283-1289.

(Continued)

*Primary Examiner* — Nicholas D Lucchesi
(74) *Attorney, Agent, or Firm* — Womble Bond Dickinson (US) LLP

(57) ABSTRACT

A method for obtaining an orthodontic treatment plan is provided. The method comprises obtaining a treatment plan for treatment of a tooth of a patient, the treatment plan including two or more stage force values, wherein each of the two or more stage force values is based on a target orthodontic force value that is based on one or more determinate points of periodontal ligament (PDL) behavior data. For each of the two or more stage force values, the method includes determining configuration parameters for configuring an orthodontic appliance to apply the stage force value to a tooth of the patient; and, using the configuration parameters to manufacture an orthodontic appliance configured to apply the stage force value.

16 Claims, 20 Drawing Sheets

(58) Field of Classification Search
USPC .......................................................... 433/18
See application file for complete search history.

(56) References Cited

U.S. PATENT DOCUMENTS

| | | | |
|---|---|---|---|
| 7,029,276 | B2 | 4/2006 | Mao |
| 7,942,672 | B2 | 5/2011 | Kuo |
| 9,113,700 | B2 | 8/2015 | Bates |
| 9,125,588 | B2 | 9/2015 | Parks |
| 9,433,478 | B2 | 9/2016 | Wucher |
| 9,788,917 | B2 | 10/2017 | Mah |
| 10,159,542 | B2 | 12/2018 | Pesach |
| 10,426,574 | B2 | 1/2019 | Raby et al. |
| 10,307,222 | B2 | 6/2019 | Morton et al. |
| 10,383,705 | B2 | 8/2019 | Shanjani |
| 10,398,386 | B2 | 9/2019 | Grady et al. |
| 10,426,575 | B1 | 10/2019 | Raslambekov |
| 10,603,137 | B2 | 3/2020 | Alauddin et al. |
| 10,653,502 | B2 | 5/2020 | Kuo |
| 10,717,208 | B1* | 7/2020 | Raslambekov ......... B29C 51/08 |
| 10,970,436 | B2 | 4/2021 | Zhou |
| 10,993,782 | B1 | 5/2021 | Raslambekov |
| 10,998,101 | B1 | 5/2021 | Tran |
| 11,766,312 | B1* | 9/2023 | Raslambekov ......... G06T 17/20 |
| | | | 433/24 |
| 2003/0059736 | A1 | 3/2003 | Lai |
| 2006/0223023 | A1 | 10/2006 | Lai |
| 2006/0275736 | A1 | 12/2006 | Wen |
| 2008/0227046 | A1 | 9/2008 | Lowe |
| 2009/0042159 | A1 | 2/2009 | Yamamoto |
| 2010/0280798 | A1 | 11/2010 | Pattijn |
| 2011/0136070 | A1 | 6/2011 | Rubin |
| 2013/0273490 | A1 | 10/2013 | Way |
| 2015/0173856 | A1 | 6/2015 | Lowe |
| 2015/0230885 | A1 | 8/2015 | Wucher |
| 2015/0265375 | A1 | 9/2015 | Yamamoto |
| 2016/0038092 | A1 | 2/2016 | Golay |
| 2016/0199216 | A1 | 7/2016 | Cam |
| 2016/0252439 | A1 | 9/2016 | Earthman et al. |
| 2016/0287354 | A1 | 10/2016 | Viecilli |
| 2017/0224444 | A1 | 8/2017 | Viecilli |
| 2017/0273760 | A1* | 9/2017 | Morton ................. A61C 7/002 |
| 2018/0158544 | A1 | 6/2018 | Trosien et al. |
| 2019/0231479 | A1 | 8/2019 | Knopp et al. |
| 2020/0046461 | A1 | 2/2020 | Shanjani et al. |
| 2020/0093571 | A1 | 3/2020 | Shanjani et al. |
| 2020/0214817 | A1 | 7/2020 | Shanjani et al. |
| 2020/0237289 | A1 | 7/2020 | Hanssen |
| 2020/0289239 | A1 | 9/2020 | Raby |
| 2020/0315743 | A1 | 10/2020 | Raslambekov |
| 2020/0337630 | A1 | 10/2020 | Earthman et al. |
| 2021/0007832 | A1 | 1/2021 | Roein Peikar |
| 2021/0022832 | A1 | 1/2021 | Yancey |
| 2021/0093421 | A1 | 4/2021 | Michaeli |

FOREIGN PATENT DOCUMENTS

| | | |
|---|---|---|
| JP | 2018504191 A | 2/2018 |
| WO | 2006115841 A2 | 11/2006 |
| WO | 2013121316 A1 | 8/2013 |
| WO | 2020/048960 A1 | 3/2020 |

OTHER PUBLICATIONS

Ren Y, Maltha JC, Van 't Hof M, Kuijpers-Jagtman AM. Optimum force magnitude for orthodontic tooth movement: a mathematic model. Am. J. Orthod. Dentofac. Orthop. 2004;125:71-7.

Oppenheim A. Human tissue response to orthodontic intervention of short and long duration. Am. J. Orthod. Oral Surg. 1942;28:263-301.

Reitan K. Some factors determining the evaluation of forces in orthodontics. Am. J. Orthod. 1957;43:32-45.

Quinn RS, Yoshikawa Dk. A reassessment of force magnitude in orthodontics. Am. J. Orthod. 1985;88:252-60.

Bosshardt DD, Bergomi M, Vaglio G, Wiskott A. Regional structural characteristics of bovine periodontal ligament samples and their suitability for biomechanical tests. J. Anat. 2008;212:319-29.

Cattaneo PM, Dalstra M, Melsen B. The finite element method: a tool to study orthodontic tooth movement. J. Dent. Res. 2005;84:428-33.

Graber TM. Extraoral force—Facts and fallacies. Am. J. Orthod. 1954;41:490-505.

Reitan K. Clinical and histologic observations on tooth movement during and after orthodontic treatment. Am. J. Orthod. 1967;53:721-45.

Wasaki LR, Haack JE, Nickel JC, Morton J. Human tooth movement in response to continuous stress of low magnitude. Am. J. Orthod. Dentofac. Orthop. 2000;117:175-83.

Owman-Moll P, Kurol J, Lundgren D. Effects of a doubled orthodontic force magnitude on tooth movement and root resorptions. An inter-individual study in adolescents. Eur. J. Orthod. 1996;18:141-50.

Van Leeuwen EJ, Kuijpers-Jagtman AM, Von den Hoff JW, Wagener FADTG, Maltha JC. Rate of orthodontic tooth movement after changing the force magnitude: An experimental study in beagle dogs. Orthod. Craniofacial Res. 2010;13:238-45.

Pilon JJ, Kuijpers-Jagtman A, Maltha JC. Magnitude of orthodontic forces and rate of bodily tooth movement. An experimental study. Am. J. Orthod. Dentofac. Orthop. 1996;110:16-23.

Gibson JM, King GJ, Keeling SD. Long-term orthodontic tooth movement response to short-term force in the rat. Angle Orthod. 1992;62:211-5.

Ren Y, Maltha JC, Stokroos I, Liem RSB, Kuijpers-Jagtman AM. Effect of duration of force application on blood vessels in young and adult rats. Am. J. Orthod. Dentofac. Orthop. 2008;133:752-7.

Darendeliler MA, Zea A, Shen G, Zoellner H. Effects of pulsed electromagnetic field vibration on tooth movement induced by magnetic and mechanical forces: a preliminary study. Aust. Dent. J. 2007;52:282-7.

Peptan AI, Lopez A, Kopher R a, Mao JJ. Responses of intramembranous bone and sutures upon in vivo cyclic tensile and compressive loading. Bone 2008;42:432-8.

Nishimura M, Chiba M, Ohashi T, et al. Periodontal tissue activation by vibration: intermittent stimulation by resonance vibration accelerates experimental tooth movement in rats. Am. J. Orthod. Dentofac. Orthop. 2008;133:572-83.

Rubin J, Rubin C, Jacobs CR. Molecular pathways mediating mechanical signaling in bone. Gene 2006;367:1-16.

Von Böhl M, Kuijpers-Jagtman AM. Hyalinization during orthodontic tooth movement: a systematic review on tissue reactions. Eur. J. Orthod. 2009;31:30-6.

Ren Y, Maltha JC, Kuijpers-Jagtman AM. Optimum force magnitude for orthodontic tooth movement: a systematic literature review. Angle Orthod. 2003;73:86-92.

Van Leeuwen EJ, Maltha JC, Kuijpers-Jagtman AM. Tooth movement with light continuous and discontinuous forces in beagle dogs. Eur. J. Oral Sci. 1999;107:468-74.

Castellini P, Scalise L, Tomasini EP. Teeth mobility measurement: a laser vibrometry approach. J. Clin. Laser Med. Surg. 1998;16:269-72.

Yoshida N, Koga Y, Kobayashi K, Yamada Y, Yoneda T. A new method for qualitative and quantitative evaluation of tooth displacement under the application of orthodontic forces using magnetic sensors. Med. Eng. Phys. 2000;22:293-300.

Ziegler A, Keilig L, Kawarizadeh A, Jager A, Bourauel C. Numerical simulation of the biomechanical behaviour of multi-rooted teeth. Eur. J. Orthod. 2005;27:333-9.

Sanctuary CS, Wiskott HWA, Justiz J, Botsis J, Belser UC. In vitro time-dependent response of periodontal ligament to mechanical loading. J. Appl. Physiol. 2005;99:2369-78.

Papadopoulou K, Keilig L, Eliades T, Krause R, Jäger A, Bourauel C. The time-dependent biomechanical behaviour of the periodontal ligament—An in vitro experimental study in minipig mandibular two-rooted premolars. Eur. J. Orthod. 2014;36:9-15.

Jing Y, Han XL, Cheng BH, Bai D. Three-dimensional FEM analysis of stress distribution in dynamic maxillary canine movement. Chinese Sci. Bull. 2013;58:2454-9.

(56) References Cited

OTHER PUBLICATIONS

Papadopoulou K, Hasan I, Keilig L, et al. Biomechanical time dependency of the periodontal ligament: A combined experimental and numerical approach. Eur. J. Orthod. 2013;35:811-8.

Minch L. Material properties of periodontal ligaments. Postepy Hig. Med. Dosw. 2013;67:1261-4.

Wakabayashi N, Ona M, Suzuki T, Igarashi Y. Nonlinear finite element analyses: advances and challenges in dental applications. J. Dent. 2008;36:463-71.

Mühlemann HR. Tooth mobility: a review of clinical aspects and research findings. J. Periodontol. 1967;38: Suppl:686-713.

Von Böhl M, Maltha JC, Von Den Hoff H, Kuijpers-Jagtman AM. Changes in the periodontal ligament after experimental tooth movement using high and low continuous forces in beagle dogs. Angle Orthod. 2004;74:16-25.

Natali AN, Pavan PG, Scarpa C. Numerical analysis of tooth mobility: Formulation of a non-linear constitutive law for the periodontal ligament. Dent. Mater. 2004;20:623-9.

Melsen B, Cattaneo PM, Dalstra M, Kraft DC. The Importance of Force Levels in Relation to Tooth Movement. Semin. Orthod. 2007;13:220-33.

Kojima Y, Fukui H. Numerical simulations of canine retraction with T-loop springs based on the updated moment-to-force ratio. Eur. J. Orthod. 2012;34:10-8.

Cattaneo PM, Dalstra M, Melsen B. Moment-to-force ratio, center of rotation, and force level: a finite element study predicting their interdependency for simulated orthodontic loading regimens. Am. J. Orthod. Dentofacial Orthop. 2008;133:681-9.

Kawarizadeh A, Bourauel C, Jager A. Experimental and numerical determination of initial tooth mobility and material properties of the periodontal ligament in rat molar specimens. Eur. J. Orthod. 2003;25:569-78.

Wu JL, Liu YF, Peng W, Dong HY, Zhang JX. A biomechanical case study on the optimal orthodontic force on the maxillary canine tooth based on finite element analysis. Journal of Zhejiang University. Science. B. Jul. 2018;19 (7):535-546.

Jiang, J., Huang, Z., Ma, X., Zhang, Y., Han, Y. and Liu, Y., 2018. Orthodontic process safety evaluation based on periodontal ligament capillary pressure and Ogden model. Journal of Mechanics in Medicine and Biology, 18(08), p. 1840033.

Zhipeng Liao, Junning Chen, Wei Li, M. Ali Darendeliler, Michael Swain, Qing Li, Biomechanical investigation into the role of the periodontal ligament in optimising orthodontic force: a finite element case study, Archives of Oral Biology, vol. 66, 2016, p. 98-107.

Drolshagen, M. et al., "Development of a novel intraoral measurement device to determine the biomechanical characteristics of the human periodontal ligament," Journal of Biomechanics, 2011, vol. 44(11), pp. 2136-2143.

Gollner, M, et al., "Noncontact intraoral measurement of force-related tooth mobility," Clinical Oral Investigations, 2010, vol. 14(5), pp. 551-557.

Keilig, L., et al., "Increased tooth mobility after fixed orthodontic appliance treatment can be selectively utilized for case refinement via positioner therapy—a pilot study," BMC Oral Health, 2020, vol. 20(114), pp. 1-8.

\* cited by examiner

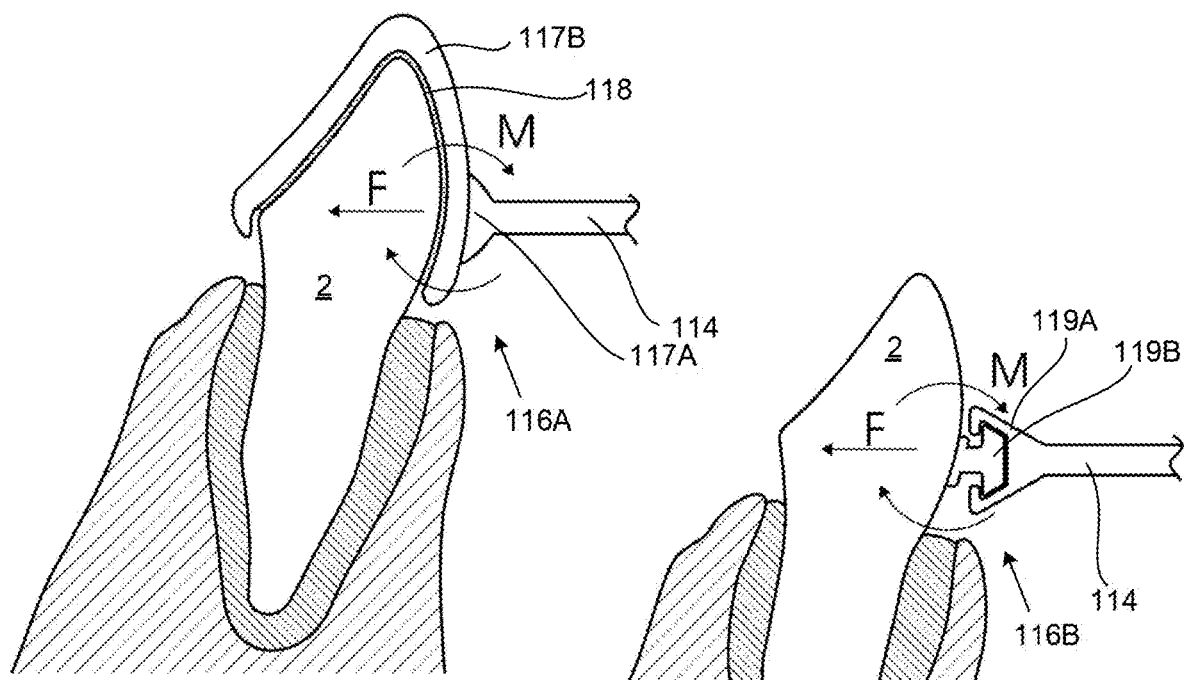
FIG. 2A
FIG. 2B
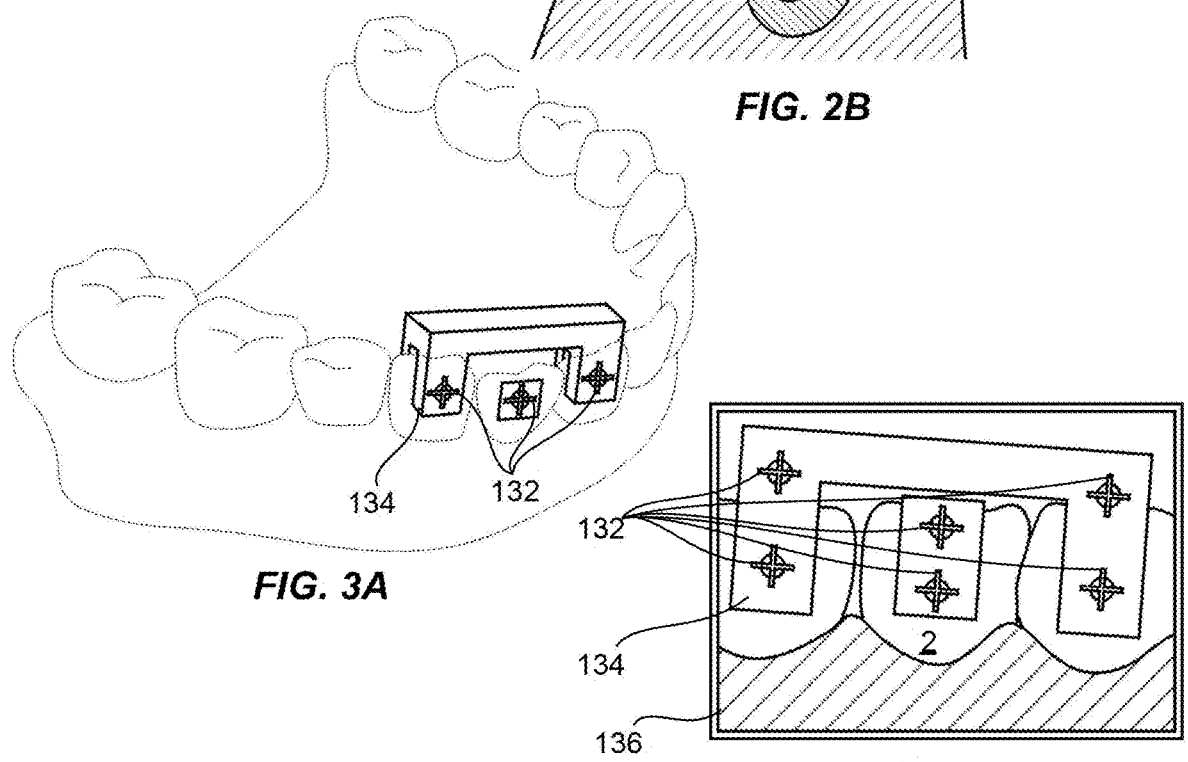
FIG. 3A
FIG. 3B

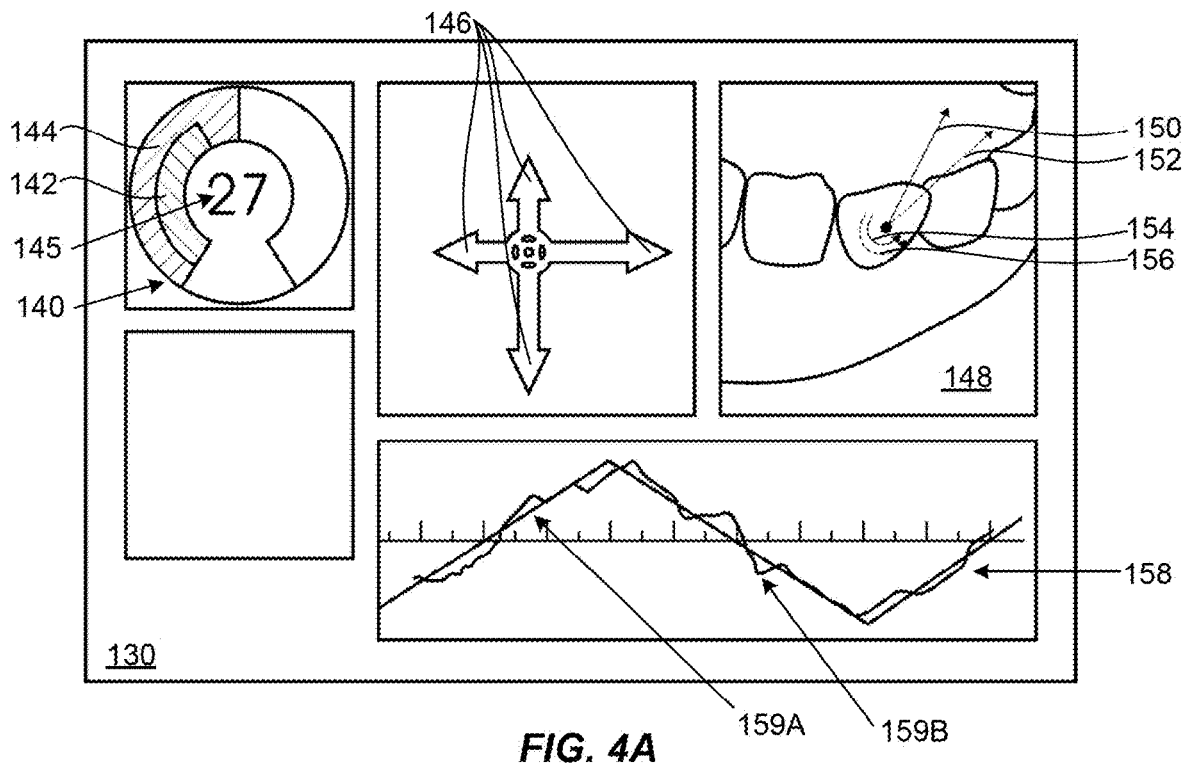
FIG. 4A
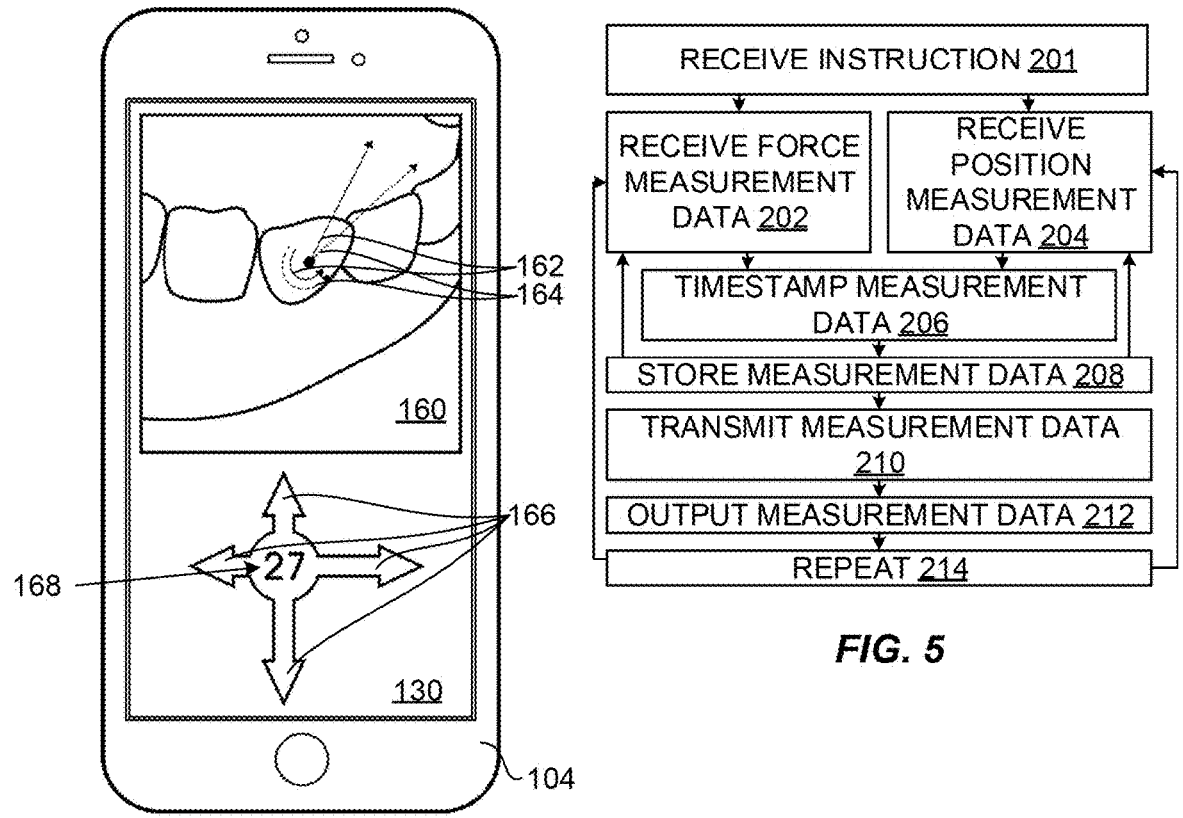
FIG. 4B
FIG. 5

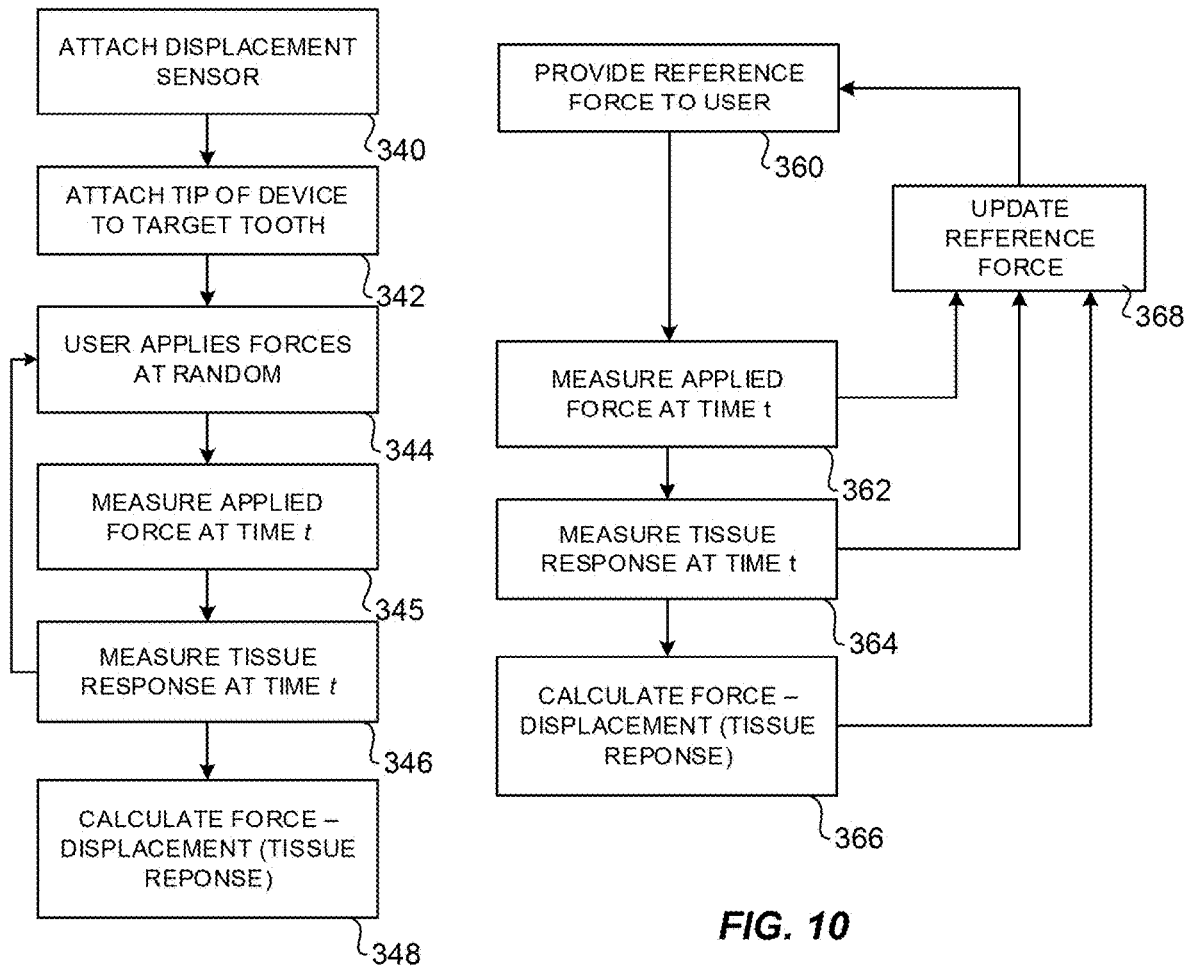
FIG. 9
FIG. 10
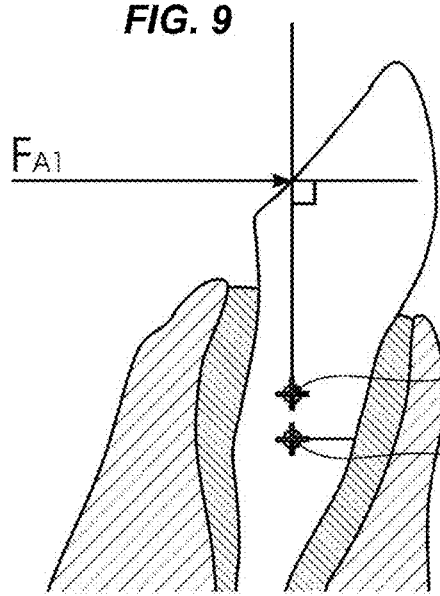
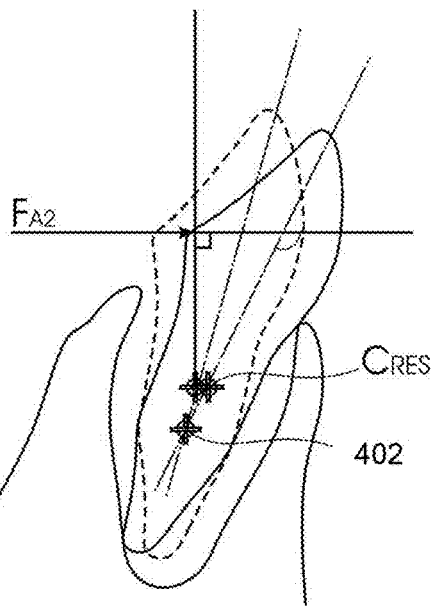
FIG. 12

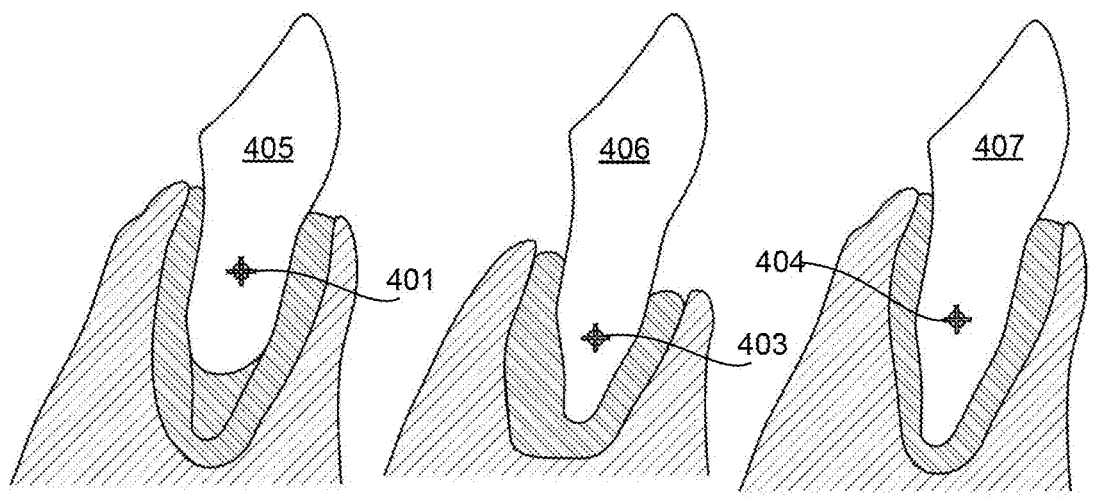
FIG. 13
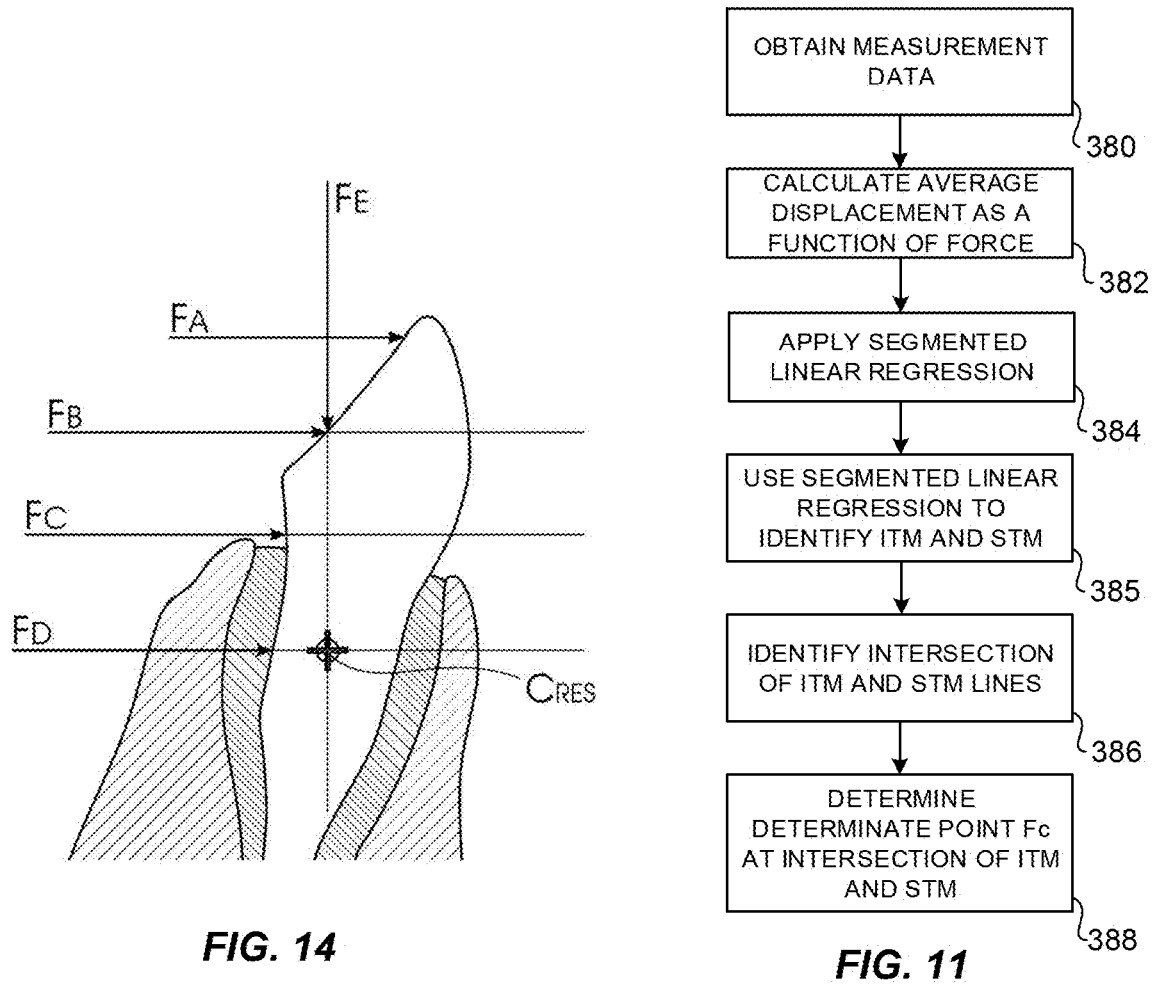
FIG. 14
FIG. 11

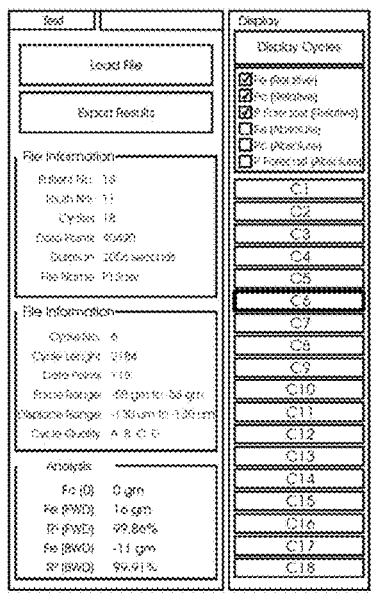
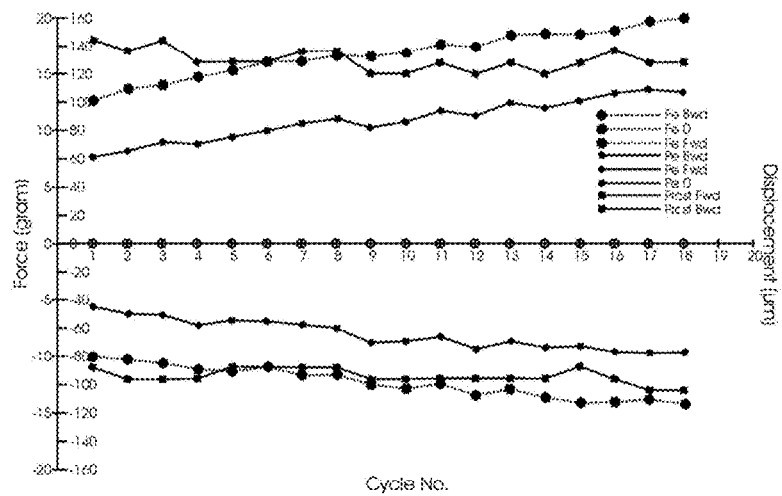

FIG. 28

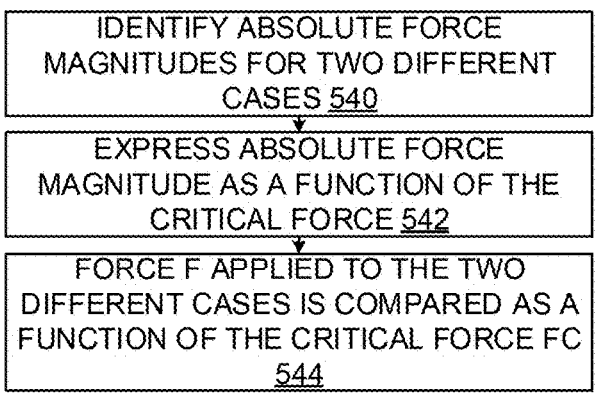

IDENTIFY ABSOLUTE FORCE MAGNITUDES FOR TWO DIFFERENT CASES 540

EXPRESS ABSOLUTE FORCE MAGNITUDE AS A FUNCTION OF THE CRITICAL FORCE 542

FORCE F APPLIED TO THE TWO DIFFERENT CASES IS COMPARED AS A FUNCTION OF THE CRITICAL FORCE FC 544

FIG. 34

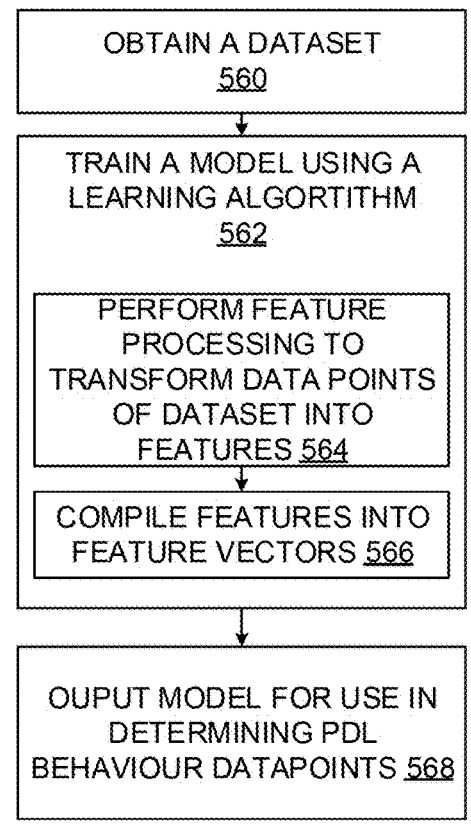

OBTAIN A DATASET 560

TRAIN A MODEL USING A LEARNING ALGORITITHM 562

PERFORM FEATURE PROCESSING TO TRANSFORM DATA POINTS OF DATASET INTO FEATURES 564

COMPILE FEATURES INTO FEATURE VECTORS 566

OUPUT MODEL FOR USE IN DETERMINING PDL BEHAVIOUR DATAPOINTS 568

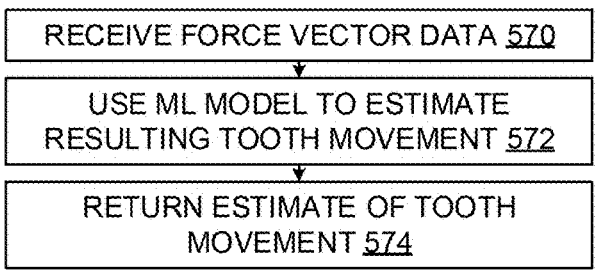

RECEIVE FORCE VECTOR DATA 570

USE ML MODEL TO ESTIMATE RESULTING TOOTH MOVEMENT 572

RETURN ESTIMATE OF TOOTH MOVEMENT 574

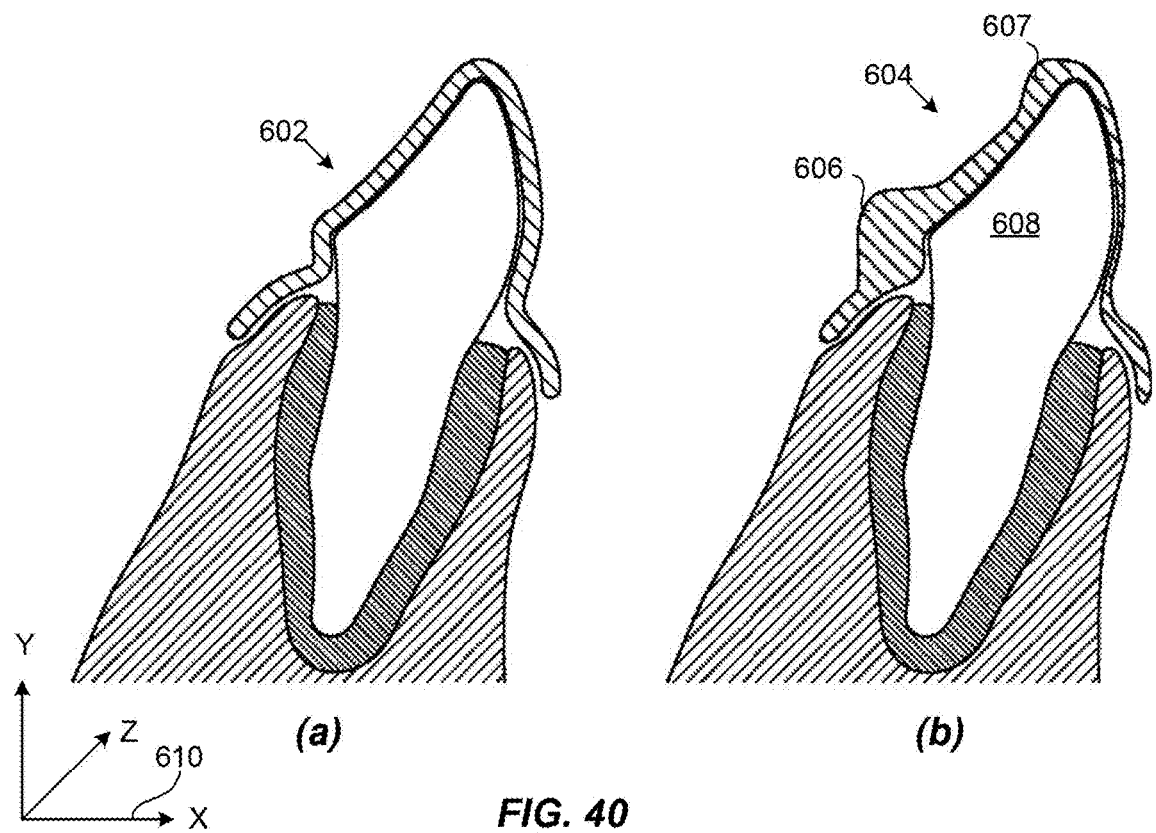
FIG. 40
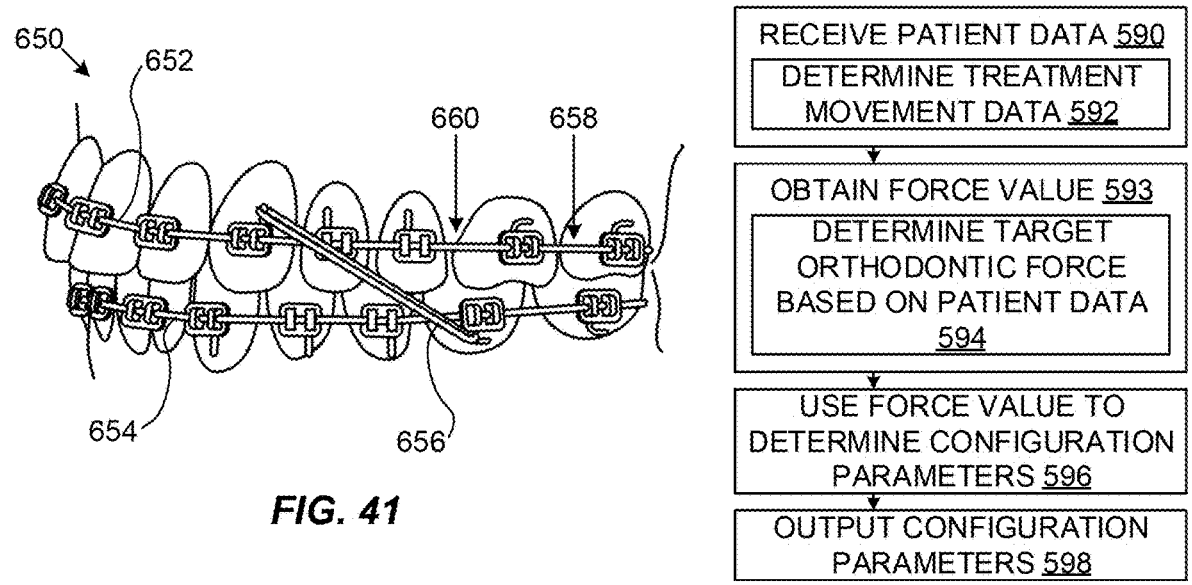
FIG. 41
FIG. 39

ORTHODONTIC TREATMENT USING AN ORTHODONTIC TREATMENT PLAN

CROSS-REFERENCE TO RELATED APPLICATIONS

This is a continuation of U.S. patent application Ser. No. 17/143,907, filed on 7 Jan. 2021, the entire contents of which is incorporated herein by reference in its entirety.

FIELD OF THE INVENTION

This invention relates to methods for orthodontic treatment using orthodontic treatment plans.

BACKGROUND TO THE INVENTION

Orthodontics is the branch of dentistry that deals with the prevention or correction of irregularities of the teeth and jaws. These irregularities may affect the oral health, as well as possibly the physical, aesthetic and/or mental wellbeing of affected individuals.

Tooth positioning and orofacial bone structures can be altered using manual, mechanical systems, generally consisting of a combination of, for example, wires, brackets, bands, chains, springs and elastics, a system commonly referred to as "dental braces" or simply "braces". Similarly, orthodontic treatment and repositioning of tooth and bone structures can be achieved using one or more aligners, retainers, or a combination thereof. Braces or aligners are commonly used to generate, transmit and maintain forces, force vectors and moments to individual teeth or between teeth, activating various biomechanical processes within the affected tissues to facilitate tooth movement.

It is generally accepted that a force of zero magnitude will not induce any tooth movement, whereas a force of excessive magnitude might damage cells surrounding the tooth and may also cause root resorption and excessive patient discomfort. This gives rise to the concept that an "optimal force" or "optimal orthodontic force" exists, between a zero force and a force of excessive magnitude, which would be capable of inducing the maximum rate of tooth movement without causing any tissue damage, root resorption, as little as possible patient discomfort, and a minimum level of additional, adverse side-effects.

Conventional orthodontic systems have a number of shortcomings with regard to this optimal orthodontic force. Firstly, the majority of orthodontic systems rely purely on mechanical components, which allow for little or no control once put in place. The placement of the mechanical components by the practitioner largely determines the forces exerted on the teeth and virtually no controlled changes can be made thereto without manually changing the configuration of the mechanical components. Furthermore, many of the components used, which as stated above include, amongst others, springs, wires and elastic bands, do not accurately generate a constant desired force over a longer period of time or over a specified distance, largely due to the physical characteristics of these components. This makes it improbable that the forces transmitted to the teeth are representative of the optimal force for any continuous period of time. The result of other than optimal forces being applied to the orofacial structures can induce the problems mentioned above.

Conventionally, the ability to control the forces transmitted to the teeth by an orthodontic appliance was one of the biggest challenges. The availability of new technologies and advanced manufacturing techniques has greatly improved the ability to control such parameters. However, this gives rise to the next and perhaps even more critical question in orthodontics—the need to accurately determine the optimal force that would result in the most effective treatment. For example, Wu et al., have conducted "A biomechanical case study on the optimal orthodontic force on the maxillary canine tooth based on finite element analysis". Liao et al. present "Biomechanical investigation into the role of the periodontal ligament in optimizing orthodontic force: a finite element case study". Such an optimal force is highly patient and also tooth specific and the ability to accurately determine such an optimal force is key to provide customized and patient specific orthodontic treatment. To the applicant's knowledge, however, it has not yet been possible to quantitatively describe such an optimal force. Finite element method-based analysis, for example, requires careful definition of input parameters which, for the case of the PDL complex, should preferably include parameters detailing blood pressure, fibrous tissue structure and bone properties and structures, which naturally vary considerably from one person to the next. Without proper definition of these parameters, the models cannot be used to determine an optimal orthodontic force that is patient- and tooth-specific.

Based on the data from a number of studies of which the applicant is aware, it was concluded that the reviewed experimental results were negatively affected by, amongst others, the inability to accurately calculate stresses in the periodontal ligament of a given tooth, the inability to control the type of tooth movement, the different phases of tooth movement during an applied force and large inter-individual variations or even variations within individuals. As a result, no exact ideal force magnitude could be recommended.

It has also been found that large individual variations exist for the mean rate of tooth movement achieved under application of the same forces. A possible explanation that has been proposed for this phenomenon is that each individual could have his or her own optimal force that would produce the maximum rate of tooth movement.

Generally, the view has been adopted that the movement of teeth is a result of externally applied mechanical stimuli and the subsequent biological reactions that take place within the periodontium. Inherent to the mechanical stimuli are various parameters including the force magnitude, direction, point of application, frequency of application and duration of application. Still further parameters could play an important role when non-static forces are considered such as the force profile, oscillatory frequency and oscillatory amplitude. The above parameters in combination with the anatomical and physiological properties inherent to the affected tooth/teeth lead to yet further factors affecting tooth movement. A certain mechanical stimulus applied to a specific case will lead to cellular strains, shear stresses and pressure changes within the affected tissues. Each of these could further affect the resulting tooth movement thereby emphasizing the importance of the externally applied stimulus.

There is accordingly scope for improvement.

In the remainder of this specification the terms "optimal orthodontic force" should be interpreted to be such an optimal force when applied in an orthodontic environment. The term "optimal force" should in turn be interpreted to have a corresponding meaning but capable of being applied in any reconstructive or corrective surgery where relative bone or tissue movement is achieved by means of the application of a mechanical force or moment over a period of time. In addition, the terms "force" and "stimulus" are used interchangeably and should be interpreted broadly to include any combination of forces and moments or either individually.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with an aspect of the invention there is provided a method comprising: obtaining a treatment plan for treatment of a tooth of a patient, the treatment plan including two or more stage force values, wherein each of the two or more stage force values is based on a target orthodontic force value that is based on one or more determinate points of periodontal ligament (PDL) behavior data; for each of the two or more stage force values: determining configuration parameters for configuring an orthodontic appliance to apply the stage force value to a tooth of the patient; and, using the configuration parameters to manufacture an orthodontic appliance configured to apply the stage force value.

Each of the two or more stage force values may be different. The target orthodontic force value may take into account time-dependent changes in the one or more determinate points. The one or more determinate points may change throughout a duration of orthodontic tooth movement. The target orthodontic force is specific to the patient, tooth and stage of treatment regimen.

The method may include determining the target orthodontic force by inputting the one or more determinate points into an algorithm that determines the target orthodontic force as a function of the one or more determinate points. Further inputs to the algorithm may include data points relating to one or more of time, magnitude, patient characteristic and patient treatment components. The algorithm may be optimized by iteratively updating the algorithm to optimize feedback data such that the target orthodontic force is an optimal orthodontic force. The feedback data may include one or more of: patient feedback data points and treatment feedback data points. The feedback data may be obtained during use or testing of an orthodontic appliance configured to apply a target orthodontic force.

The PDL behavior data may be associated with patient data including data points relating to time in treatment journey. The PDL behavior data may include or be based on force measurement data points and corresponding displacement measurement data points having been measured in-vivo while applying a force to a particular tooth of a human or animal subject. The PDL behavior data may include a PDL behavior model, and wherein determining the target orthodontic force value includes using the PDL behavior model to determine one or more determinate points of the PDL behavior data. The PDL behavior model may be trained using measured PDL behavior data.

An orthodontic appliance may be manufactured by the method.

In accordance with another aspect of the invention there is provided a set of orthodontic appliances manufactured by the method, wherein each orthodontic appliance in the set of orthodontic appliances may be configured to apply a different stage force value.

In accordance with a further aspect of the invention there is provided a method comprising: receiving patient data including patient treatment data and patient characteristic data, the patient treatment data at least including one or both of a tooth type indicator and a tooth position indicator associated with a tooth of a patient to be treated and a treatment movement value which describes required tooth movement to effect treatment of the tooth; determining one or more stage movement values and corresponding stage force values, wherein each stage force value is based on a target orthodontic force value that is based on one or more determinate points of periodontal ligament (PDL) behavior data associated with at least a subset of the patient data, wherein the PDL behavior data includes or is based on force measurement data points and corresponding displacement measurement data points having been measured in-vivo while applying a force to a particular tooth of a human or animal subject, wherein the sum of the one or more stage movement values approximates the treatment movement value; and, outputting the one or more stage movement values and corresponding stage force values as a treatment plan for treatment of the tooth.

Determining one or more stage movement values and corresponding stage force values may include: determining a target orthodontic force value based on one or more determinate points of PDL behavior data associated with at least a subset of the patient data, wherein the PDL behavior data includes or is based on force measurement data points and corresponding displacement measurement data points having been measured in-vivo while applying a force to a particular tooth of a human or animal subject; using the target orthodontic force value to determine a corresponding stage movement value; comparing the corresponding stage movement value to the treatment movement value; and, if the corresponding stage movement value is less than the treatment movement value, determining, for a next treatment stage, a next target orthodontic force value and a corresponding next stage movement value until the sum of stage movement values approximates the treatment movement value.

Determining one or more stage movement values and corresponding stage force values may include: initializing a stage movement value being equal to the treatment movement value; using the stage movement value to determine a corresponding stage force value based on PDL behavior data associated with at least a subset of the patient data, wherein the PDL behavior data includes or is based on force measurement data points and corresponding displacement measurement data points having been measured in-vivo while applying a force to a particular tooth of a human or animal subject; comparing the corresponding stage force value to a target orthodontic force value based on one or more determinate points of the PDL behavior data; if the corresponding stage force value exceeds the target orthodontic force value, successively defining a new stage movement value which is less than the previous stage movement value and determining a new corresponding stage force value based on the PDL behavior data until the corresponding stage force value approximates the target orthodontic force value.

The method may include storing the stage movement value that corresponds to the stage force value that approximates the target orthodontic force value for use in a treatment plan. The method may include determining a number of treatment stages by dividing the treatment movement value by the stage movement value so as to determine the number of stages required to effect treatment of the tooth by applying the target orthodontic force value for each stage.

Each of: the treatment movement value, stage movement value, stage force value and target orthodontic force value may include components for each of six degrees of freedom. Each of: the treatment movement value, stage movement value, stage force value and target orthodontic force value may be time dependent.

Receiving patient data may include determining the treatment movement value for the patient. The method may be conducted for each tooth to be treated such that a case-, tooth- and patient-specific stage movement value and corresponding stage force value are determined for each tooth to be treated.

The method may include determining the target orthodontic force value. The PDL behavior data may include a PDL behavior model, and determining the target orthodontic force value may include: using the PDL behavior model to determine one or more determinate points of the PDL behavior data; and, inputting the one or more determinate points into an algorithm that determines the target orthodontic force as a function of the one or more determinate points. The method may include determining the target orthodontic force value each time a new stage movement value is defined.

Further inputs to the algorithm may include data points relating to one or more of time, magnitude, patient characteristic and patient treatment components.

The PDL behavior model may be trained using measured PDL behavior data. The measured PDL behavior data may include force measurement data points and corresponding displacement measurement data points having been measured in-vivo while applying a force to a tooth of a human or animal subject.

The algorithm may be optimized by iteratively updating the algorithm to optimize feedback data such that the target orthodontic force is an optimal orthodontic force. The feedback data may include one or more of: test rig feedback data points, patient feedback data points and treatment feedback data points. The feedback data may be obtained during use or testing of an orthodontic appliance configured to apply a target orthodontic force.

In accordance with another aspect of the invention there is provided a system comprising: a processor and a memory configured to provide computer program instructions to the processor to execute functions of modules; a patient data receiving module for receiving patient data including patient treatment data and patient characteristic data, the patient treatment data at least including one or both of a tooth type indicator and a tooth position indicator associated with a tooth of a patient to be treated and a treatment movement value which describes required tooth movement to effect treatment of the tooth; a stage value determining module for determining one or more stage movement values and corresponding stage force values, wherein each stage force value is based on a target orthodontic force value that is based on one or more determinate points of periodontal ligament (PDL) behavior data associated with at least a subset of the patient data, wherein the PDL behavior data includes or is based on force measurement data points and corresponding displacement measurement data points having been measured in-vivo while applying a force to a particular tooth of a human or animal subject, wherein the sum of the one or more stage movement values approximates the treatment movement value; and, a stage value output module for outputting the one or more stage movement values and corresponding stage force values as a treatment plan for treatment of the tooth.

In accordance with another aspect of the invention there is provided a computer program product comprising a non-transitory computer-readable medium having stored computer-readable program code for performing the steps of: receiving patient data including patient treatment data and patient characteristic data, the patient treatment data at least including one or both of a tooth type indicator and a tooth position indicator associated with a tooth of a patient to be treated and a treatment movement value which describes required tooth movement to effect treatment of the tooth; determining one or more stage movement values and corresponding stage force values, wherein each stage force value is based on a target orthodontic force value that is based on one or more determinate points of periodontal ligament (PDL) behavior data associated with at least a subset of the patient data, wherein the PDL behavior data includes or is based on force measurement data points and corresponding displacement measurement data points having been measured in-vivo while applying a force to a particular tooth of a human or animal subject, wherein the sum of the one or more stage movement values approximates the treatment movement value; and, outputting the one or more stage movement values and corresponding stage force values as a treatment plan for treatment of the tooth.

Further features provide for the computer-readable medium to be a non-transitory computer-readable medium and for the computer-readable program code to be executable by a processing circuit.

Embodiments of the invention will now be described, by way of example only, with reference to the accompanying drawings.

BRIEF DESCRIPTION OF THE DRAWINGS

In the drawings:

FIG. 2A is a schematic diagram which illustrates a first example embodiment of an attachment mechanism according to aspects of the present disclosure;

FIG. 2B is a schematic diagram which illustrates a second example embodiment of an attachment mechanism according to aspects of the present disclosure;

FIG. 3A is a schematic diagram which illustrates a reference jig including target points for cooperation with a position measurement module according to aspects of the present disclosure;

FIG. 3B is a schematic diagram which illustrates a field of view of a camera of a position measurement module according to aspects of the present disclosure;

FIG. 4A is a schematic diagram which illustrates one example embodiment of a user interface according to aspects of the present disclosure;

FIG. 4B is a schematic diagram which illustrates another example embodiment of a user interface according to aspects of the present disclosure;

FIG. 5 is a flow diagram which illustrates an example embodiment of a method for measuring data points relating to force applied to and/or position of a part of a human or animal subject relative to other parts of the human or animal subject according to aspects of the present disclosure;

FIG. 9 is a flow diagram which illustrates the steps required in one possible scenario to measure the biomechanical tissue response with the user applying a random stimulus to one or more teeth;

FIG. 10 is a flow diagram which illustrates an example method for providing real-time feedback based on measurement data;

FIG. 11 is a flow diagram which illustrates an example method for determining or calculating a critical force according to aspects of the present disclosure;

FIG. 12 shows a possible displacement of a tooth within the alveolus resulting from an applied force F;

FIG. 13 show the different locations of the Centre of Resistance of a tooth depending on the tooth and root morphology;

FIG. 14 shows the same force F applied at different points on the tooth and in different directions;

FIG. 28 illustrates a schematic diagram of yet another example user interface for reviewing measurement data obtained using the systems, methods and devices described herein;

FIG. 34 illustrates an example embodiment of a method for comparing forces according to aspects of the present disclosure;

FIG. 35 shows an example embodiment of a method for training a model for use in determining PDL behavior data points according to aspects of the present disclosure;

FIG. 36 shows an example method for using a PDL behavior model to determine movement data points according to aspects of the present disclosure;

FIG. 39 is a flow diagram which illustrates one example embodiment of a method for orthodontic appliance configuration according to aspects of the present disclosure FIG. 40 is a schematic cross-section through two example orthodontic appliances according to aspects of the present disclosure;

FIG. 41 is a schematic diagram which illustrates an example embodiment of an orthodontic apparatus according to aspects of the present disclosure;

DETAILED DESCRIPTION WITH REFERENCE TO THE DRAWINGS

Aspects of the present disclosure relate generally to the field of orthodontic treatment, such as via orthodontic treatment plans and orthodontic appliances. In particular, aspects of the present disclosure relate to an evidence-based approach to the formulation of orthodontic treatment plans and the configuration of orthodontic appliances for improved or even optimal orthodontic treatment outcomes. This evidence-based approach makes use of data points that are obtained from a large number of human or animal subjects in-vivo as well as various other data points, such as metadata relating to the relevant human/animal subject, feedback data (for example including patient feedback and treatment progress/outcome feedback) and the like. The data points can be compiled into a large-scale dataset for processing, optionally together with feedback data, to output models and/or algorithms for use in formulating treatment plans and configuring orthodontic appliances for optimal treatment outcomes. The data points can include periodontal ligament (PDL) behavior data points which can be used to model estimated or expected PDL behavior and determine an optimal orthodontic force (also termed "target orthodontic force" herein), tooth movement and treatment parameters based on the estimated or expected behavior of the PDL. Aspects of the present disclosure aim to build upon existing orthodontic appliance technology using evidence-based inputs for optimal orthodontic treatment outcomes that can be patient, tooth and/or case-specific.

Figure 1A:
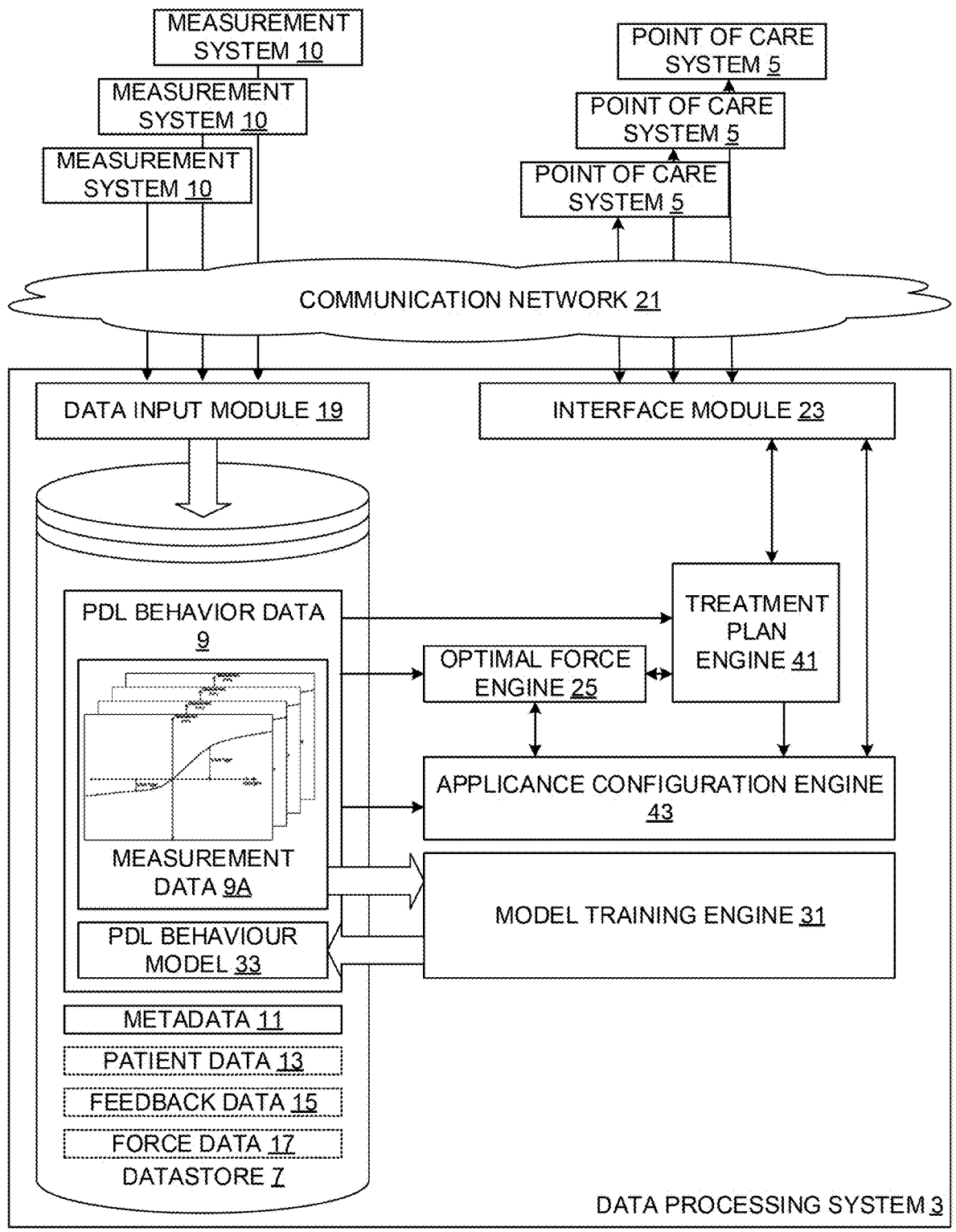
FIG. 1A is a schematic diagram which illustrates an example orthodontic treatment system according to aspects of the present disclosure.

FIG. 1A is a schematic diagram which illustrates an example orthodontic treatment system (1) according to aspects of the present disclosure. The system (1) includes a data processing subsystem (3), a plurality of point of care subsystems (5) and a plurality of measurement subsystems (10).

The measurement subsystems (10) are configured to obtain measurement data from a large number of human or animal subjects, including force measurement data and position measurement data which together describe PDL behavior of the human or animal subject from which the data is measured. The measurement subsystems (10) are configured to obtain measurement data describing PDL behavior when subjected to an applied stimulus. The measurement subsystems (10) may further be configured to obtain metadata associated with the measurement data and/or relevant human or animal subject. The measurement subsystems (10) transmit the measurement data and metadata to the data processing subsystem (3) for storage, processing and/or or analysis. Transmission may be direct transmission or via a communication network (21). It should be appreciated that the measurement systems may be geographically distributed over large distances so as to obtain measurement data from a vast variety of human or animal subjects. As will be explained in greater detail below, each measurement subsystem is configured for low-friction, simple and convenient collection of measurement data to facilitate the compilation of a large-scale collection of measurement data.

The data processing subsystem (3) includes a datastore (7) in which various sets or collections of data may be stored. The datastore (7) may for example store PDL behavior data (9) including measurement data (9A), for example received from the measurement subsystems (10), and/or modelled data, for example in the form of one or more PDL behavior models (33) having been trained on measurement data and associated metadata.

The measurement data (9A) may include a large number of subsets of measurement data, each subset relating to an individual tooth of an individual human or animal subject. The measurement data may for example include time-stamped force measurement data points and corresponding position or displacement measurement data points. Each data point, or value, may have a component for each of six degrees of freedom. Each subset of measurement data is associated with the tooth (e.g., by virtue of tooth type and/or tooth position indicator) with respect to which the data was measured. The measurement data (9A) may be stored in association with the human or animal subject to which it relates (e.g., using an appropriate identifier, key value or the like) such that it can be linked to that human or animal subject and/or to metadata (11) related to that human or animal subject. For example, each subset of measurement data may be associated with an identifier of the human or animal subject with respect to which the data was obtained, for linking with associated metadata relating to characteristics of the human or animal subject. The one or more PDL behavior models (33) may be configured to accept as input either an applied force value or a required tooth displacement value and to output the other of a simulated tooth displacement value resulting from the applied force value or simulated required force value to achieve the required tooth displacement value. The one or more PDL behavior models may further accept as input patient data including patient characteristic data such that the output simulated values are case, tooth and patient specific.

The datastore (7) may further store metadata (11) associated with the PDL behavior data, which may also be received from the measurement subsystems. The metadata may include data points, datasets and/or information relating to one or more of: parameters affecting the PDL behavior, such as data points relating to one or more of tooth and root morphology, PDL thickness and shape of the human or animal subject (including e.g. X-ray data and/or CT scan data) and the like; health related data such as data points relating to one or more of blood pressure, body mass index, weight, oral and tissue health, time in treatment journey (if applicable), smoker/non-smoker status, dental history (including e.g. information on root canal history) of the human or animal subject and the like; data points relating to one or more living standards measure (LSM) inputs, an LSM output, country, state, city of residence and/or birth, diet, age, gender, ethnicity and species of the human or animal subject and the like. The metadata may be stored in association with the human or animal subject to which it relates (e.g., using an appropriate identifier, key value or the like) such that it can be linked to the measurement data obtained from that human or animal subject. The metadata may therefore include data points (including e.g., scores or other indicators) relating to physiological, biological, genetic and situational characteristics of the human or animal subject from whom measurement data is obtained.

In some embodiments, the datastore stores one or more of patient data (13), feedback data (15), target orthodontic force data (17) and the like. In other embodiments, other datastores are provided for the other categories of data needing to be stored.

Patient data (13) may be stored or otherwise accessible to the system for each patient to be treated. Patient data may include patient treatment data and patient characteristic data. The patient data may be associated with the patient to which it relates (e.g., using an appropriate identifier, key value or the like).

Patient treatment data may include data points relating to patient condition and treatment requirements, including for example one or both of a tooth type indicator and a tooth position indicator associated with a tooth or each tooth of the patient to be corrected. The tooth type indicator may be one of: incisor, canine, premolar, and molar, and the tooth position indicator indicates the position of the tooth in the mouth of the patient (e.g. using a standardized numbering convention to allow comparison of like teeth from one person to the next). The patient treatment data may also include treatment movement data (e.g. including one or more treatment movement values) which describes the required tooth movement to effect treatment (or correction) of the tooth. Each treatment movement value may have a component for each of six degrees of freedom. A treatment movement value may for example describe the required translation of the tooth in millimeters along the x-, y- and z-axis and the required rotation of the tooth in degrees around each of the x-, y-, and z-axis. Where multiple teeth are to be corrected, patient treatment data may be provided for each tooth to be corrected or for one or more groupings of teeth to be corrected.

Patient characteristic data may include, for each patient, data points, datasets and/or information relating to one or more of: parameters affecting the PDL behavior, such as data points relating to one or more of tooth and root morphology, PDL thickness and shape of patient (including e.g. X-ray data and/or CT scan data) and the like; health related data such as data points relating to one or more of blood pressure, body mass index, weight, oral and tissue health, time in treatment journey (if applicable), smoker/non-smoker status, dental history (including e.g. information on root canal history) of the patient and the like; data points relating to one or more living standards measure (LSM) inputs, an LSM output, country, state, city of residence and/or birth, diet, age, gender and ethnicity patient and the like. Patient characteristic data for each patient may therefore include data points relating to physiological, biological, genetic and situational characteristics of the patient.

The data processing system (3) receives data from the one or more measurement subsystems (10) and optionally from the one or more point of care subsystems (3). The data processing system (3) may receive data from the one or more measurement subsystems (10) via a data input module (19) and optionally a suitable communication network (21), such as the Internet. The data input module (19) may perform various data standardization, cleaning and formatting requirements as may be required before persisting or storing the received data into the datastore. The data from the one or more point of care subsystems (3) may be received via one or more interface modules (23), which may be provided by one or more suitable APIs, and the communication network (21). The interface module (23) facilitates interacting and integration with other subsystems, such as the point of care subsystems. The interface module may be provided for consumption by the point of care subsystems for the exchange of commands, instructions, requests and data between the subsystems.

In the illustrated embodiment, the data processing subsystem (3) includes an optimal force engine (25) which has access to the datastore (7) and is configured to determine a target (also termed "optimal") orthodontic force based on one or more determinate points of relevant PDL behavior data (9). The optimal force engine (25) may access data from the datastore (7), such as PDL behavior data (9) or one or more determinate points thereof, and process the data to define a target or optimal orthodontic force based on the one or more determinate points and a function which is defined by an algorithm that is maintained and updated by the optimal force engine (25). The optimal force engine may retrieve data that based on patient data that the optimal force engine receives, for example from a point of care subsystem, a treatment plan engine (41), an appliance configuration engine (43), the interface module (23) or the like. In some implementations, the optimal force engine (25) defines the target orthodontic force based on a determinate point being a critical orthodontic force. The optimal force engine (25) is configured to determine the target orthodontic force in relation to a case-specific soft-tissue response of the PDL and the related critical orthodontic force. In some cases, the target orthodontic force is defined as a function of the critical orthodontic force, which is dependent on multiple physiological factors and, as described in greater detail below, may be determined in-vivo. Other implementations use other determinate points. Determining the target orthodontic force may include determining the tissue response of the periodontal ligament, identifying a determinate point along a force-displacement curve and determining an optimal force as a function of said determinate point on the force-displacement curve (e.g., using an optimized algorithm). The optimal force engine (25) maintains and updates the algorithm based on feedback data (15) including one or more of patient feedback data points, treatment feedback data points and test rig feedback data points for outputting a target orthodontic force that can be considered optimal for the given input determinate data.

In the illustrated embodiment, the data processing subsystem (3) includes a model training engine (31) which is configured to train and output one or more models, such as one or more PDL behavior models (33). The models may be mathematical models. The model training engine (31) may access data from the datastore (7), such as PDL behavior data (9) including one or both of measured PDL behavior data (9A) and modelled PDL behavior data (e.g., previously trained PDL behavior models and/or synthetic data which can be generated by other means than in-vivo measurements and could be used to develop models), and process the data to output one or more mathematical models including for example one or more PDL behavior models (33). In some implementations, the model training engine is configured to model the behavior of the PDL based at least to some extent on the in-vivo measurements of said PDL behavior data. In some implementations, as will be explained in greater detail herein, this includes acquiring for a plurality of teeth of a number of individuals measurement data describing PDL behavior when subjected to an applied stimulus; using mathematical models and machine learning techniques to identify features predictive of the behavior of the PDL and training a machine learning (or other suitable) model to produce an estimate of the behavior of the PDL and the resulting tooth displacement when subject to an applied stimulus. The model training engine (31) may thus be configured to output one or more models estimating the behavior of the PDL based at least to some extent on the in-vivo measurements of said PDL for use in modelling patient, case and tooth specific PDL behavior and optionally in determining a target or optimal orthodontic force, tooth movement and treatment parameter based on the estimated behavior of the PDL. The model training engine (31) may implement one or both of a method for modelling periodontal ligament behavior and a method of assimilating patient- and case-specific values of a critical orthodontic force.

In the illustrated embodiment, the data processing subsystem (3) includes a treatment plan engine (41) and an appliance configuration engine (43) which are accessible to the point of care subsystems (5) via the interface module (23) and communication network (21). The treatment plan engine (41) may be configured to access the optimal force engine (25) and PDL behavior data, including the PDL behavior model (33), for implementing a method for orthodontic staging using critical orthodontic force parameters or other suitable PDL-based determinate points. The appliance configuration engine (43) may be configured to access the optimal force engine (25) and PDL behavior data, including the PDL behavior model (33), to implement a method for orthodontic appliance configuration, including designing an orthodontic appliance and preparing a specification for, designing, and producing an orthodontic appliance (such as a clear aligner) using critical orthodontic force parameters or other suitable PDL-based determinate points. A specification for an orthodontic appliance may include one or more configuration parameters which define configuration of the relevant appliance so as to apply a patient, case and tooth specific force that is optimized for patient feedback and treatment outcome.

Each of the point of care subsystems (5) may include any suitable infrastructure accessible to healthcare professionals for the purpose of orthodontic treatment planning and orthodontic appliance configuration, specification and/or design. Each point of care subsystem may for example include a computing device (tablet, laptop, desktop computer, etc.) via which a healthcare professional can interact with the appliance configuration engine (43) and/or treatment plan engine (41) to generate a treatment plan that is patient, tooth and case specific and to configure for manufacture or otherwise specify an orthodontic appliance that applies a target force based on patient, tooth and case specific factors so as to achieve optimal orthodontic treatment. The healthcare professional may for example use the point of care subsystem to input patient data including for example treatment requirements (such as parameters describing the required movement of each tooth of the patient) as well as other required patient data and to receive as output a treatment plan and/or orthodontic appliance configuration parameters for orthodontic treatment that is optimal for the specific patient under consideration.

The orthodontic treatment system (1) may thus provide a distributed computing architecture for using optimal orthodontic forces to produce an optimized appliance design and treatment plan. The computing architecture can include a device for measuring the PDL behavior in-vivo and the resulting measurements can be saved to a storage means or a server for later use. The raw data can be processed by a computer system and can be analyzed to determine for example a critical orthodontic force, and a relating optimal orthodontic force. The system can also include a means for consuming the measured PDL behavior data to develop mathematical models such as Artificial Intelligence (AI) or Machine Learning (ML) models describing the behavior of the PDL or the relating tooth movement resulting from the application of a force to one or more teeth. Such AI/ML models can be developed once or repeatedly and can be updated to include newly measured or estimated data describing the PDL behavior. The system can further include a means for communicating with external services such as a computer system or software process, and can receive data from such services and return data to such services. For example, the system can receive the planned tooth movement from treatment planning software of a point of care system, and a ML model can use such planned movement as an input and return the resulting PDL behavior curve for each tooth as an output. Said output can be received again by a treatment planning software or can be received by another service such as software to design an optimal orthodontic appliance. The PDL behavior curve can be used to optimize the features of an orthodontic appliance, such as the appliance geometry, material, features and parameters defining such features, local placement, orientation, size or shape.

Aspects of the orthodontic treatment system (1) are now described in greater detail below.

Measurement Subsystem and Associated Theory

Aspects of the present disclosure provide a measurement device and associated systems and methods. In particular, aspects of the present disclosure provide a device, system and method for measuring data points and determining a critical orthodontic force using the measured data points. Aspects of the present disclosure may find application in determining and defining the optimal forces for use in the corrective treatment of malocclusion and other dentofacial defects using an orthodontic appliance (e.g., orthodontic aligners or dental braces). The optimal force may be a target orthodontic force based on (or a function of) the critical force.

The measurement device and associated systems and methods described herein may be configured for measuring and quantifying the biomechanical tissue response and relating behavior of the PDL and surrounding tissue and determining a case-specific critical orthodontic force or other determinate point (in some cases in-vivo or at least using measurement data obtained in-vivo). The device may for example include a position sensor and a force sensor configured to measure the tissue response of the PDL of a tooth when subjected to an applied force. The device may include a user-feedback mechanism (e.g., in the form of a user interface) to provide the user with a reading of the determined critical force and/or associated data (such as measurement data). The measurement device, system and method described herein may enable the measurement of data points for plotting a curve defining or quantifying the behavior of the PDL. Such a curve may generally represent the behavior of the PDL in response to certain, measurable, stimuli and may therefore generally be termed herein a "behavior curve", or, in some instances more specifically, a "non-pathologic tooth mobility curve" or a "force-displacement curve". The data points measured herein may be used to define a case-specific critical force level and may be referred to generally as PDL behavior data or measured PDL behavior data.

The measurement device may be a handheld device and is configured for attachment to a part (typically tooth or bone) of a human or animal subject. Once attached a user can impart forces onto the part to which the device is attached by urging the device towards or away from (or generally relative to) the subject. This handheld configuration may provide for a technologically simpler (and hence more cost effective), and in some cases a more convenient or user- and/or subject-friendly, device. The handheld configuration may be provided by shaping and dimensioning the or part of the body of the device so as to fit within the hand of the user.

Figure 1B:
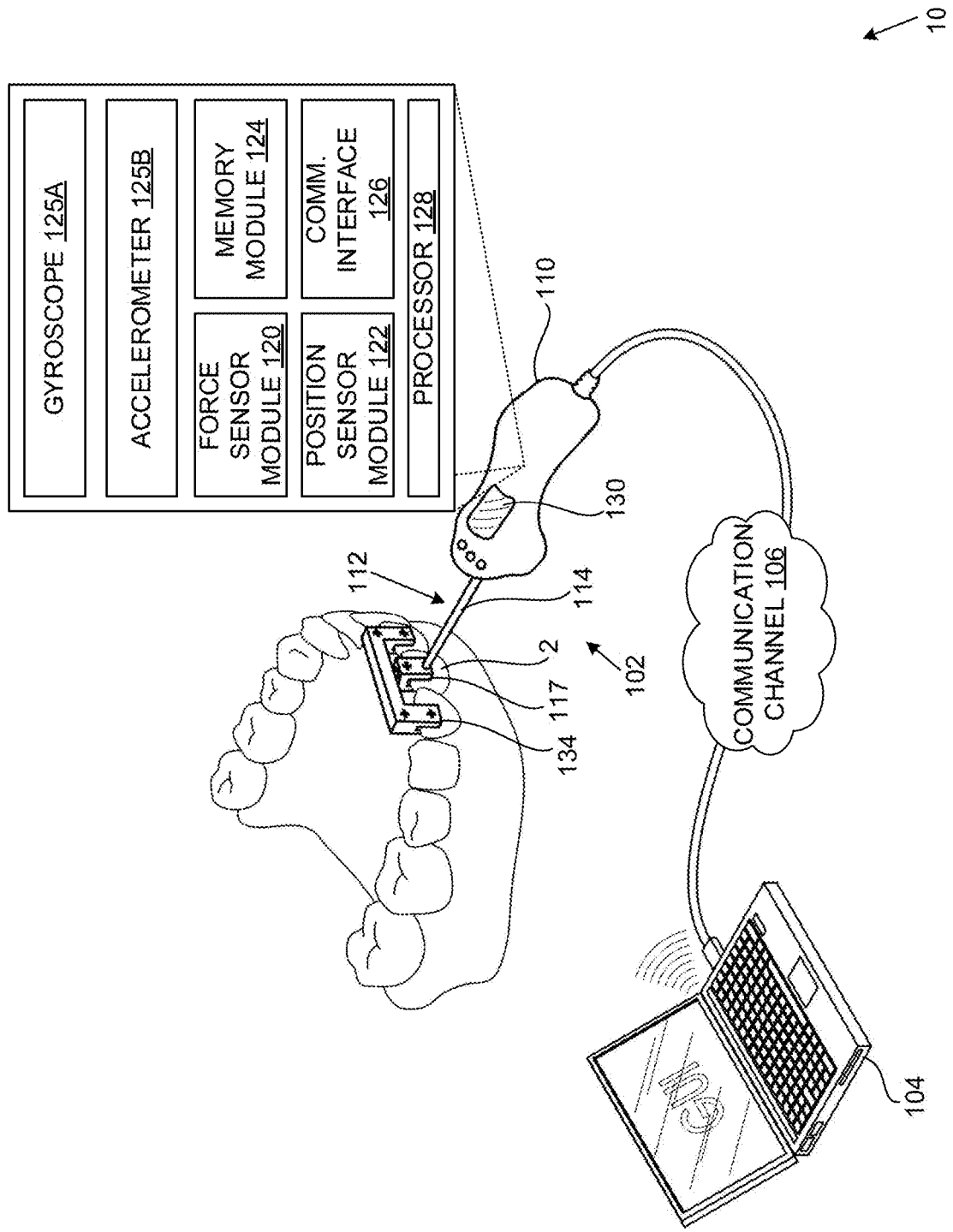
FIG. 1B is a schematic diagram which illustrates an example measurement system according to aspects of the present disclosure.

FIG. 1B is a schematic diagram which illustrates an example measurement system (10) according to aspects of the present disclosure. In the illustrated embodiment, the measurement system (10) includes a measurement device (102) connected to a computing device (104) via a communication channel (106). The communication channel may be provided by a wired or wireless connection between the computing device and the measurement device. The communication channel may be provided by a network, such as a local area network or a wide area network (e.g., including a publicly accessible communication network, such as the Internet). In the example embodiment illustrated in FIG. 1B, the computing device (104) is a laptop computer although in other implementations the computing device may take on other forms, such as a tablet computer, mobile phone (or smartphone), personal digital assistant, desktop computer or the like. In other embodiments, the measurement device may be a stand-alone device that operates without connection to an external device but which, for example, communicates with a data processing system (3) via a communication network (21).

The measurement device (102) includes a body (110) and an attachment mechanism (112) fixed to and extending from the body.

The body (110) is configured for gripping by a user. In the illustrated embodiment, the body is configured for gripping by a user in that it is shaped and dimensioned to fit within the hand of a user. For example, the body may have an elongate and generally cylindrical shape. In some embodiments, the body is ergonomically shaped for example including contours that are shaped and dimensioned to accommodate individual fingers and a thumb of a user and/or the shape of a user's closed hand. The body may be shaped as a handle and may include non-slip formations or features, such as knurled surfaces, rubberized surfaces or the like. In other embodiments, a part of the body, such as a handle, is configured for gripping by a user while another part is not so configured.

The attachment mechanism (112) is configured for attachment to a part of a human or animal subject, in this example embodiment being a tooth (2). The attachment mechanism provides a means for creating an attachment to a tooth to transfer a stimulus or force in multiple directions. The attachment mechanism includes a shaft (114) terminating in an attachment formation configured for attachment to the intended part of the human or animal subject (in this case being a tooth). The shaft is attached to the body such that a force applied to the body is transferred via the shaft to the attachment formation and, in use, to the part of the human or animal to which the attachment formation is attached. In some embodiments, the shaft is rigid and may be rigidly attached to the body. In some embodiments, the attachment of the attachment mechanism to the body of the measurement device may be by way of a shock absorbing or damping mechanism. The mechanism may be interposed between the shaft (114) and the body (110) so as to absorb or damp sudden movement applied to the tooth via the attachment mechanism and body of the measurement device. The force sensor module (120) may be located on a proximal end of the shaft (i.e., the end opposite that to which the attachment formation is fixed) and may be connected to the body via the shock absorbing or damping mechanism such that force is transferred from the body to the shock absorbing or damping mechanism and then to the shaft via the force sensor module. This arrangement may improve subject comfort and may also improve the quality of the measurements as the force applied to the tooth (and measured by the sensor module) will be smoother by virtue of the shock absorbing or damping mechanism.

In the embodiment illustrated in FIG. 1B, the attachment formation includes a clamp (117) secured to the shaft and configured to clamp onto the tooth.

FIGS. 2A and 2B illustrate two further example embodiments of an attachment formation (116A, 116B) according to aspects of the present disclosure. In the example embodiment of FIG. 2A, the attachment formation (116A) includes a head (117A) connected to a cap (117B) that fits onto the tooth. The cap provides a clamping mechanism that attaches to and clamps onto the tooth of a patient. The cap may be releasably fixed in place using a suitable bonding agent (118). The cap may for example be a silicone cap which can be removably secured to the tooth or to a plurality of teeth. In the example embodiment of FIG. 2B, the attachment formation (116B) includes a bracket connection formation (119A) configured to connect to a bracket (119B) that is releasably fixed to the tooth. The bracket may be fixed to the tooth using, for example, a bonding agent, UV curable resin or other suitable dental materials for releasably securing the bracket to the tooth. The bracket includes a clip, flanged protuberance or other suitable connection formation which is configured to cooperate with a corresponding receiving formation of the bracket connection formation. The receiving formation may for example be in the form of a claw, clasp or other formation configured to receive and hold captive the connection formation of the bracket. Any other form of mechanical mechanism can be used to create a temporary fixture to the tooth or for the user to hold on to the target tooth and apply a force and moment. In other embodiments, the attachment mechanism may be configured for attachment to a group of teeth (e.g., to adjacent incisors, molars or the like), in which embodiments the force and position measurements obtained by the measurement device relate to the group of teeth and not to individual teeth.

Figure 3C:
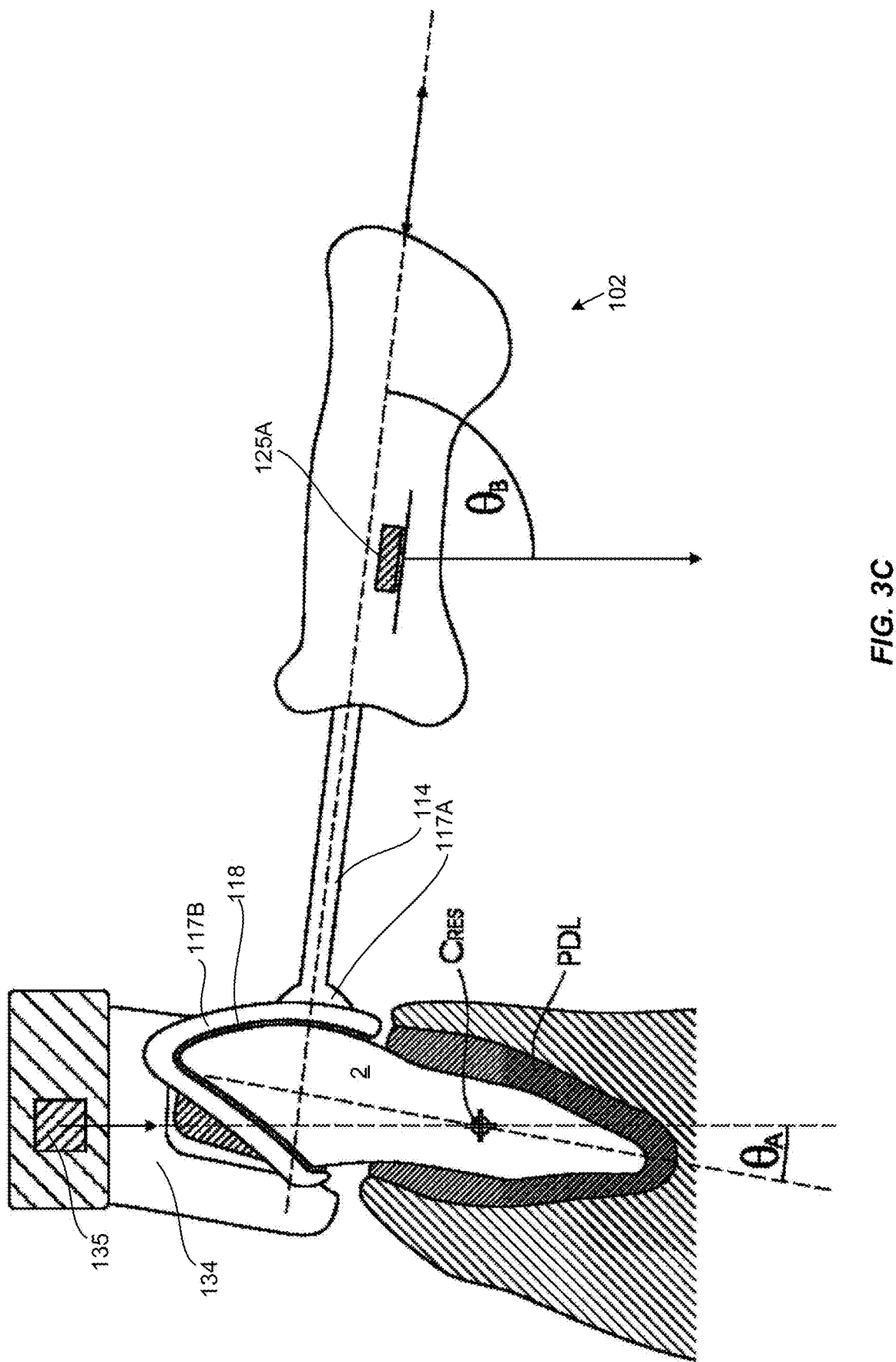
FIG. 3C is a schematic diagram which illustrates an example use of gyroscopes in the measurement system of FIG. 1B.

The body includes or houses one or more of a force sensor module (120), position sensor module (122), a memory module (124), one or both of a gyroscope (125A) and an accelerometer (125B), an external communication interface (126) and a processor (128) which may be interconnected via a suitable internal communication system, interface or bus(es) (I2C, SPI, etc.). The measurement device (102) includes or is in communication with a user interface (130). The gyroscope (125A) and accelerometer (125B) may be included in the body and/or the reference jig (e.g., as illustrated in FIG. 3C) and may be configured to determine the acceleration and rotation and/or orientation of the device, respectively, and the corresponding direction of the force. The gyroscope (125A) is configured to output rotation and/or orientation measurement data and the accelerometer (125B) is configured to output acceleration measurement data. In the illustrated embodiment, the memory module is shown as being a part of the measurement device. In other embodiments, the memory module may be provided by a remote or cloud-based storage. For example, in some embodiments, the memory module may be provided by the datastore (7).

The force sensor module is configured to measure a force applied to the attachment mechanism, in use, and output force measurement data relating to the measured force. The force sensor module measures the force applied to the attachment formation, and in turn the part of the human or animal, via the shaft and body. The force sensor module may include one or more commercially available sensors that allow a force to be measured along at least one dimension. In some cases, the force sensor module may include an integrated six degrees of freedom force sensor. In some embodiments, the force sensor module may include a custom force sensor or force transducer (e.g., in the form of one or more load cells) configured to measure data points relating to a force applied by the user. The force sensor module may output force measurement values for each of six degrees of freedom, for example a translation value and a rotation value along or about each of the x-, y-, and z-axis.

The position sensor module is configured to measure the position of the part of the human or animal relative to other parts thereof, in use, and output position measurement data. The position sensor module may include one or more of a camera, accelerometer, gyroscope, magnetometer, Hall effect sensor or the like. In the example embodiment illustrated in FIG. 1B, the position sensor includes a camera and computer vision system configured to locate position of tracking points (132) in image data to calculate the relative change in position, and hence to determine movement or displacement, according to the biomechanical response. The tracking points may be existing, distinguishable points that the computer vision system identifies automatically, may be drawn directly onto the target tooth (2) and surrounding teeth or may be provided on an attachment formation (such as a head, cap, clamp bracket connection formation) and a reference jig (134) that is fixed to the teeth. The position measurement data may be used to calculate or determine tooth displacement, for example by tracking a series of different tooth positions over a period of time, and to output tooth displacement or movement data. It should be appreciated that the position measurement module described herein is configured to measure position of a target tooth relative to other teeth, which is different from measuring changes in position between the target tooth and the body of device. This may enable a decoupling of device movement from tooth movement which may improve accuracy of the position measurements given the handheld nature of the device (and there may hence be no fixed reference point).

The force measurement data and position measurement data may collectively be referred to herein as biomechanical response data.

An example reference jig (134) setup is illustrated more clearly in FIG. 3A. The reference jig is configured for attachment to a plurality of teeth which are proximate or adjacent the target tooth (2). The reference jig can include several tracking points. These tracking points are suitable for visual identification and location using a computer vision system. The reference jig is placed into the mouth in such a way that it remains unaffected by a stimulus being applied to the target tooth and thus does not move. FIG. 3B illustrates an example of the field of view of the camera and computer vision system used to measure the biomechanical tissue response. The camera is configured in such a way that it is able to capture image data (136) including the tracking points on the reference jig as well as the tracking points on the target tooth. Sufficient tracking points are located on the reference jig and the target tooth for the computer vision system to be able to calculate the relative movement or displacement of the target tooth relative to the reference jig with six degrees of freedom including translation and rotation around all three axes. The camera and/or computer vision system may therefore be configured for use in capturing image data including reference points on a target tooth and reference points on the one or more other teeth and allowing measurement of the biomechanical tissue response.

Referring now to FIG. 3C, in some embodiments the reference jig (134) includes an accelerometer and/or gyroscope (135) which may transmit acceleration measurement data and rotation and/or orientation measurement data to the processor of the measurement device. The processor can process the reference jig accelerometer/gyroscope data together with the measurement device accelerometer/gyroscope data to determine components of each of the six degrees of freedom of the force measurement data and the position measurement data. The accelerometers and/or gyroscopes provided in the body of the device and/or the reference jig enable the determination or calculation by the processor of components of each force measurement data point for each of six degrees of freedom. The accelerometer or gyroscope measurement data may be used to determine the relative direction of application of a force, thereby allowing the orientation and each of the six degrees of freedom of the measured force data and the measured displacement data to be determined.

In another example embodiment, the position sensor module includes a magnetic sensor system (e.g., including one or more magnetic sensors, such as Hall effect sensors). The magnetic sensors may be housed within a reference jig and in data communication with the measurement device (e.g., via the external communication interface). A magnet may be fixed to the target tooth (or, e.g., housed within an attachment formation of the device). The reference jig is attached to other teeth or part of the dental complex in such a way that is not affected by the stimulus being applied to the target tooth. If a force is applied to the target tooth, this will cause the tooth to move relative to the reference jig. This relative displacement will be sensed by the magnetic sensor system. Sensor data from the magnetic sensor system may be transmitted to the device for processing to determine position measurement data. In this embodiment, the device uses a magnetic sensor system to measure the tissue response. The system makes use of a magnetic sensor integrated into a reference jig and a magnet that is attached to the tooth to which a stimulus is being applied.

The memory module is configured to store measurement data, including the force measurement data and position measurement data, displacement measurement data and optionally rotation and/or orientation and/or acceleration measurement data as well. The data may be stored in association with the target tooth (e.g., by way of tooth type and/or tooth position indicator) and a human/animal subject identifier for linking the measurement data to metadata associated with the human/animal subject. In the embodiment illustrated in FIG. 1B, the memory is illustrated as being internal to the device. In other embodiments, the memory in which measurement data is stored may be provided by a remote device (such as a computing device).

The processor may be configured to manage and/or control the various modules of the measurement device. The processor may be configured to receive measurement data from the sensor modules, process, timestamp, filter, output and/or store the measurement data received from the various sensor modules. The processor may be configured to process position measurement data to determine displacement measurement data. The processor may for example store the measurement data (and associated data, such as timestamps) in the memory module. The processor may be configured to output measurement data, reference data and/or target data to the user interface. The processor may further be configured to transmit the measurement data and/or associated metadata to the computing device via the communication channel (106). The processor may implement a feedback system using one or more of the force sensor module, position sensor module and user interface.

The user interface may be configured to output to the user one or both of the force measurement data and the position measurement data. In some embodiments, the user interface is configured to output to the user one or both of force reference data and position reference data. In some embodiments, the user interface is configured to output to the user one or both of force target data and position target data. In some embodiments, the user interface is configured to display the force measurement data and force reference data. The force measurement data and force reference data may for example be overlaid or otherwise shown together to facilitate matching by the user, in use through manipulation of the body, of the force measurement data to the force reference data. The user interface may therefore be configured to guide application of force by the user. The user interface may include an input element (e.g., provided by way of keyboard, buttons, touch-sensitive display) for input of information such as a patient identifier, tooth (or body part) identifier or the like.

In the embodiment illustrated in FIG. 1B, the measurement device includes a user interface (130) integrated into the body. The user interface may for example be provided by one or more LEDs, a liquid crystal (or other suitable) display or the like. In some embodiments, the measurement device is in communication with a user interface, which may for example be provided by the computing device (104).

FIG. 4A illustrates one example embodiment of a user interface provided by a computing device, for example in the form of a tablet or laptop computer. The user interface may include one or more windows including graphical representations of measurement data, reference data and/or target data. One example window includes a gauge (140) which overlays a graphical representation of force measurement data (142) with a graphical representation of force reference data (144) so as to guide the user as to the actual force he or she is applying to the tooth versus the desired or required force for plotting of a behavior curve. A magnitude of the force measurement may be displayed (145) in the center of the gauge.

Another example window includes a one or more arrows (146), where each arrow is a graphical representation of force measurement and/or reference data and can have varying properties including for example length, size, or color, such properties being varied based on the desired and the measured stimulus and being adjusted so as to provide the user with instructions on how to change the applied stimulus to the target tooth.

Another example window includes a graphical representation of the reference and/or the measured force in three-dimensional space. The signals can be superimposed on image data (148) or a three-dimensional rendering of the one or more teeth. The same visualization can also be used to visualize the reference (e.g. target or desired) force (150) and the measured force (152), and may also include a visualization of a reference moment (154) and a measurement moment (156). The displayed signal can include any properties describing the force with six degrees of freedom, each having one or more of a direction, a magnitude, a duration, and frequency of application.

Another example window includes a graphical representation of force measurement and reference data by way of a time series visualization (158) of the desired reference (159A) and the measured (159B) forces in real-time. The reference signal can have at least a direction and a magnitude, as well as time dependent characteristics including but not limited to frequency, rate of change, duration of application and the like.

One or more of these windows may be provided by way of the user interface so as to provide feedback and instructions to the user. The user interface can include information about the desired reference forces to be applied to the target tooth as well as the actual measurement of forces, which can be displayed in real time.

FIG. 4B illustrates one example embodiment of a user interface provided by a computing device, for example in the form of a mobile phone. The user interface may include one or more windows including graphical representations of measurement data, reference data and/or target data. One example window includes a three-dimensional visualization (160) of the teeth and the target tooth and a superimposition of the graphical representations of the measured (162) and reference (164) force data. The forces can be visualized in real-time. The representation of the forces can include the magnitude, direction and other parameters describing the desired or the applied stimulus. The user interface can vary the parameters of the signal including the size, orientation, length or color to be indicative of the displayed signal.

The user interface may be configured for input of one or both of a tooth type indicator and tooth position indicator associated with each of the teeth and the human or animal subject from which measurements are to be or have been taken. The user interface may be configured for input of metadata associated with the human or animal subject from which measurements are to be or have been taken. The tooth type indicator and tooth position indicator may be stored in the memory module in association with the measurement data. The metadata may be stored in the memory module in association with a human/animal subject identifier (e.g., human ID) for linking the metadata to the measurement data.

In another example window the user interface can provide instructions to the user on how to adjust the current applied stimulus so as to better represent the desired stimulus. Such a visualization can make use of one or more arrows (166), each of which can have properties including the size, color, length and orientation, which can be changed so as to prompt the user to apply a stimulus which better represents the desired stimulus. Said properties can be changed based at least to some extent on one or more of the desired stimulus and the measured stimulus. A magnitude of the force measurement may be displayed (168) in the center of the base from which the one or more arrows extend.

The system and device described above may be used for the measurement, storage and transmission of force and position data, for example as applied to and measured from a part of a human or animal subject. The force and position measurement data may be used to plot a behavior curve relating to the relevant part of the human or animal subject. While the system and device of FIG. 1B are described with reference to an example illustration in which the device is connected to computer via a wired connection, it should be appreciated that in other implementations the device can also operate in stand-along mode without a connection to any external device, or can be connected to a computer, a phone, tablet or any other suitable computing device in this way. The connection can be in the form of a USB or other connection and can provide both data communication and or power supply to the device. The device can also connect to any other electronic device or interface using any form of wireless communication including for example Wi-Fi, Bluetooth or the like.

The measurement device described above utilizes energy from a human user or operator to impart forces onto the tooth or teeth of the human or animal subject. It should however be appreciated that other embodiments anticipate other mechanisms for imparting such forces. For example, some embodiments of a measurement device according to aspects of the present disclosure may include a hydraulic or piezoelectric actuator controllable by the user so as to apply a desired force. Measurement devices according to aspects of the present disclosure therefore enable a user-controllable force to be imparted on or applied to a tooth or teeth of a human or animal subject for the purpose of measuring a corresponding displacement of that teeth or those teeth. The arrangement of the measurement device (i.e., user controllable force and decoupled displacement/position measurement features) may reduce noise in the measurement data collected by the device.

The measurement system and/or device may implement a method for measuring data points relating to force applied to and/or position of a part of a human or animal subject relative to other parts of the human or animal subject. FIG. 5 is a flow diagram which illustrates an example of such a method. The method may be conducted by a measurement device (102), such as that described in the foregoing.

The method may include receiving (201) an instruction to commence measuring. In some embodiments, this may include receiving a user input instruction, for example an instruction from the user to start measuring, an instruction indicating that the device has been attached to a part of a human or animal subject, or the like. The user input can be input into the user interface (e.g., by clicking or selecting "Proceed with measurements", "Ready to measure", "Attachment successful", "Start" or the like). In other embodiments, receiving the instruction may include receiving an auto-generated (i.e., device generated) instruction which may for example be generated by the device in response to the device detecting attachment of the attachment mechanism to a part of the human or animal subject.

Receiving the instruction to commence measuring may thus include receiving or otherwise be associated with an indication of attachment of an attachment mechanism of the measurement device to a part of a human or animal subject. As described in the foregoing, the attachment mechanism is fixed to and extends from a body of the device which is configured for gripping by a user.

In response to receiving the instruction, the device may start sampling data points. This may include instructing the appropriate sensor modules to start sampling data points; receiving, processing and/or storing data points and the like. Receiving the instruction may thus trigger the sampling of data points.

The method includes receiving (202) force measurement data and receiving (204) position measurement data. The force measurement data may be received from a force sensor module and the position measurement data may be received from a position sensor module. Each of the force measurement data and position measurement data may include a series of data points relating to discrete force and position measurements, respectively, obtained at specific points in time. Each set of data therefore describes changes in an applied force and changes in a position of the part of the human or animal subject relative to other parts, respectively, over a period of time. The modules from which the data is received may be configured with a high sampling frequency, such that a number of data points are measured per second, for example. The sensors may for example obtain measurement samples at anywhere between 10 Hz and 50 kHz. The processor can apply filtering, averaging or smoothing to the sample points.

Figure 19A:
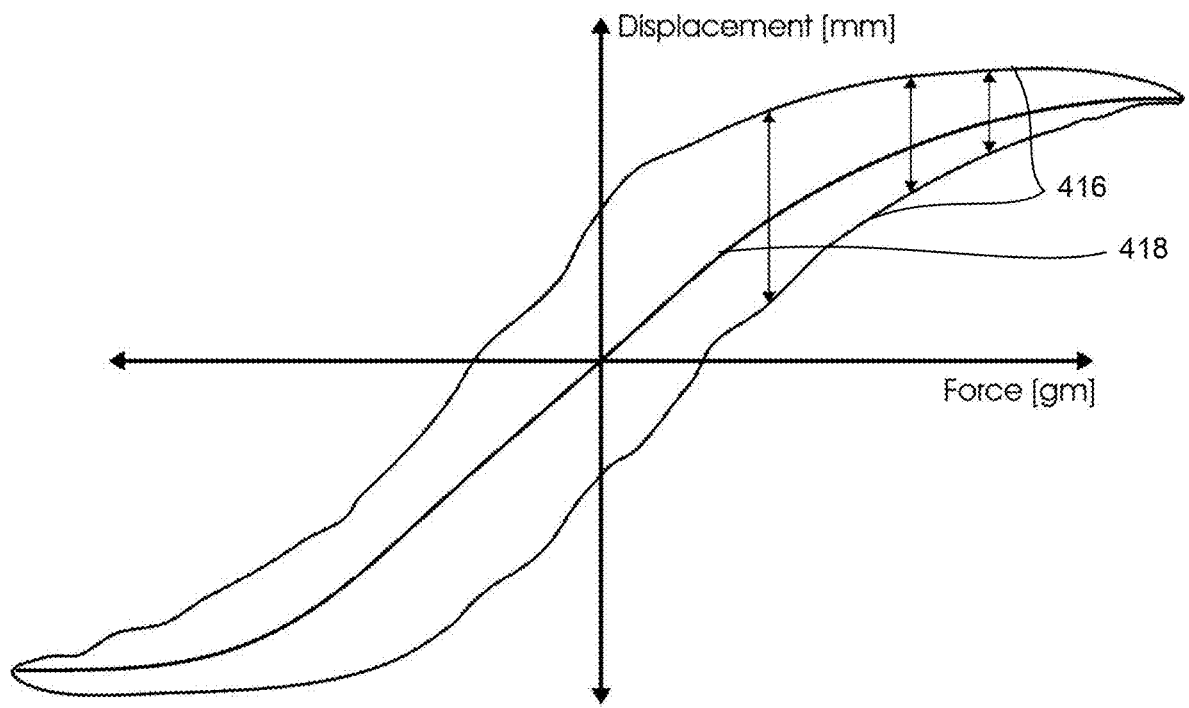
FIG. 19A shows an example of raw data measured from the biomechanical tissue response resulting from an applied stimulus to a tooth, as well as an average curve describing the force displacement relationship for a back-and-forth movement of the same tooth.
Figure 19B:
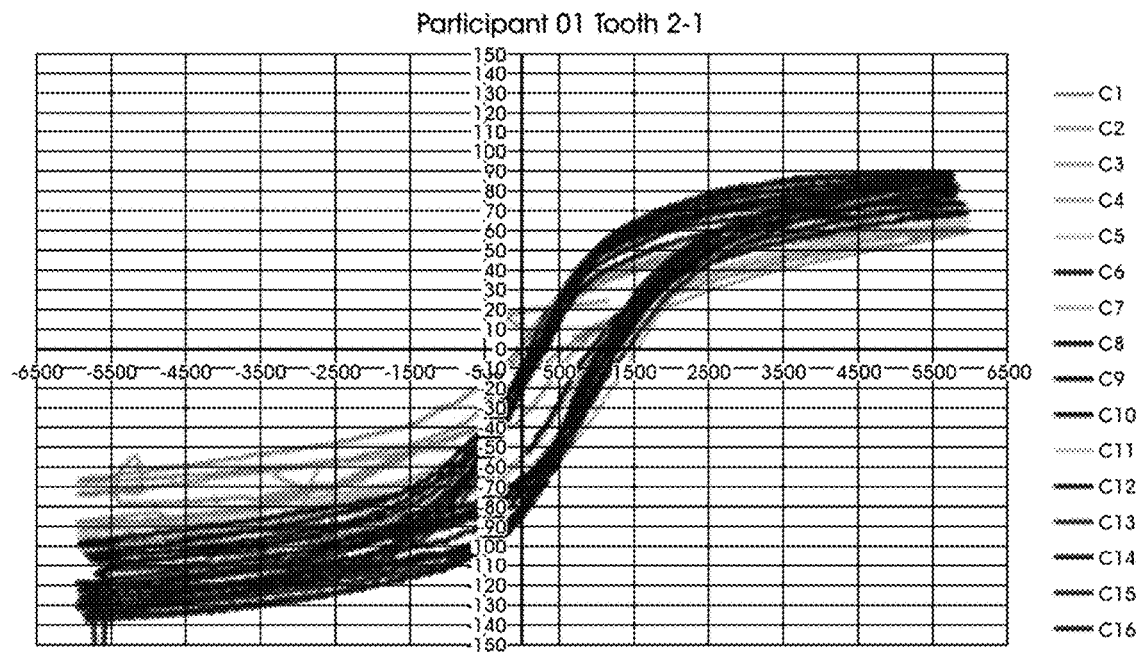
FIG. 19B shows another example of raw data measured from the biomechanical tissue response resulting from an applied stimulus to a tooth.
Figure 19C:
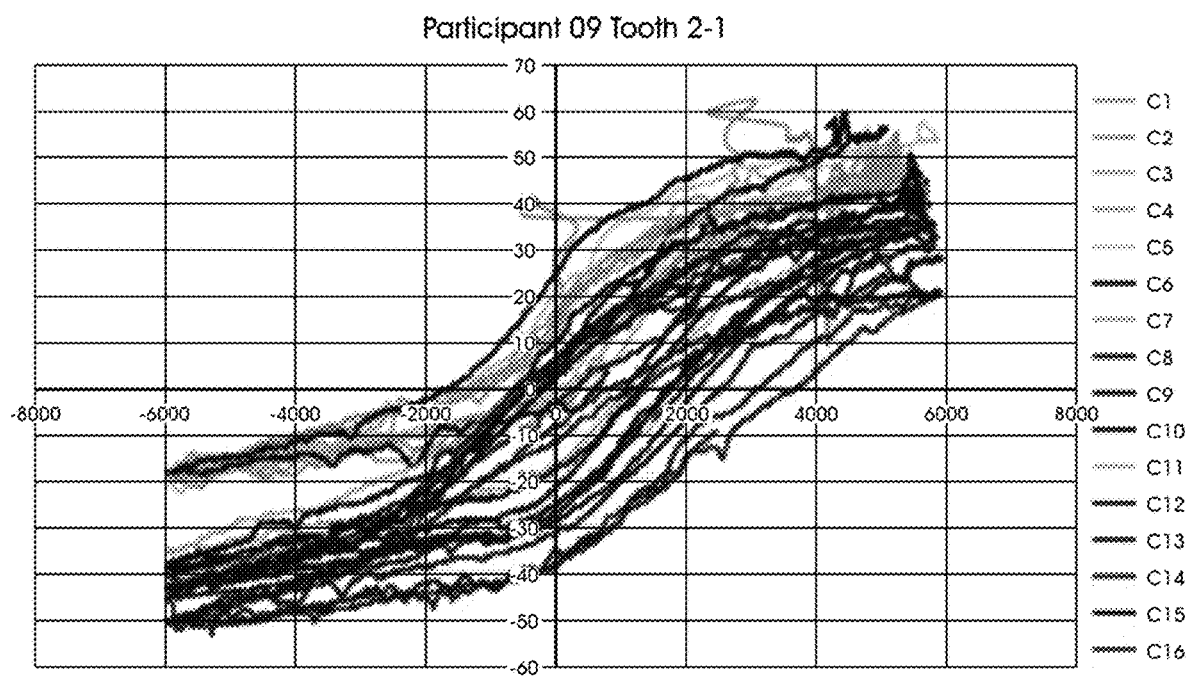
FIG. 19C shows yet another example of raw data measured from the biomechanical tissue response resulting from an applied stimulus to a tooth.

The received data may be timestamped (e.g., by the respective modules by which they are measured) and/or the method may include timestamping (206) the force measurement data and position measurement data as it is received. Timestamping may include timestamping filtered, averaged or smoothed sample points. Timestamping operates to relate a given force measurement data point to a corresponding position measurement data point so that a plot of the relationship between force and displacement can be generated (e.g., as shown in FIGS. 19A-19C).

The method includes storing (208) and/or transmitting (210) measurement data, including the received and timestamped force measurement data and position measurement data. Storing or transmitting the received and timestamped force measurement data and position measurement data includes storing or transmitting force measurement data points and corresponding displacement measurement data points having been measured in-vivo while applying a force to a particular tooth of a human or animal subject. The data may be stored in the memory module for offline retrieval (e.g., for uploading at a later point) or may be transmitted to the computing device or a remote server. Storing the measurement data may for example include storing the measurement data in a comma separated value (CSV) or appropriate format. Stored measurement data may for example take on the form:

yyyymmddhhmmssms,Ftx,Fty,Ftz,Dtx,Dty,Dtz,Fmx, Fmy,Fmz,Dmx,Dmy,Dmz, , ,
20200412084530900,12.30,2.10,32.65,11.34,18.10,9.50, 128.20,90.40,23.43,78.23,−12.30,−98.20, , ,
20200412084530905,13.00,2.30,33.98,11.90,17.50,9.50, 137.80,−95.60,−20.98,83.45,−5.40,−98.41, , ,
20200412084530910,13.70,1.20,35.31,12.10,17.95,9.56, 143.20,−98.70,−18.87,89.67,−0.23,−98.98, , ,
20200412084530915,14.40,1.80,36.64,12.54,17.70,9.58, 151.40,−103.20,−16.53,95.22,6.09,−99.31, , ,
20200412084530920,15.10,1.35,37.97,12.92,17.63,9.61, 158.90,−107.35,−14.25,100.94,12.13,−99.70, , ,
20200412084530925,15.80,1.15,39.30,13.30,17.55,9.64, 166.40,−111.50,−11.97,106.66,18.16,−100.09, , ,
20200412084530930,16.50,0.95,40.63,13.68,17.48,9.67, 173.90,−115.65,−9.69,112.38,24.20,−100.48, , ,
20200412084530935,17.20,0.75,41.96,14.06,17.40,9.70, 181.40,−119.80,−7.41,118.10,30.23,−100.87, , ,
20200412084530940,17.90,0.55,43.29,14.44,17.33,9.73, 188.90,−123.95,−5.13,123.82,36.27,−101.26, , ,
20200412084530945,18.60,0.35,44.62,14.82,17.25,9.76, 196.40,−128.10,−2.85,129.54,42.30,−101.65, , ,
20200412084530950,19.30,0.15,45.95,15.20,17.18,9.79, 203.90,−132.25,−0.57,135.26,48.34,−102.04, , ,
20200412084530955,20.00,−0.05,47.28,15.58,17.10, 9.82,211.40,−136.40,1.71,140.98,54.37,−102.43, , ,
20200412084530960,20.70,−0.25,48.61,15.96,17.03, 9.85,218.90,−140.55,3.99,146.70,60.41,−102.82, , ,
20200412084530965,21.40,−0.45,49.94,16.34,16.95, 9.88,226.40,−144.70,6.27,152.42,66.44,−103.21, , , The method may include outputting (212) the measurement data (e.g. one or both of position and force measurement data) to a user interface. Outputting the data may include outputting reference data (e.g. one or both of position and force reference data) to the user interface. The measurement data and reference data may be overlaid or juxtaposed or otherwise displayed so as to guide the user as to the application of force. Example arrangements of measurement and reference data output to a user interface are illustrated in FIGS. 4A and 4B. The method repeats (214) for continual receiving, timestamping, storing, transmitting and/or outputting of measurement data.

Aspects of the present disclosure are directed specifically to the measurement of data points relating to force applied to, and position of, a target tooth of a human subject relative to other teeth of the human subject. The measurement data is obtained for the purpose of plotting a behavior curve that describes the relationship between changes in forces applied to the target tooth and changes in position of the target tooth relative to the other teeth. Such a curve may be useful in determining an optimal force for use in the corrective treatment of malocclusion and other dentofacial defects using an orthodontic appliance or aligners. More specifically, an optimal force that is patient- (or subject-) specific, tooth specific and, in some cases, stage of treatment regimen specific may be determined.

The measurement data may be obtained using a measurement device that has no internal mechanism for applying a force. Instead, the measurement device may be configured to transfer a force that is applied to the device by a human user onto a target tooth to which the device is attached. In order to guide the human user as to the appropriate force to apply, the device may include a user feedback system configured to output measurement data to the human user via an appropriate user interface.

Figure 6:
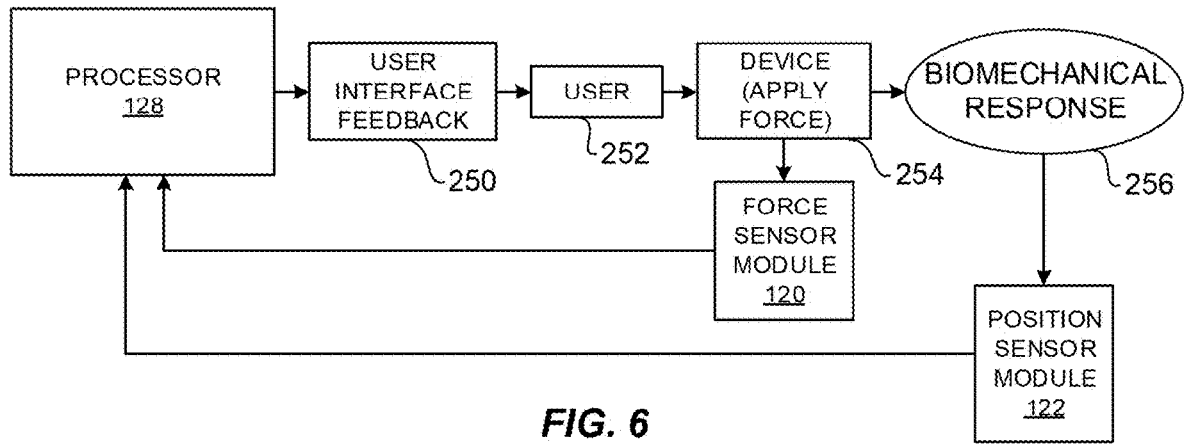
FIG. 6 is a schematic diagram which illustrates elements of a feedback system according to aspects of the present disclosure.

FIG. 6 is a schematic diagram which illustrates an example embodiment of a feedback system implemented by the measurement system and device described herein. The processor (128) is configured in such a way as to provide feedback (250) to the user (252) via a user interface with an indication that the user can apply a stimulus such as a force to the target tooth. The user feedback can include instructions to the user regarding what stimulus to apply, the magnitude of force as well as the dynamic or movement applied to the tooth. In addition, the device can notify the user in case an incorrect stimulus is being applied. In its simplest form the user interface can be minimalistic and use only indicator LEDs. In a more advanced version of the UI the user can see the measured stimulus and resulting biomechanical tissue response in real-time as well as real-time analytics showing parameters relating to the behavior of the biomechanical tissue response (e.g. as illustrated in FIGS. 4A and 4B). This step can make use of the indicator LEDs, a screen on the device or a user interface on a computer. The user holds the device and applies (254) a stimulus to the target tooth to which the device is connected via the shaft and attachment. The device force sensor module (120) is configured to measure the stimulus applied by the user in real-time and to provide the measured stimulus back to the microprocessor in the form of one or more data points. The signal received by the processor can be processed and the data received can be used to determine a new signal or user feedback provided to the user. In addition, the position sensor module is configured in such a way as to measure the biomechanical tissue response (256) in real-time. This position sensor module (122) is also configured in such a way as to provide one or more data points back to the processor. The processor can make use of the data received describing the applied stimulus (force measurement data), the data received describing the biomechanical tissue response (position measurement data) or a combination of the two to determine the user feedback and signal. The device can make use of a user interface to display the data in any form and in real-time.

Figure 7:
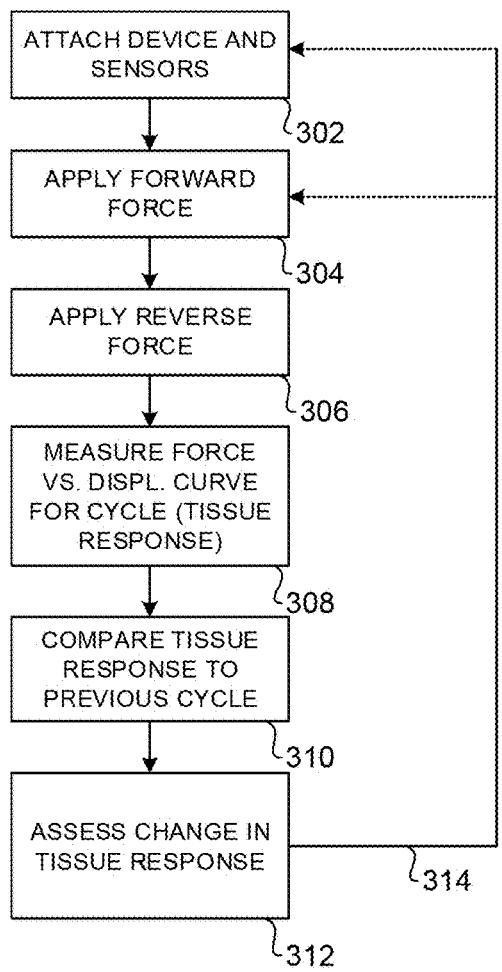
FIG. 7 is a flow diagram which illustrates steps for one example use-case for determining a biomechanical tissue response using the measurement device described herein.

Referring now to FIG. 7, in one possible use case, the device (102) is attached (302) to a target tooth using an attachment mechanism to the tooth. The user of the device then applies (304) a stimulus in the form of a forward (pushing) force to the tooth, which is followed by an application (306) of a force in the opposite direction (pulling force). The device measures (308) the applied stimulus in real-time as well as the resulting biomechanical tissue response in real time (e.g. as described above with reference to FIG. 5). The device compares (310) the measured biomechanical tissue response to previous cycles. The device assesses (312) the change in the biomechanical tissue response and depending on the assessment, provides the user with an indication of what stimulus to apply. Typically, the assessment will include changes in the displacement, the gradient (or "ease of movement"), for example as described in FIGS. 20-25. This process can be repeated (314) for the same tooth, or on another target tooth. Repeating (314) the process may include recommencing the process at applying (304) a forward force or at attachment (302) of the device and sensors. In other words, the process may be repeated for the same tooth or for another tooth.

Figure 8:
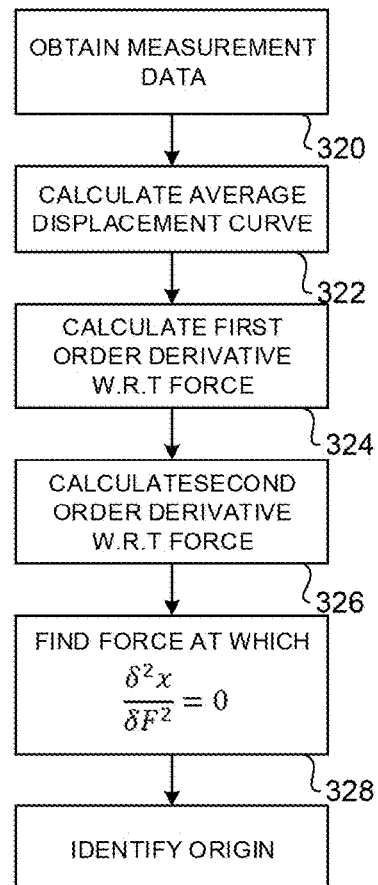
FIG. 8 is a flow diagram which illustrates an example method for determining the neutral position of a tooth in in biomechanical response data.
Figure 25:
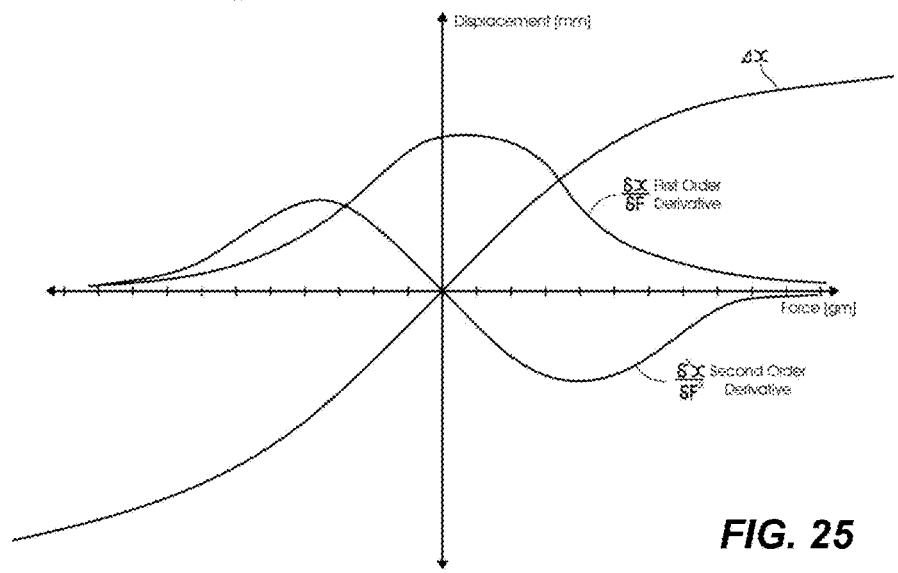
FIG. 25 shows an example of the mathematical processing of the biomechanical tissue response curve allowing the quantitative description of the behavior of the PDL.
Figure 26:
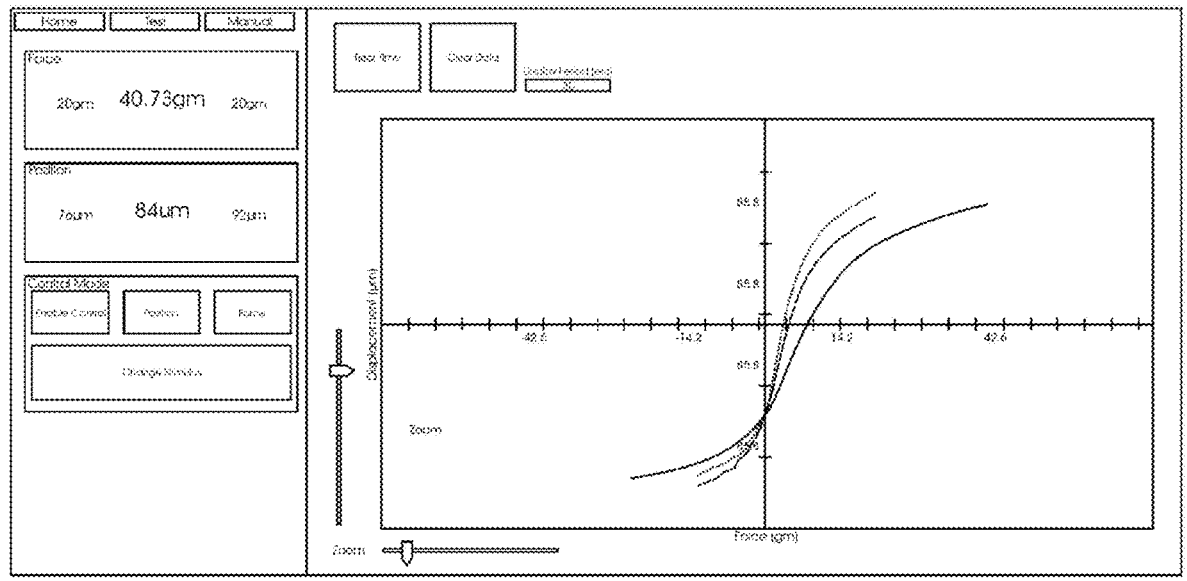
FIG. 26 illustrates a schematic diagram of an example user interface for reviewing measurement data obtained using the systems, methods and devices described herein.
Figure 27:
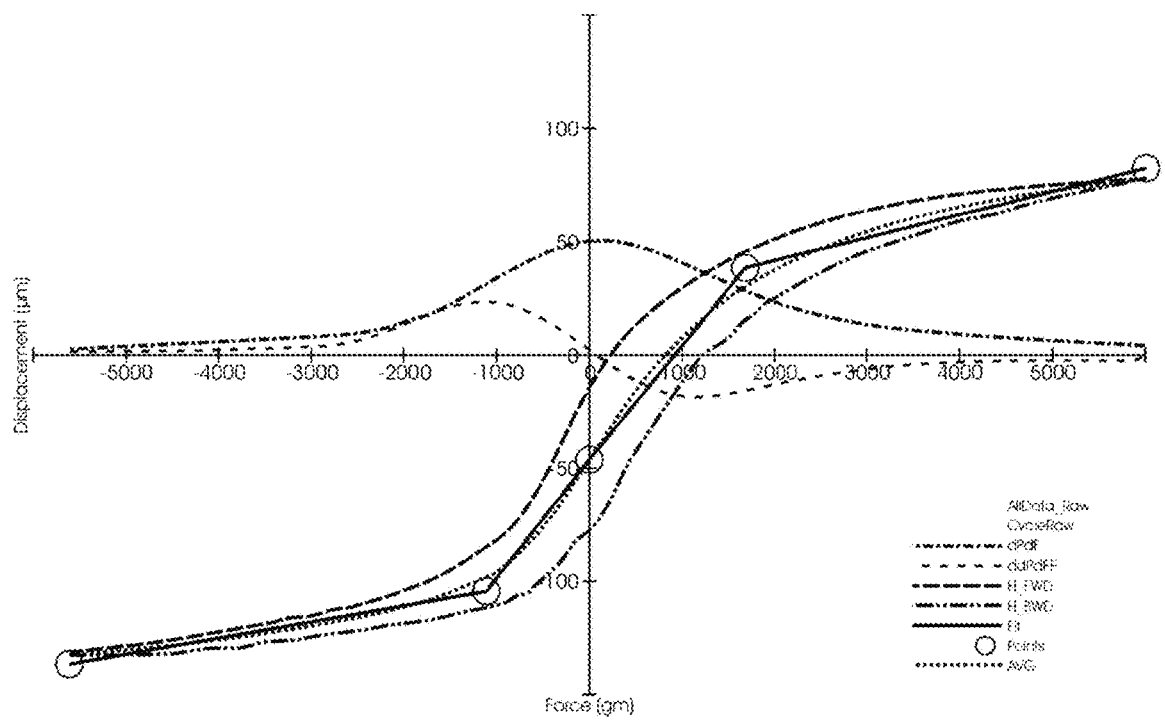
FIG. 27 illustrates a schematic diagram of another example user interface for reviewing measurement data obtained using the systems, methods and devices described herein.

In cases where a cyclic stimulus is applied to one or more teeth in a back and forth motion (e.g. as in the example use-case described above with reference to FIG. 7), the neutral position of the tooth may need to be identified from the raw data. FIG. 8 is a flow diagram which illustrates an example method for determining the neutral position of a tooth in biomechanical response data. The method may be conducted by a measurement device and/or computing device. The method includes the identification of the position through which the tooth moves at which the movement occurs most easily, or in other words the change in displacement per unit of force is highest. The force level at which this occurs, can be used to center the raw data of the cyclic movement measurement. The method includes obtaining (320) the raw measurement data (e.g. raw force and position measurement data) and calculating (322) the average displacement curve as a function of the applied stimulus. The method includes calculating (324) the derivative of the displacement with respect to the applied force. The method includes calculating (326) the second order derivative of the measured force-displacement curve. The method includes identifying (328) the point at which this curve is equal to zero, which indicates the force and position at which the tooth is at its neutral position which are selected or identified (330) as an origin around which to center the biomechanical tissue response curve. An example graph including an average displacement curve and derivative curve is illustrated in FIG. 25 and is indicative of the "ease of movement". In other words, the point at which this curve is highest is likely to coincide with the position at which the displacement of the tooth is zero and likewise the compression of tension of the surrounding biomechanical tissue would likely be at its lowest.

In previous examples the user applied a stimulus to the target tooth that followed a cyclic movement and possibly a back and forth or pushing and pulling movement. FIG. 9 is a flow diagram which illustrates another possible use case of the device (102) in which the user can apply a stimulus of random magnitude and random direction. The first step includes attaching (340) the reference jig (if applicable) to the one or more teeth and attaching (342) the attachment mechanism to the target tooth. The user then applies (344) a random force that can vary in magnitude, direction, and frequency and can include six degrees of freedom movement. The force sensor module on the device is configured to measure (345) said randomly applied stimulus and can assign a timestamp to the value measured at a specific time.

Simultaneously, the position sensor module measures (346) the resulting biomechanical tissue response (position measurement data) in real-time and can assign a timestamp to each of the measurement values. In a next step the processor of the device can receive the measurement data from each of the modules and can use the measurement data point at each given timestamp to calculate (348) the behavior curve (or force-displacement curve and the behavior of the PDL resulting from a randomly applied stimulus).

FIG. 10 is a flow diagram which illustrates and example feedback method according to aspects of the present disclosure. The method may be conducted by a measurement device. The feedback method is a process by way of which the user is presented with reference data for the stimulus which should be applied to the target tooth. The feedback may be in real-time and may be based on measurement data (including e.g. a measured biomechanical tissue response) and hence the measured behavior of the PDL. As with previous embodiments, the device and reference jig (if applicable) are attached to the one or more teeth and the tip of the device is attached to the target tooth. The device then provides (360) the user with a signal that indicates that the user can apply a stimulus. This may include outputting reference data (e.g. force reference data) indicating the magnitude, direction and or moments of force that the user is to apply by moving the measurement device relative to the tooth to which it is attached. This feedback can be provided to the user in a number of ways including but not limited to indicator LED's, a screen or user interface on the device or a user interface on an external device (e.g. as described above with reference to FIG. 4A or 4B). In response, the user applies a stimulus according to the reference signal that was provided to the user by the device. The device measures (362) the applied stimulus (force measurement data) and measures (364) the resulting biomechanical tissue response (position measurement data), and calculates (366) the resulting behavior curve (or force-displacement curve). Based on the analysis of the sensor measurement data, the device determines (368) updated reference data and can provide the updated reference data (e.g. as feedback) to the user. This process can be repeated, thereby essentially creating a closed-loop feedback loop and control system that allows a controlled stimulus to be applied to the one or more target teeth.

Aspects of the present disclosure relate to obtaining force measurement data and position measurement data (which together may be termed biomechanical response data) for the purpose of determining one or more determinant points, a target orthodontic force, a stage force value, stage movement value and the like. The data points measured herein may for example be used to define a case-specific critical force level or other appropriate determent point. An optimal force may be a function of the critical force.

Figure 24:
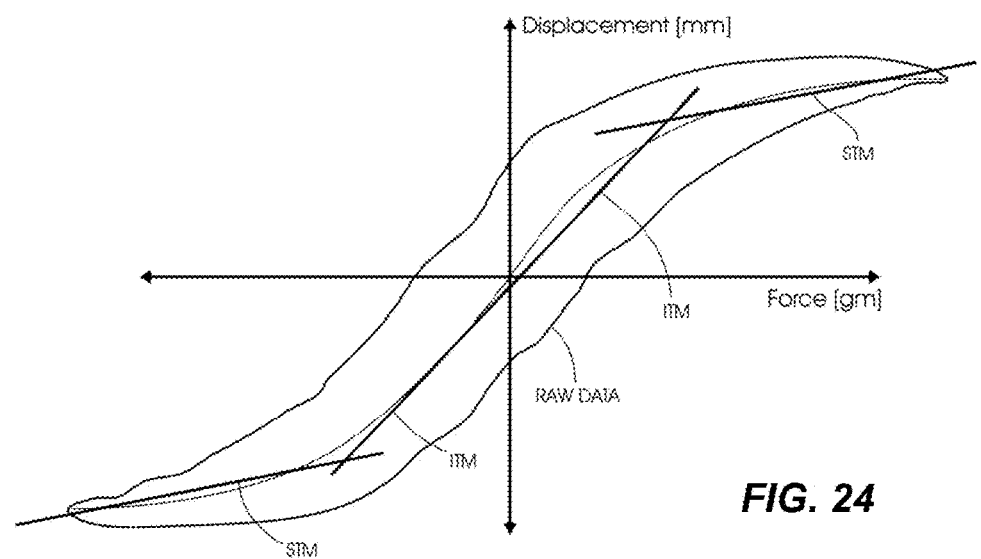
FIG. 24 shows an example of segmented linear regression being applied to the biomechanical tissue response, each line segment representing the initial tooth movement (ITM) and secondary tooth movement (STM), and allowing determinate points on the biomechanical tissue response curve to be defined.

FIG. 11 is a flow diagram which illustrates an example method for determining or calculating a critical force according to aspects of the present disclosure. The flow diagram illustrates one possible process for repeatedly defining determinate points and force levels based on the measured biomechanical tissue response. More specifically, this process allows the definition of a patient, tooth and case specific value of a critical force level Fc to be determined. The method may be conducted by a measurement device or a computing device. The method includes obtaining (380) raw data describing the biomechanical tissue response. This may include receiving measurement data from the measurement modules, retrieving the raw data from the memory module or a computing device receiving the raw data from the measurement device via the communication channel. The method includes calculating (382) the average force-displacement curve (or behavior curve). The method includes applying (384) segmented linear regression to the behavior curve to classify the different regions or stages of non-pathologic tooth movement. An example illustration of this process is also shown in FIG. 24. The segmented linear regression includes (385) fitting straight lines to the behavior curve that describe the initial tooth movement (ITM) and secondary tooth movement (STM) stages of tooth movement resulting from an applied stimulus. When a cyclic movement is applied, the intersection of the ITM stages in opposite directions is fixed at the origin. The method includes determining (386) intersection of the ITM and STM stages in both the forward and backward direction. The method includes identifying (388) the critical force (Fc) as being the force magnitude at the intersection of the ITM and STM. It is at this point that the PDL is partially compressed and this determinate point can therefore be used to identify a critical force level Fc. The method may include storing this value (Fc) in a database in association with one or more of: a patient identifier; tooth identifier; date information; patient health information; treatment regimen information; the raw force measurement data; the raw position measurement data, and the like. The method described above with reference to FIG. 11 includes various steps to define a determinate point on the curve describing the PDL behavior using segmented linear regression.

The measurement systems, methods and devices described herein relate to the measurement of data points and determination of a critical orthodontic force (or simply critical force) using the measured data points. In the description that follows, an overview of the underlying medical and scientific theory is presented together with an explanation of the effects that the various forces applied to target teeth may have on the orofacial structures as well as various outputs that may be obtained using the systems and methods described herein.

FIG. 12 shows a possible tooth displacement resulting from an applied force F. The force F is applied in such a direction that the force does not directly pass through the center of resistance ($C_{RES}$) of the tooth, and thus is expected that the resulting movement will include both a translation as well as a rotational component. These concepts have been studied extensively and are well understood in the field of orthodontics, but in general a force of certain direction and magnitude will result in two components, a translational and a rotational component. The translational component is equal to the direction and magnitude of the force, while the rotational component or resulting moment is a function of the force direction and magnitude as well as the perpendicular distance of the force away from the Centre of Resistance of a tooth. The Figure shows one scenario where the force F is applied at a perpendicular distance away from the Centre of Resistance. The resulting movement of the tooth within the alveolus consists of both a translation and rotation. The overall movement can be described as a pure rotation about the Centre of Rotation (402), which in this case does not coincide with the Centre of Resistance.

The Centre of Resistance (Cres) is a function of the tooth and root shape and morphology, the thickness and the shape of the PDL and other related factors. A shorter tooth root will cause Cres to lie more coronally toward the crown of a tooth, while a longer tooth root will result in Cres lying more apically toward the tip of the tooth root. Similarly, any plurality of tooth roots of an individual tooth or different shapes will affect the position of Cres. FIG. 13 shows the different positions (401, 403, 404) for the Centre of Resistance of different teeth (405, 406, 407).

FIG. 14 illustrates the same force F being applied at different points and in different directions (A, B, C, D, E) on a tooth. Each force will result in a different type of movement of the tooth. The translational component will be the same for all forces except for FE for which the direction differs. The perpendicular distance of FA from Cres is largest for FA. FA will thus have the largest moment applied to the tooth, while FB will have a smaller and FC will have an even smaller moment. The force FD could practically not be applied at the Cres, but in theory would result in a zero moment and only a translational force component. Similarly, the vector of FE passes through Cres and would thus have a translational component only resulting in pure translation of the tooth. While it may not be possible to apply a force such as FD at the Cres of the tooth crown, a force couple can be applied at for example the same point as FB, consisting of a force FB as well as a moment in the opposite direction as the moment resulting from FB. The net force applied to the tooth would then be the same as FD. The current invention is able to calculate the resulting stimulus applied to the one or more teeth based on the force sensor measurement and the position of the applied force in real-time and is able to provide feedback to the user based thereon. In addition, the device is able to provide a reference signal to the user in order to achieve a stimulus that best approximates the desired stimulus applied to the target tooth.

Figure 15:
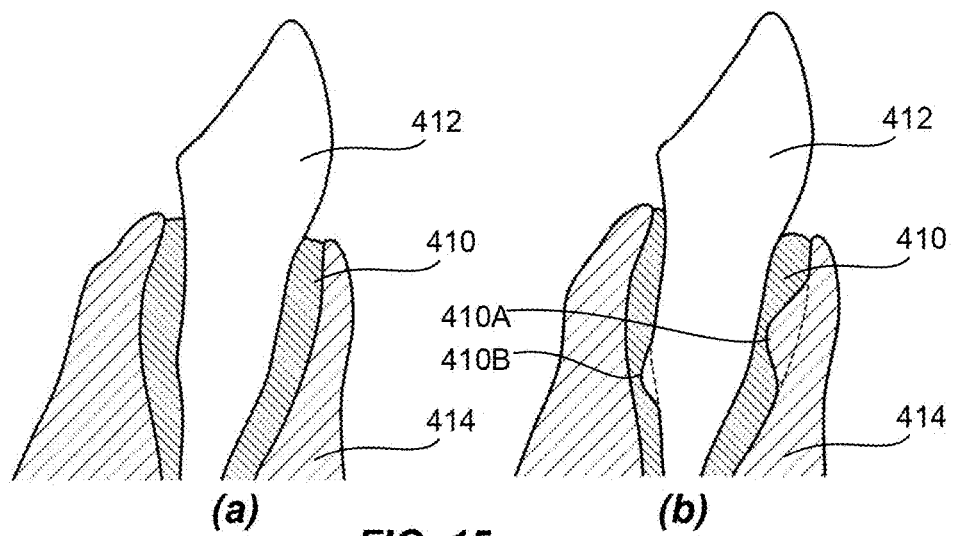
FIG. 15 illustrates side profile views of a tooth showing a non-uniform thickness of the PDL and localized differences in alveolar bone morphology or tooth root morphology.
Figure 23:
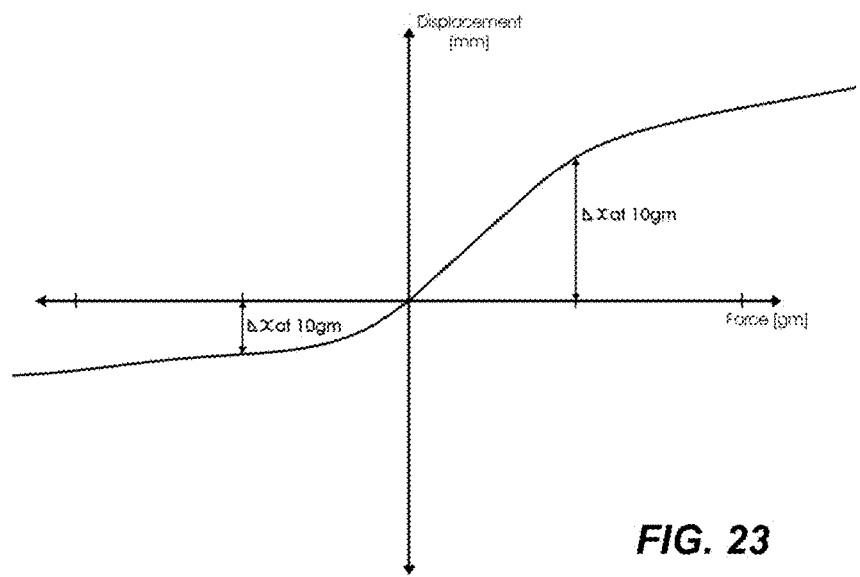
FIG. 23 shows an example of the biomechanical tissue response with a different response for a stimulus in opposing direction.

FIG. 15 (shown as FIG. 15(a) and FIG. 15(b)) is a side profile of a tooth showing the differences that can occur in tooth root and bone morphology. In FIG. 15(a), the PDL (410) shown has a uniform profile and thickness around the tooth (412). FIG. 15(b) shows an example of a tooth that has localized differences (410A, 410B) in PDL thickness due to variations in the tooth root morphology and in the morphology of the alveolar bone (414) structure surrounding the tooth root. The different PDL thicknesses would result in different biomechanical tissue responses when subject to the same stimulus. This difference in behavior of the PDL can be measured and quantified using the current invention. A localized change in shape of either the root or the bone can limit movement of the PDL within the alveolar cavity, thus showing a smaller displacement for a first root or bone morphology as opposed to a larger displacement for a second, different, root or bone morphology resulting from the same applied stimulus. Similarly, differences in the tooth root and alveolar bone morphology, can result to a different biomechanical tissue response in the forward or the backward direction as shown in FIG. 23 where the displacement in the one direction e.g. a pushing force, is larger than the displacement in the opposite direction e.g. a pulling force.

Figure 16:
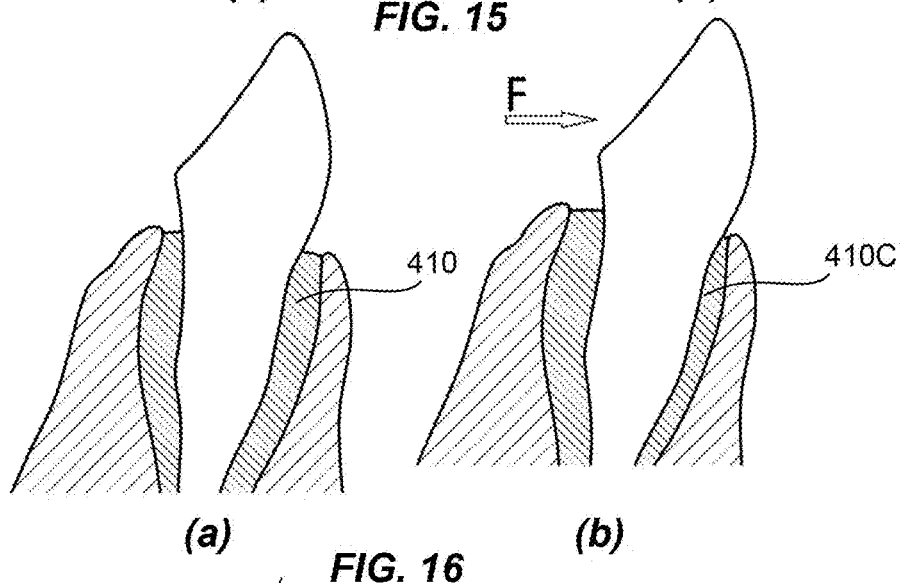
FIG. 16 is a side profile of a tooth in a position before a stimulus has been applied to the tooth and after a stimulus has been applied to the same tooth.

FIG. 16, shown here in FIG. 16(a) and FIG. 16(b) is a side profile of a tooth in a position before a stimulus has been applied to the tooth and after a force (F) has been applied to the tooth. The stimulus or force applied to the tooth causes the PDL (410C) to become compressed as shown in FIG. 16(b). At a lower force, the compression of the PDL is limited by the visco-elastic effects of the PDL which can be measured using the current invention. At a lower force (F) the biomechanical tissue response as a function of the applied force increases faster, while at a higher force (F) the response and displacement of the tooth is limited by the alveolar bone, thus an increase in the applied force (F) does not lead to the same change in the measured tissue response.

Figure 17:
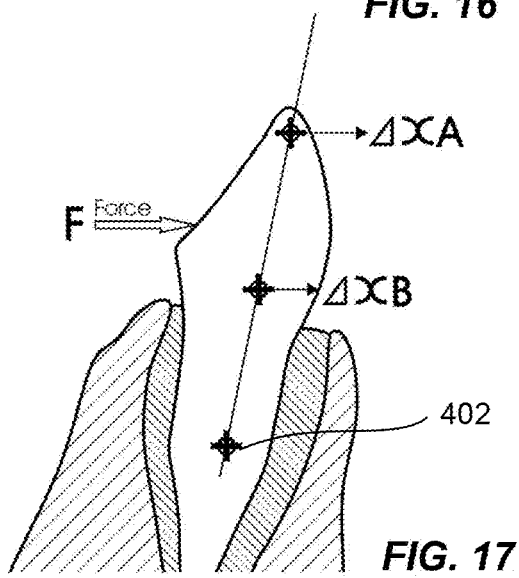
FIG. 17 is a side profile view of a tooth showing different points of measurement, force application and center of rotation on the tooth.

FIG. 17 is a side profile of a tooth showing the points at which a force (F) can be applied and the different points Point A and Point B at which the biomechanical tissue response can be measured. The Figure also shows the Centre of Rotation (Crot) (402) around which the tooth moves. The movement of a tooth when a force is applied to the same tooth can be either pure translation, or pure rotation, or a combination of the two. The movement can further be in all directions including 6 degrees of freedom. In the example shown in FIG. 17, the displacement and movement of the tooth around the Centre of Rotation will result in a higher relative displacement of Point A than for Point B. The device can measure the biomechanical tissue response at either Point A or Pont B or any other point of the tooth or multiple points on the tooth. It is further possible to determine that the movement of Point A and Point B both describe the same biomechanical tissue response, where the one is simply a multiple of the other, assuming that the tooth is rigid or the deformation thereof is negligible.

Figure 18:
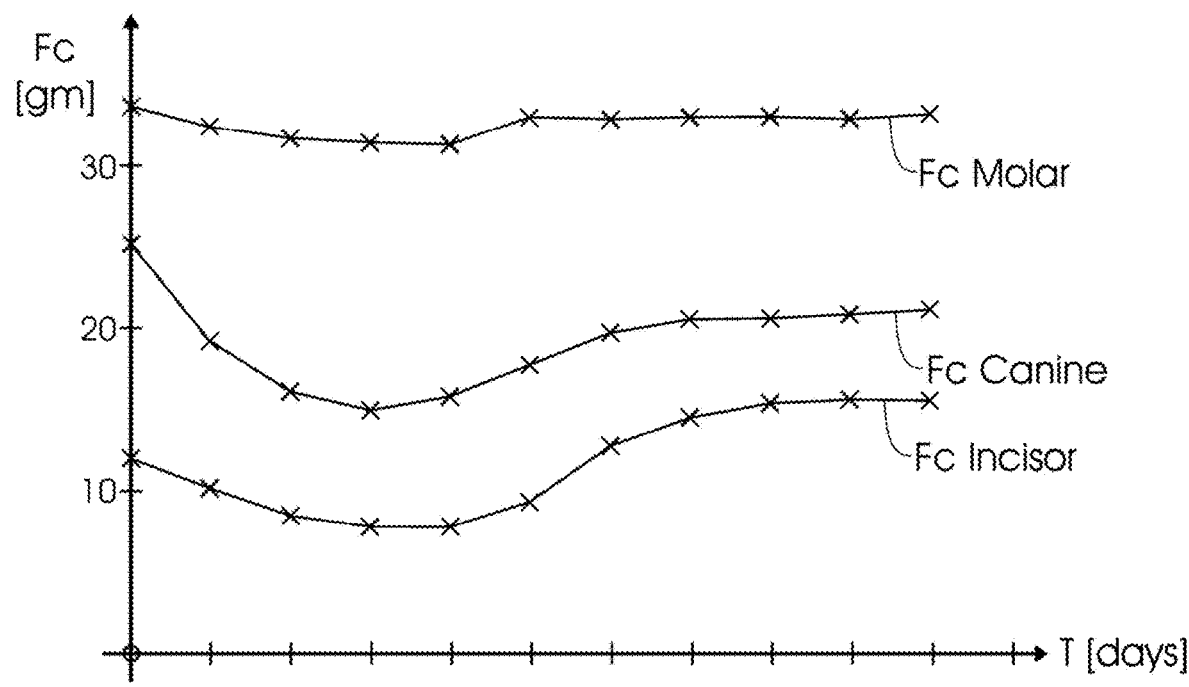
FIG. 18 shows different values of the critical force level Fc determined at different times during orthodontic treatment for three tooth types, a molar tooth, a canine tooth, and an incisor tooth.

FIG. 18 is an example plot of the critical force as a function of time for various different teeth, which illustrates the measured biomechanical tissue response and behavior of the PDL are indicative of the various factors relating to the alveolar complex and the bone remodeling process during orthodontic treatment including, but not limited to tooth and root morphology, PDL thickness, health, and general state of the PDL, bone type, blood pressure, muscular activity, patient age and patient health. Since many of these factors change over time the behavior of the PDL also varies over time and the current invention is able to measure and quantify the biomechanical tissue response to determine this change over time. These changes are especially present during orthodontic treatment during which time significant changes occur to the applied forces and subsequent bone and tissue remodeling. FIG. 18 shows an example of the critical force level Fc as one possible determinate point established at different times during treatment for three different types of teeth. The plotted values of Fc over the course of treatment change due to the changing tissue structures of the PDL during treatment and this change over time can further be different for each individual patient or tooth.

The measurement device described herein is able to measure the stimulus applied by the user as well as the resulting biomechanical tissue (position data) response in real time. For example, the user could apply a force to a tooth in a back and forth motion, alternating between a pushing and a pulling force applied to the tooth. The device would receive a measurement of the applied force at a specific point in time, and the device would also receive a measurement of the resulting tooth displacement at a specific point in time. The processor could assign a timestamp to each of the measurements, allowing these to be received asynchronously. Data can be processed separately or sent to an external device or processor and can be correlated again using the timestamp. By relating the measured stimulus to the resulting tooth displacement, the device would be able to determine the force-displacement curve describing the behavior of the periodontal ligament as shown in FIG. 19A. The raw force-displacement data (416) shows a hysteresis effect due to the visco-elastic effects of the periodontal ligament. The raw data can be used to determine the average biomechanical tissue response for a given stimulus. In the example given, the average force displacement curve (418) can be calculated.

Figure 20:
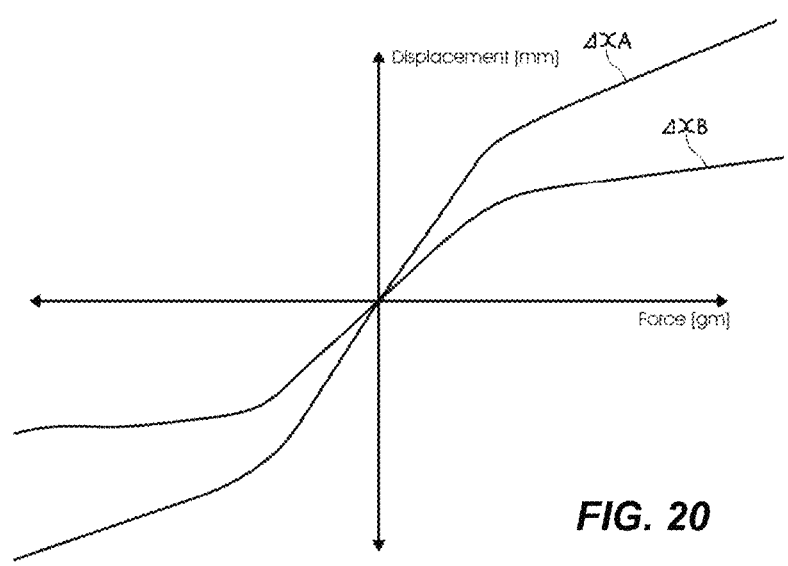
FIG. 20 shows an example of the biomechanical tissue response resulting from an applied stimulus measured at two different points on the tooth.

The measurement device described herein can measure the biomechanical tissue response at different points on the one or more teeth to which a stimulus is being applied. If for example the tooth displacement is measured, this can be different when measured at different points on the tooth and the tooth displacement can include both translation, or rotation, or a combination thereof. FIG. 20 shows an example of the biomechanical tissue response measured at two different points, Points A and Point B (e.g. corresponding to those points illustrated in FIG. 17) on the same tooth, for the case where the tooth movement can include both translation and in this case is rotated around the Centre of Rotation (402). The displacement measured at Point A will be greater than the displacement measured at Point B. More specifically, the displacement of Point A will be a multiple of the displacement of Point B or vice versa. Both curves and measurement at the two points describe the same biomechanical tissue response.

Figure 21:
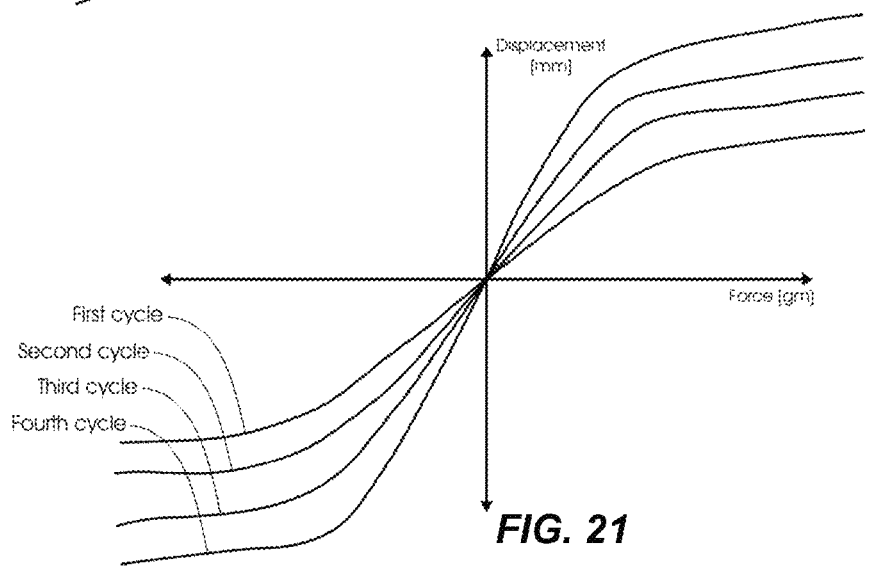
FIG. 21 shows an example of the biomechanical tissue response resulting from a repeated cyclic stimulus applied to a tooth, each cycle leading to an increase in tooth displacement for the same force level.

The force or stimulus applied to the one or more teeth can be applied repeatedly over time and the resulting biomechanical tissue response can be measured. For example, the user can apply a repeated pushing and pulling force to one or more teeth. The measured biomechanical tissue response can vary for each cycle of the applied force, as illustrated in FIG. 21. For example, the displacement of a tooth can increase for each cycle of an applied force due to the visco-elastic effects of the PDL and the biomechanical tissue. The applied pressure can lead to fluids being pushed out of the tissue and lead to compression of the surrounding alveolar bone. Due to the reduced viscous resistance and compression of the surrounding tissue, a greater displacement can be measured for the same level of force that is applied for each subsequent cycle. The device can measure and monitor the change in the biomechanical tissue response over time.

Figure 22:
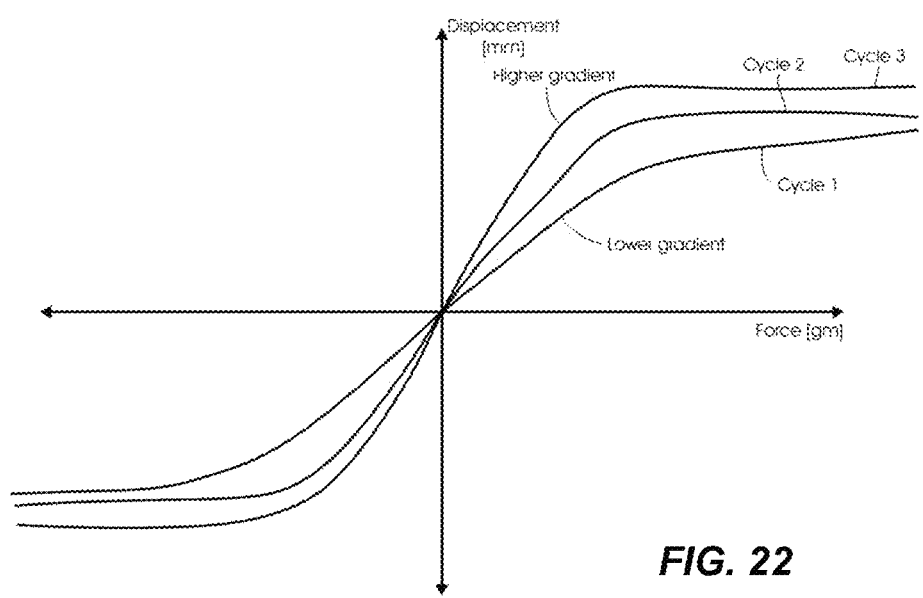
FIG. 22 shows an example of the biomechanical tissue response resulting from a repeated cyclic stimulus applied to a tooth, each cycle showing a different response due to the viscous and fluid effects of the PDL.

FIG. 22 shows another example of the change of the biomechanical tissue response when subject to repeated cyclic stimulus. In this example, the initial response changes more than the tissue response at larger forces. This effect can be seen due to a change in the visco-elastic response of the PDL and surrounding tissue and specifically due to the change in fluid effects. Applying pressure to the PDL can lead to fluids being removed from the tissue, thus leading to a lower resistance on subsequent loading cycles. This change is greater in the initial stage of displacement, where viscous effects are more prominent, and smaller in the secondary stage of tooth movement, where the elastic effects of for example bone compression are greater.

A force or stimulus can be applied to one or more teeth in any direction and in six degrees of freedom. Due to the different shape of the PDL and non-uniform root and bone morphology, the biomechanical tissue response can be different in different directions, as shown in FIG. 23. Here a positive force leads to a larger measured displacement dx, while a negative force or the same magnitude leads to a lower relative displacement.

One example of biomechanical tissue response measured by the current invention can in general be divided into different stages of non-pathological tooth movement. These two stages can be described as the initial tooth movement (ITM) stage and the secondary tooth movement (STM) stage. The ITM occurs at lower forces while the STM stage occurs at greater force levels. One possible way of repeatedly determining these stages of tooth movement is using segmented linear regression, for which a straight line is fitted to the measured force-displacement data describing the biomechanical tissue response the result of which is shown in FIG. 24.

FIG. 25 illustrates another example, in which the measured biomechanical tissue response can be analyzed to determine the direction of the tissue response as well as the magnitude of the tissue response as a function of the applied stimulus. By taking the first and second derivatives of the tooth displacement with respect to the applied force, it is possible to determine for example the ease of movement. This parameter, which is obtained by taking the second order derivative, could be indicative of the force range which would be safe to apply to a tooth or within which no long-lasting negative effects could be expected.

It should be clear from the foregoing that the force magnitude is not the only factor affecting the rate of tooth movement and that various other factors exist that need to be taken into consideration and controlled to induce the maximum rate of tooth movement. The optimal orthodontic force can then be described as the force that, to the best of scientific knowledge, is most effective in producing a desired outcome of a certain orthodontic treatment. This may be the force that, if applied to one or multiple teeth, would result in the maximum rate of tooth movement, while at the same time avoiding any adverse short or long term tissue damage, minimizing patient discomfort or aiding in achieving any other desired outcomes. The force can be in any direction or around any axis in a three-dimensional space and can vary in magnitude, direction, frequency, profile or point of application. The optimal orthodontic force can be patient specific, as well as age or health specific, and can further differ for each tooth, group of teeth, type of tooth movement or other type of treatment.

The use of new orthodontic appliances such as clear aligners, robotically bent arch wires or 3D printed orthodontic appliances and components has provided new opportunities for controlling the amount of tooth movement and the forces applied to one or more teeth. The ability of 3D printing orthodontic and dental appliances or parts thereof allows highly accurate control of the shape and functionality of the appliance. For example, the exact forces of an orthodontic appliance could be controlled by 3D printing by means of controlling the material type, stiffness, and geometry at a micron level. Similarly, the exact forces applied by an orthodontic arch wire can be controlled using robotically bent and custom formed arch wires. While this technology provides a significant improvement over conventional orthodontic systems, it can still lead to orthodontic appliances that transmit forces to the teeth which are higher than the optimal forces levels and thus can lead to the negative effects including discomfort, tissue necrosis or root resorption. The measurement data obtained from the measurement device described herein may be applied in the determination of a patient-, tooth-, health-, time- and/or treatment regimen-specific target force for use in the configuration and manufacture of such aligners.

Aspects of the present disclosure provide a device configured to quantify the biomechanical tissue response and behavior of the PDL in-vivo (e.g. by obtaining force and/or measurement data). The measurement device may for example include; an attachment mechanism allowing a user to apply and transfer a stimulus to one or more teeth; a feedback system including at least one sensor configured to measure the stimulus applied to one or more teeth; a feedback system including at least one sensor configured to measure parameters relating to the biomechanical tissue response (e.g. changes in position data) resulting from the applied stimulus; a power source configured to provide power to the device; a processor in data communication with the sensors, said processor being able to measure, process and analyze the signals received from the sensors; and, a feedback mechanism in the form of a general user interface or indicator lights.

Aspects of the present disclosure provide a measurement device for measuring and quantifying the biomechanical tissue response and relating behavior of the PDL and surrounding tissue in-vivo. The device includes a sensor system configured to measure the stimulus applied to the one or more teeth using a six degrees of freedom force sensor system. In some embodiments, the sensor system is configured to measure the biomechanical tissue response using magnetic hall sensors to measure the resulting biomechanical tissue response of one or more teeth. In other embodiments, the sensor system is configured to measure the biomechanical tissue response using a camera to measure the resulting biomechanical tissue response of one or more teeth. In some embodiments the sensor system is configured to measure the biomechanical tissue response using computer vision to determine the position of certain points on one or more teeth and to measure the resulting biomechanical tissue response. This may include using computer vision to calculate the position of the tooth in 3D. The device may be configured to provide feedback to the user regarding the desired stimulus to be applied.

Aspects of the present disclosure provide a method for determining and quantifying the behavior of the periodontal ligament. The method includes using a measurement device to apply a stimulus that includes cyclic forces, measuring the tissue response of one or more teeth for each back and forth cycle, and quantifying and determining points on the curve describing the PDL behavior Aspects of the present disclosure provide a device for quantifying the behavior of the PDL and measuring the biomechanical tissue response resulting from an applied stimulus. The device includes a means for creating an attachment to one or more teeth and for transmitting a stimulus such as a force to the tooth. The device further includes a rod allowing a stimulus to be transferred from the handle of the device to the tooth. The device includes an ergonomically shaped handle for the user to hold the device and can include indicator lights or LED's, an LED or LCD screen to provide feedback to the user. The device can also include a sensor system to measure the biomechanical tissue response.

Optimal Force Engine

Above, reference is made to a target orthodontic force which is said to be an optimal force or optimal orthodontic force.

An Evidence-Based Approach

Previous research on an optimal force has focused primarily on the relationship between the force magnitude and the resulting tooth movement. This relationship was expressed mathematically as $$x = f(F) \quad \text{(Equation 1)}$$

and is based on the general assumption that a quantitative relationship can indeed be determined. Equation 1 describes the tooth movement as a function of a single input parameter, namely force F. This relationship disregards several of the relevant factors relating to orthodontic tooth movement, however, and therefore is unlikely to be able to fully and accurately describe such a complex relationship. In contrast, there are many different factors that have been shown to affect the resulting tooth movement. If these additional parameters are taken into account this would be expressed mathematically in the form:

$$x = f(p_0, p_1, p_2, \ldots, p_n) \quad \text{(Equation 2)}$$

where x is the resulting orthodontic tooth movement and $p_0$, $p_1$, $p_2 \ldots p_0$ are all parameters that to some extent affect said tooth movement.

Equation 2 thus takes into account all relevant parameters, but is difficult to solve because too many variables remain unknown. The choice of suitable variables is critical and can be narrowed down by considering (a) the controllability of input parameters and (b) the measurability and quality of output parameters.

Only a number of input variables are directly controllable and can be altered by the researcher or practitioner (i.e. "Controllable Factors" e.g. including static force magnitude, direction, duration, point of application and frequency of application as well as the amplitude, frequency and profile of a dynamic force). Earlier factors (e.g. time<0 factors) are part of the biological system and cannot be controlled, while later factors (e.g. time>0 factors) are in some way a function of the applied force F, and therefore can, to some extent, be controlled.

Various output variables can be used to measure tooth movement, but the attainable quality thereof often seems to be a decisive factor. Data quality can be gauged in terms of:
  Accuracy
  Frequency (how often is data obtained)
  Timing (when data is first obtained e.g. after t=1 sec, 1 day or 1 week)
  Relationship to input parameter (data are directly or indirectly related to F)
  Robustness (data are susceptible to variations of measuring method, type of tooth movement, individual differences, time of sampling).

When reviewing the available literature, the above factors seem to have governed the success or failure of many a study. The availability and accuracy of data were identified as key concerns, as well as large individual variations, the timing of measurements with regard to the different stages of tooth movement, variations in species and controlling the type of tooth movement[2,7,8].

Past Study Methods and their Limitations

Studies have frequently not been able to reach conclusive results and have listed a lack of statistically significant data, insufficient device capabilities and study methods as reasons. The following section will discuss some of the available research methods and the relating challenges faced by researchers.

In-vivo studies are attractive in that no compromise is made in terms of the accuracy of the system being examined. The affected tissues are in their true state and the biological system retains its all-important properties that might affect orthodontic tooth movement. Yet, the accuracy to which forces can be applied to individual teeth in-vivo is often limited by appliance capabilities. The mechanical nature of conventional appliances often does not provide the desired feedback and control over the applied stimulus, which in turn affects the type of tooth movement.

The use of electronic test set-ups in-vivo has also been previously described[9-11]. These allow for improved data collection, but are often limited by practical applications. Electronic appliances, measuring devices or experimental set-ups are often only suitable for laboratory environments and require physical connections such as cables to a computer for data collection. This makes repeated measurements harder and limits the attainable sampling frequency during treatment.

In-vitro studies on the other hand allow for sophisticated test set-ups and therefore improved means for data collection. The use of accurate measuring equipment enables characterizing the response of the PDL when subjected to various force stimuli[12-13]. In-vitro experiments are unfortunately limited by the extent to which the tissue response of specimens resembles the true biological system response.

Developing mathematical models offers interesting insights and presents itself as an attractive solution to define an optimal force. As previously discussed, however, these rely heavily on the availability of data and its accuracy. Further, accounting for multiple variables requires increasingly complex models, while simplifying models compromises in accuracy by assuming the effect of certain parameters to be negligible. Ren et al.[1] noted for example that when co-variables such as reactivation or type of appliance were taken into account, the variance of their model increased significantly. Such a model is thus sensitive to uncertainties or unknown parameters and does not offer robustness.

The use of finite element methods (FEM) for orthodontic studies has provided great insight to patterns of stress distribution in the PDL, tooth mobility, and also the time dependent changes incurred after the application of a force[14,15]. It can further account for different tooth and root geometries and different material properties. Preparation of FEM models often requires CT scans[14] as well as defining numerous material properties, which play a critical role in the analysis. Assumptions need to be made regarding said material properties and accurately defining these remains a challenge[16].

The material properties of the PDL have for example frequently been assumed to be linear elastic, homogeneous, and isotropic[14] even though data indicates that the morphology of the PDL is highly inhomogeneous[3]. Such simplifications cause the validity and reliability of FEM to be questioned[17]. Current FEM models are also not well suited to accurately account for the time-dependent short and long term changes seen in the PDL.

Generally, all of the prior methods for investigating the concept of an orthodontic force have limitations and have led several researchers to conclude that improved technologies and methods are required. The multitude of factors relating to orthodontic tooth movement and their interdependent nature make it impossible to isolate single variables. Without further discussion hereof, it is unlikely that all such variables and unknown parameters can be accounted for in an effort to determine a quantitative relationship.

Observations

When collectively reviewing the available literature concerned with an optimal orthodontic force, several factors which play a fundamental role in conducting orthodontic research can be observed.

Observation No. 1—Risks of Quantitative Solutions

The general prior art approach to defining an optimal orthodontic force has been of a purely quantitative nature. Exact numerical values of variables have been used with the aim of determining statistically significant solutions and mathematical models. As discussed, these do not offer robustness to variations and do not account for the many unknowns of the biological system under investigation that researchers seem to acknowledge exist.

Observation No. 2—Non-Pathologic Tooth Mobility

The intra-alveolar displacement of a tooth is usually referred to as tooth mobility and is more frequently related to periodontics. Tooth mobility is also observable for a healthy tooth and is a function of the bio-physical parameters of the healthy periodontal environment. It represents the intra-alveolar displacement of a single tooth due to an applied force. Notably, non-pathologic tooth mobility is the only factor which is:

measurable in-vivo
measurable within seconds
measurable without causing any damage to the affected tissues
measurable by external means and without sacrificing the subject
measurable repeatedly and dynamically.

There are also two clearly distinguishable stages of tooth mobility, namely initial tooth mobility (ITM) and secondary tooth mobility (STM) as first described by Mühlemann[18]. ITM is generally perceived as being facilitated by the visco-elastic properties of the PDL, while STM is considered the result of an elastic deformation of the alveolar socket walls[12,18].

Observation No. 3—Force Magnitude

When considering previous studies on humans very few have accurately investigated the effect of low forces of 30 cN or less. The majority of studies listed in previous reviews by Owmann-Moll et al.[6], Ren et al.[7] or Von Böhl et al.[19] have examined forces that lie in the range of 50 cN to 200 cN, with some as high as 1500 cN.

Observation No. 4—Light Orthodontic Forces

Even though references to light orthodontic forces or comparisons between light and heavy forces can repeatedly be found, there exists no clear definition as to what constitutes a light force.

The term can refer to forces ranging from 1 cN to 60 cN, while if two forces are compared, even 300 cN can be referred to as light in comparison to a second larger force[5]. Despite its frequent use, there is no universal consensus nor sound scientific evidence regarding the force magnitude[7]. Any reference to a light force requires a threshold, a maximum value or reference point by which it can be gauged.

A New Paradigm

Non-pathologic tooth mobility can be measured as a function of an applied force and represented as a curve which has been measured since the 1950s. The validity of this curve has been confirmed by several studies and simulations[18,20-23]. Tooth mobility further represents the only externally measurable variable immediately after the application of a force and before any significant tissue remodeling has taken place. It is thus one of the most important and yet disregarded factors relating the applied force to orthodontic tooth movement.

Tooth mobility can be regarded as an intermediate variable when relating an applied force to orthodontic tooth movement. The shape of the curve is directly dependent on the majority of factors relating to the biological system as well as those of the applied force. It is a function of the root geometry and morphology of the PDL and surrounding alveolar structures. It is also a function of the force magnitude, the force direction and the rate of force application.

In contrast to the previously discussed models, characterizing the tooth mobility curve does not require any knowledge of the variables by which it is affected. Instead, it can be measured as was already done over 50 years ago by Mülemann[18]. The resulting numerical value of the maximum displacement in μm is also not critical. Instead, the ability to determine the shape of the tooth mobility curve is critical. The shape allows the ITM and STM force ranges to be identified, thereby providing valuable insight into the extent of PDL compression.

This argument is based on the typical curve that is observed when the soft PDL is deformed either by compression or tension as described in detail by Sanctuary et al.[12]. In both cases the change in displacement (often expressed as strain) per change in force is highest close to a force of zero magnitude and decreases at higher forces[4]. The steeper ITM gradient for lower forces and a decreased gradient for STM at higher forces is also in agreement with the argument that low forces will induce an intra-alveolar displacement of the root, while forces exceeding the ITM range will displace both the PDL and the surrounding alveolar bone[20,14].

Based on the above, the hypothesis is put forth that the force magnitude at which the transition from ITM to STM occurs corresponds to a critical force Fc at which the PDL has, at least at one location, been fully compressed.

Because the shape of the tooth mobility curve depends on all relevant factors affecting tooth movement at the time of force application (time=0), the value of Fc is automatically also a function thereof. This is expressed mathematically in the form:

$$F_C = f(\text{force magnitude, type of movement, point of application, root geometry, PDL morphology, blood pressure, species, patient age, etc.}) \quad \text{(Equation 3)}$$

where $F_C$ is the critical force value in grams and all variables of function $f$ in some way affect the shape of the measured tooth mobility curve. It is thus suggested that orthodontic tooth movement should be considered a function of Fc rather than a function of the initial variables affecting Fc. Equation 1 then becomes:

$$x = f(F_C) \quad \text{(Equation 4)}$$

where the value of $F_C$ is completely case specific. For example Fc for each of a Minipig, rat and human may be as follows:

$$F_C = f(\text{Minipig, Molar, Translation, Rotation}) \approx 25 \text{ cN}$$

$$F_C = f(\text{Rat, Molar, Translation, Rotation}) \approx 0.5 \text{ cN}$$

$$F_C = f(\text{Human, Incisor, Intrusion}) \approx 50 \text{ cN}$$

$$F_C = f(\text{Human, Molar, Translation, Tipping}) \approx 13 \text{ cN}$$

Even though these values are approximate and for illustration purposes only, the above examples show that the value of $F_C$ is case and tooth specific. The value for the human cases for example is significantly higher than that of the rat, while the value of $F_C$ within the same species human is higher for intrusion than it is for the translation/tipping movement. It should be noted that the value of $F_C$ could in itself be dynamic as it is influenced by blood pressure, remodeling of the PDL and its surrounding structures and other time-dependent biological processes. The critical force $F_C$ is not an abstract mathematical parameter but is related directly to physical phenomenon. Any force with a magnitude exceeding $F_C$ is likely to have a significantly different effect on the tissue remodeling than a force of a magnitude below $F_C$. The measurement and definition of such case specific values of $F_C$ could provide a key reference for the future investigation of an optimal orthodontic force and orthodontic treatment in general. In this paradigm, force magnitude alone is no longer the only critical component but rather the force magnitude expressed in terms of $F_C$. Further, the definition of $F_C$ would provide a reference by which to define light orthodontic forces. A light orthodontic force could be defined as a force of which the magnitude is smaller than Fc. Once the value of $F_C$ has been determined it, or a force with reference to $F_C$, can be related to the orthodontic tooth movement as described by Equation 4.

Figure 29:
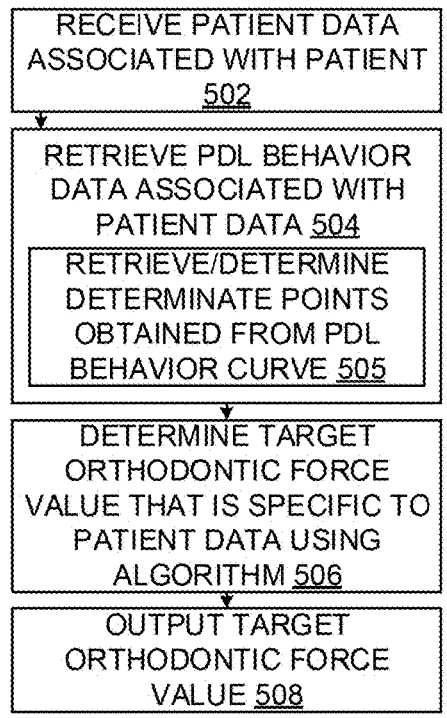
FIG. 29 is a flow diagram which illustrates an example method for determining a target orthodontic force according to aspects of the present disclosure.

With this evidence-based approach in mind, the optimal force engine (25) described above with reference to FIG. 1A may be configured to perform or conduct a methods for determining a target orthodontic force that can be said to be the optimal orthodontic force. The optimal force engine (25) may be configured to define a target or optimal force based on or as a function of one or more determinate points of PDL behavior data (9). One example embodiment of a method for determining a target orthodontic force is described below with reference to FIG. 29. The method may be conducted by a suitable computing device which in some embodiments may form a part of or may provide an optimal force engine.

The method includes receiving (502) patient data associated with a patient. The patient data may include patient characteristic data and patient treatment data. The patient characteristic data may for example include data points relating to one or more of physiological, biological, genetic and situational characteristics of the patient. The patient treatment data may include data points relating to patient condition and treatment requirements, including for example one or both of a tooth type indicator and a tooth position indicator associated with a tooth of the patient to be corrected. The patient treatment data may also include treatment movement data (e.g. including one or more treatment movement values) which describes the required tooth movement to effect treatment (or correction) of the tooth.

The method includes retrieving (504) PDL behavior data associated with at least a subset of the patient data. The PDL behavior data includes or is based on measurement data including force measurement data points and corresponding displacement measurement data points having been measured in-vivo while applying a force to a tooth of a human or animal subject (e.g. using a measuring system as described in the foregoing or other suitable means).

The PDL behavior data may include one or both of measured PDL behavior data and modelled PDL behavior data which is based on force measurement data points and corresponding displacement measurement data points having been measured in-vivo while applying a force to a tooth of a human or animal subject. In some cases, for example, retrieving the PDL data may include querying a datastore (7) for data (including e.g. modelled and/or measured PDL behavior data) that is associated with the patient data or a subset thereof. In other cases, retrieving the PDL data may include using a PDL behavior model (33) to model or generate data that is associated with the patient data or a subset thereof. In other cases, the data may be retrieved from an interface module (23) or otherwise made available to the optimal force engine. The PDL behavior data may therefore include or be based on historical PDL behavior curves determined based on measurements of other humans. The PDL behavior data can therefore include one or both of data points measured from another human and data points determined by a model that is trained based on data points measured from another human. The PDL behavior data includes or is based on externally measurable data points, which may facilitate or simplify the collection of large-scale datasets by virtue of the data being more easily obtainable (e.g. using a measurement system as described in the foregoing). In some implementations, retrieving the PDL behavior data includes retrieving raw data describing the PDL behavior curve consisting of the measurement of the applied force and the measured resulting tooth displacement.

Referring to FIG. 19A, an example visualization of data describing the PDL behavior which can be received in real time or retrieved from memory (such as a datastore) is shown for one of six possible degrees of freedom. The data describes the behavior of the PDL when it is subjected to an applied force, in this case to a back and forth motion, and includes both the magnitude of the force and the displacement as well as the direction of the force and the displacement (e.g. forward or backward or clockwise or anticlockwise) for the relevant degrees of freedom. The data could also vary depending on any other variables in the stimulus that have been applied to the one or more teeth. For example, the measurement data can include time dependent factors such as frequency, or duration of application, and the data can typically include time data to describe the moment in time when each of the data points was measured, recorded or received by a processor. The data shown in the Figure can describe the behavior of the PDL when subject to a stimulus and all measurable variables such as also the visco-elastic effects, relating hysteresis, and any time dependent compression or tension or any other movement of the PDL.

Referring to FIG. 19B, another example of the raw measured data describing the behavior of the PDL is shown. The data shown is for a specific patient and a specific tooth and in this example is measured for repeated cyclic back and forth motion of the tooth. The data shows 16 consecutive back and forth movements denoted by C1, C2, . . . , C16, and the same can be measured for any number of cycles of movements. The data in the Figure also shows the change in the shape of the curve and more specifically the increased displacement at the same force applied. Aspects of the present disclosure can use such raw measured data of the PDL to determine a critical force level and to determine the relating optimal orthodontic force.

Referring to FIG. 19C, another example of the raw measured data is shown. In this case the data includes more noise, but allows for the same information describing the PDL behavior to be extracted. Various means for data filtering, normalizing, averaging or any other data processing can be applied to the raw measured data.

Returning to FIG. 29, retrieving (504) PDL behavior data may include retrieving or determining (505) one or more determinate points or ranges from the PDL behavior data associated with the patient data or a subset thereof. In some cases, the PDL behavior data may be in the form of a PDL behavior curve and the determinate points or ranges may be obtained from the PDL behavior curve. In other cases, the PDL behavior data may be obtained from a PDL behavior model (33) and determining the determinate points may include using the model to determine these points. Each of the one or more determinate points includes a component for each of six degrees of freedom of movement (e.g. translation and rotation about each of x-, y- and z-axis). Different mathematical or statistical approaches can be used to determine a determinate range or point on the PDL behavior curve. In one example embodiment, the critical force level Fc is calculated. As described in the foregoing, this can be done by using segmented linear regression for example and identifying the force at which the ITM (initial tooth movement) changes to STM (secondary tooth movement) or in other words, the force at which the PDL is compressed to a certain extent. Thus, in some implementations, the one or more determinate points include a critical force value. In other implementations, other determinate points may be used. The PDL behavior data may thus include a reference point that reflects the physiological, biological, genetic and/or situational characteristics of the patient (by virtue of the association with patient data), in particular of the patient's PDL. In other words, the reference point is one that describes a force that will produce a comparable effect on the alveolar structures for any patient (but which force will be different for different patients with different physiological, biological, genetic and situational characteristics or properties). This allows for comparison of treatment plans and results across different patients in a manner that acknowledges or accommodates the fact that different patients and different teeth have different properties that result in different PDL behaviors. For example, referring to the table below in which the critical force is used as the determinate point, it can be seen that by using a determinate point such as the critical force as a reference point allows for a comparison across teeth and/or species (or patients) in terms of which the effect of the force on the alveolar structures is compared. This is in contrast to comparing the absolute value of the applied force as has hitherto been the conventional approach and which is meaningless given the vastly different effect that will result on the alveolar structures if the same force is applied to different teeth, different species or different patients.

TABLE 1

| Case-specific study details | | | | Applied force Conventional approach | Applied force Evidence-based approach |
|---|---|---|---|---|---|
| Species | Tooth | Direction | Fc(g) | | |
| Rat | Molar | Translation | 0.50 | 25 g = 50 × Fc | 0.5 g = 1 × Fc |
| Human | Incisor | Intrusion | 50 | 25 g = 0.5 × Fc | 50 g = 1 × Fc |
| Minipig | Molar | Translation | 25 | 25 g = 1 × Fc | 25 g = 1 × Fc |
| Human | Incisor | Tipping | 12.5 | 25 g = 2 × Fc | 12.5 g = 1 × Fc |

Referring to FIG. 24, and as described in the foregoing, an example determination of determinate points according to aspects of the present disclosure is illustrated. A biomechanical tissue response plot measured in accordance with aspects of the present disclosure can in general be divided into different stages of non-pathological tooth movement. These two stages can be described as the initial tooth movement (ITM) stage and the secondary tooth movement (STM) stage. The ITM occurs at lower forces while the STM stage occurs at greater force levels. One possible way of repeatedly determining these stages of tooth movement is using segmented linear regression, for which a straight line is fitted to the measured force-displacement data describing the biomechanical tissue response the result of which is shown in FIG. 24. In another example shown in FIG. 25, the measured biomechanical tissue response can be analyzed to determine the direction of the tissue response as well as the magnitude of the tissue response as a function of the applied stimulus. By taking the first and second derivatives of the tooth displacement with respect to the applied force, it is possible to determine for example the ease of movement. This parameter which is obtained by taking the first order derivative could be indicative of the force range which would be safe to apply to a tooth or within which no long-lasting negative effects could be expected.

Returning to FIG. 29, the method includes determining (506) a target orthodontic force value that is specific to the patient data by inputting the PDL behavior data (which may be the determinate point(s) obtained from the PDL behavior data) into an algorithm which determines the target orthodontic force based on the PDL behavior data. The algorithm includes one or more of time, magnitude, case, patient (e.g. including patient characteristic and patient treatment) components and the like. The algorithm may for example be expressed as an equation with a variable for each of the one or more time, magnitude, patient characteristic and patient treatment components as well as for the relevant determinate point(s). The patient treatment component may for example include variables for one or more values representing one or both of desired patient treatment outcome and patient treatment objective (e.g., as defined by treatment movement data). Determining the target orthodontic force value may therefore include defining the target orthodontic force value as being a function of the one or more determinate points or ranges of the PDL behavior data (such as a critical force Fc value). The algorithm, or function, may be any suitable binary relation over a first (target orthodontic force) set and a second (determinate point) set that associates to every element of the first set exactly one element of the second set. In other words, the algorithm sets how the target orthodontic force value depends on the determinate point. The algorithm can be a linear or polynomial function, or any other relationship between the target orthodontic force value and the determinate point(s), so that the target orthodontic force is defined as, in the case of the critical force value being the determinate point:

$F \text{target} = f(Fc)$

It should however be noted that Fc can be replaced by any other repeatedly identifiable point, or range on the PDL behavior curve. For example a determinate point could be defined at the neutral position of the curve, at a point at which the curve reaches a certain gradient, or change of position as a function of the applied force, the point at which a certain percentage of the maximum measured force or displacement is reached, an area, range or point at which the area under the curve reaches a certain value or any other definition with relation to the measured PDL behavior curve.

The method includes outputting (508) the target orthodontic force value. The target orthodontic force value may be output for retrieval by one or more of: a point of care system (5); a treatment plan engine (41); an appliance configuration engine (43) and an interface module (23) (e.g. for retrieval by any other system that might need the target orthodontic force). The target orthodontic force value may be output for use in effecting correction of the tooth of the patient (e.g. by formulating a treatment plan and/or configuring an orthodontic appliance to apply or exert the target orthodontic force). The target orthodontic force value may for example be output to an appliance configuration engine (43) configured to use the target orthodontic force value to configure one or more parameters of an orthodontic appliance such that an orthodontic appliance manufactured or otherwise produced in accordance with the configuration applies the target orthodontic force to the tooth of the particular patient. The target orthodontic force is a measurable value that can be compared to other forces for evidence-based treatment of orthodontic conditions. The target orthodontic force is based on externally measurable parameters (i.e., the determinate points of the PDL behavior data). Specification of treatment plans and/or orthodontic appliances based on a target orthodontic force allows for a force-based approach to orthodontic treatment as opposed to purely spatial-based approach.

Figure 30:
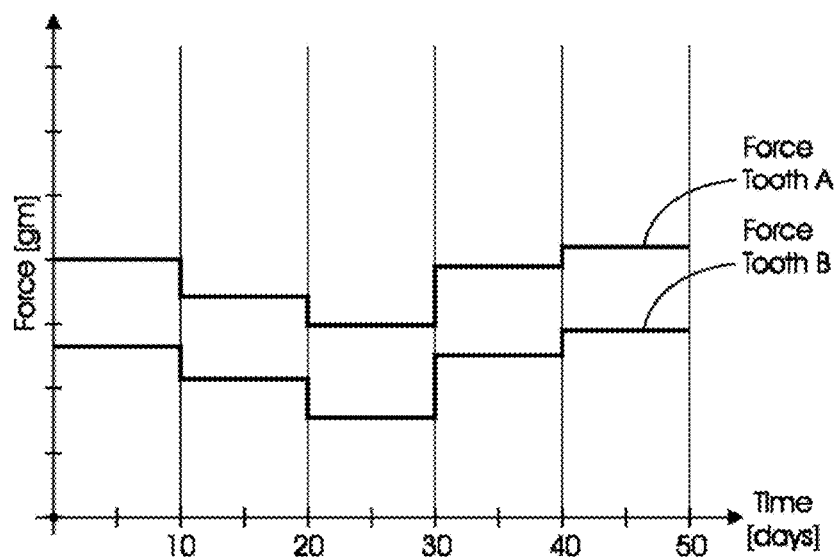
FIG. 30 shows time-dependent target orthodontic force values for each of a series of appliances for two different teeth.

Referring to FIG. 30, an example target orthodontic force, also referred to as an optimal orthodontic force, as a function of Fc that varies with time is illustrated. The optimal orthodontic force can take into account the time-dependent changes in the critical force level Fc, which changes over time and specifically throughout the duration of orthodontic tooth movement, and can be a function of time so that $Fopt = f(Fc, t)$ and $Fc = f(case, t)$ $Fopt = f(F(case, t), t)$ In FIG. 30, an optimal force Fopt is shown for a series of different orthodontic appliances worn during treatment. This can be a series of arch wires, elastic or orthodontic aligners, for each of which an optimal orthodontic force is determined. The first appliance has a higher Fopt for example to initiate tooth movement, while the second and third appliances have a lower Fopt so as to reduce the pressure on the PDL and alveolar tissue which is undergoing remodeling to facilitate tooth movement. Towards the end of treatment Fopt for each of a series of appliances is increased again as a patient becomes more accustomed to the forces for example. The time dependent profile and optimal orthodontic force for each appliance can take on any profile that varies over time. In addition, FIG. 30 shows a time-dependent optimal orthodontic force for each of a series of appliances for two different teeth, Tooth A and Tooth B. Similarly, Fopt can vary for any case specific factors including one or more of patient age, gender, tooth, or group of teeth, treatment movement data, force magnitude and direction of force and the like.

Figure 31:
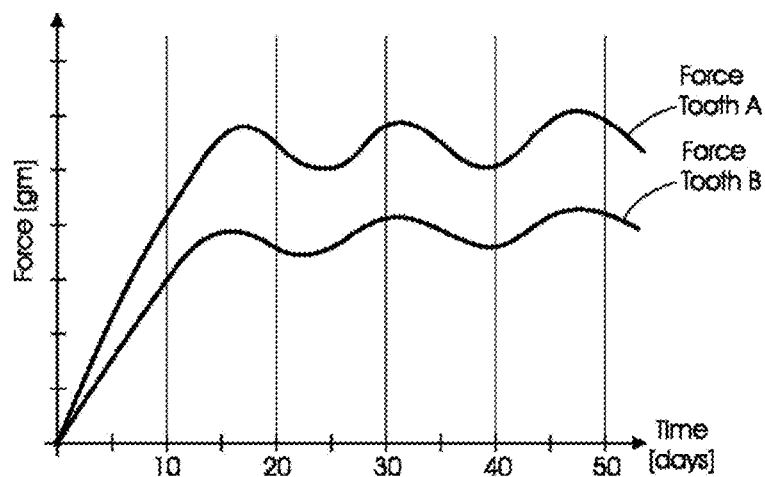
FIG. 31 shows a continuous definition of target orthodontic force values according to aspects of the present disclosure.

FIG. 31 shows another example optimal orthodontic force Fopt as a function of time. While FIG. 30 showed an optimal orthodontic force for each of a series of orthodontic appliances, FIG. 31 shows a continuous definition of Fopt. As described above, Fopt can be defined using an algorithm (which may e.g. be a mathematical model, artificial intelligence, or any computer based model) to define such a time and case specific function for Fopt. This graph can be determined for a specific individual or group of individuals and can be based on, but not limited to, measurements of the PDL behavior curve, patient feedback, or treatment outcomes.

The method may include updating the algorithm using feedback data (15) including one or more of: test rig feedback data points, patient feedback data points and treatment feedback data points. The feedback data is obtained during use or testing of an orthodontic appliance configured to apply the target orthodontic force. The feedback data may for example be based on or include rate of change data points measured while using the orthodontic appliance. The algorithm may be updated if it is not stored or otherwise identifiable as an optimal algorithm. Updating the algorithm may include iteratively updating the algorithm to optimize the feedback data to determine an optimized algorithm for determining the target orthodontic force (which would then be an "optimal orthodontic force"). Iteratively updating the algorithm until it is optimized means that it can be said that the target orthodontic force determined using the optimized algorithm becomes the optimal orthodontic force as it is one that when applied by an orthodontic appliance optimizes a balance of patient comfort and treatment outcome, for example.

Figure 32:
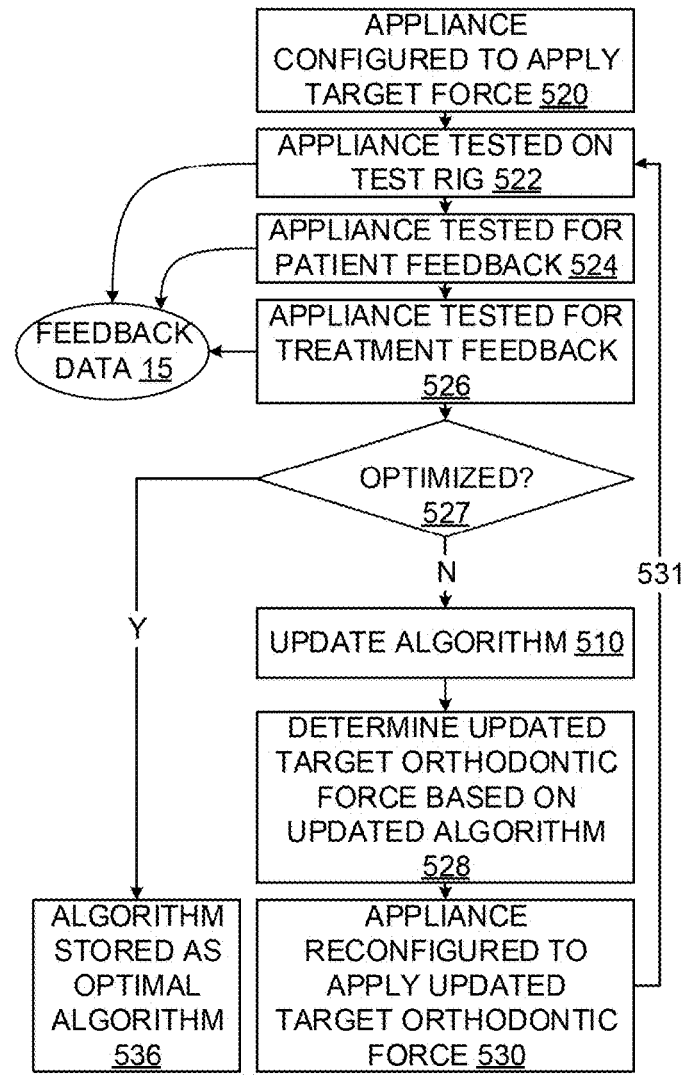
FIG. 32 is a flow diagram which illustrates an example method for updating an algorithm using feedback data according to aspects of the present disclosure.

For example, referring now to FIG. 32, updating the algorithm using feedback data may include configuring (520) an orthodontic appliance to apply the target orthodontic force (this may include using an appliance configuration engine and inputting into the appliance configuration engine the target orthodontic force). This may be preceded by determining or creating a treatment plan based on the target orthodontic force (e.g. using a treatment plan engine). The orthodontic appliance may then be tested (522) on a test rig to compare the target orthodontic force against the actual force applied by the appliance. Feedback data points from the test rig, including for example the extent to which the actual force matches the target orthodontic force, are collected into feedback data (15). Feedback data for testing an orthodontic appliance can include force data including six degrees of freedom and can also be time dependent. Further feedback data can include displacement data for testing the orthodontic appliance and the displacement data can also be time dependent. Feedback data can further include both force and displacement data at one or more points in time and can be for a single tooth or a group of teeth. The orthodontic appliance may then be tested (524) for patient feedback, for example by fitting the orthodontic appliance to the relevant tooth or teeth of the patient and collecting patient feedback data points for inclusion in the feedback data (15).

Figure 33:
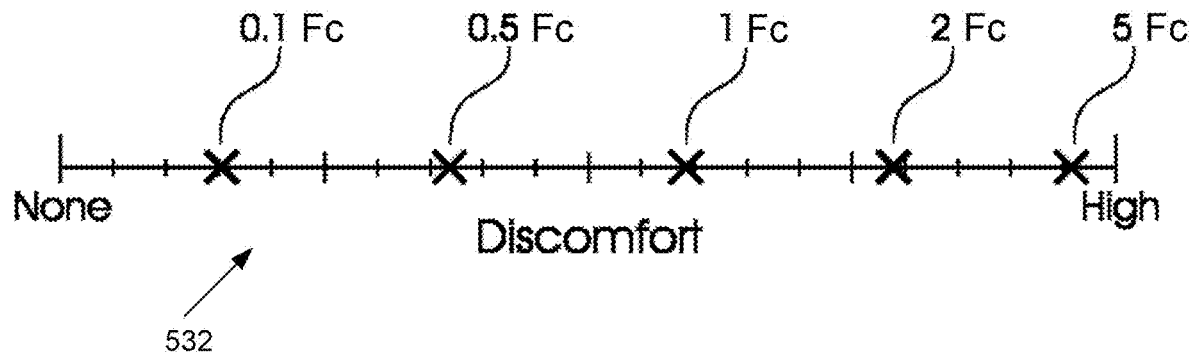
FIG. 33 shows an example embodiment for obtaining patient feedback data points using a linear scale on which the level of discomfort is indicated with relation to a target orthodontic force value.

FIG. 33, for example, shows an example embodiment for obtaining patient feedback data points using a linear scale (532) on which the level of discomfort is indicated with relation to an orthodontic force as a function of Fc (in this example illustration). This method can be used to determine an optimal orthodontic force that achieves the least level of discomfort while still resulting in orthodontic tooth movement. In this method, a force is applied to a tooth of a patient and the level of discomfort experienced by the patient is indicated on the scale. The force as a function of the critical force Fc is then indicated and correlated to the level of discomfort experienced. A similar method can be used to plot the force as a function of case specific Fc against the level of discomfort on a vertical axis. Other techniques or methods for collecting patient feedback data points may also be used.

In an embodiment incorporating patient feedback data points obtained using the linear scale (532) of FIG. 33, and for example scoring rate of treatment on a scale of 1 to 10, iteratively updating the algorithm based on the feedback data points may for example include:

| Sample | Algorithm | Patient discomfort score | Treatment feedback score |
|---|---|---|---|
| 1 | $5 * F_c$ | 19 (Very high) | 4 (slow) |
| 2 | $2 * F_c$ | 16 | 10 (rapid) |
| 3 | $1 * F_c$ | 12 | 7 |
| 4 | $0.5 * F_c$ | 7 | 5 |
| 5 | $0.1 * F_c$ | 3 (very low) | 5 (slow) |

The second sample of the algorithm may be determined as being optimized in that it balances patient feedback data points against treatment feedback data points to result in the most rapid treatment that is sufficiently comfortable from the patient's perspective. The example algorithm includes only a magnitude component (i.e. a multiplication of the target force by a fixed value). It should however be appreciated that in other embodiments, the algorithm may include other components so as to be time, stage and/or patient data dependent or the like. The process of optimizing the algorithm may be more sophisticated and may include for example time dependent functions such that the target force changes over time, may include exponential or logarithmic functions, or any other type of mathematical function that may define the target and optimal force. Of course other forms of patient feedback may be obtained, including for example feedback on questions such as "How does it feel while you chew?", "Would you recommend this appliance to a friend?", "Have you noticed any adverse effects, such as reddening of the gums, etc.?" and the like).

Returning to FIG. 32, the method includes testing (526) the appliance for treatment feedback and collecting data points for inclusion in the feedback data (15). Testing the appliance for treatment feedback may include monitoring treatment progress (e.g. rate of movement), recording treatment milestones and the like. These data points may be collected over a period of time, for example over hours, days, weeks or months. The feedback data can then be used to update the algorithm for the purpose of optimizing one or more data points of the feedback data. In other words, the algorithm may be updated to improve feedback data points against metrics such as patient comfort, rate of treatment and treatment outcome.

Collecting feedback data (15) (particularly test rig and patient feedback data points) may include collecting feedback data in real-time or near-real-time for rapid iteration and updating of the algorithm. In other words, utilizing additive manufacturing techniques to manufacture orthodontic appliances configured to apply the relevant target orthodontic force allows for test rig feedback and patient feedback to be obtained for a number of successive iterations of the algorithm within a relatively short space of time. There could for example be multiple iterations analyzed for this type of feedback data within a single day. Collection of treatment feedback data points may of course need more time as treatment has to be allowed to run its normal course.

The method may include determining (527) whether or not the feedback data is optimized. In one example the method may include collecting patient feedback data and treatment feedback data where the patient feedback data may include the level of discomfort of the appliance and the treatment feedback data may include the rate of tooth movement of one or more teeth. If the patient feedback data indicates that there was very low or no levels of discomfort experienced by the patient and the treatment feedback data indicates a slow rate of tooth movement, then this could be considered not optimized and the algorithm may be updated to increase the target force to be more optimal. In another example, if the patient feedback data indicates a high level of discomfort and the treatment feedback data indicates a slow rate of tooth movement then this may be considered not optimized and the algorithm may be updated to decrease the target force level in order to achieve a more optimal patient feedback and treatment feedback.

If (527) the feedback data is not optimized, the method includes updating (510) the algorithm, for example by adjusting weights of the one or more components or variables of the algorithm. Similarly updating the algorithm, in cases where the algorithm includes a time component, may include updating the algorithm, which is a function of time, so that the target force is lower during a certain time during the treatment, for example when the tissue is undergoing remodeling, and is higher at another time during treatment, for example at the end of treatment. The algorithm may be updated iteratively to maximize feedback metrics for improved comfort, rate of treatment and/or treatment outcome. With the algorithm updated, an updated target orthodontic force may be determined (528) using the updated algorithm and then used to reconfigure (530) the appliance (or create a new appliance) to apply the updated target orthodontic force. The method may repeat (531) to obtain updated feedback data (15) until the one or more data points of the feedback data are optimized (527).

If or once (527) the feedback data have been optimized, the algorithm may be stored (536) or otherwise labelled or identified as the optimal algorithm for use in determining a target orthodontic force that is an optimal orthodontic force based on one or more determinate points of PDL curve associated with patient data or a subset thereof.

Aspects of the present disclosure therefore provide for the determination of a target orthodontic force value that is patient, case and tooth specific and is optimized for patient comfort and/or treatment outcome. The tooth/patient/case specificity is by virtue of the target orthodontic force being a function of PDL behavior data that is associated with patient data. The optimization is by virtue of the algorithm that has been iteratively optimized based on feedback data and that operates on the PDL behavior data to output the target orthodontic force. Aspects of the present disclosure enable a shift from a spatial paradigm of the prior art systems where treatment is determined based on required movement to a force-based paradigm for orthodontic treatment where treatment is based on a relatable force applied on a determinate point of patient, case and tooth specific PDL behavior data.

Conventionally, the absolute value of orthodontic forces are compared to one-another and a single method has been used in numerous scientific studies and publications looking to establish a relationship between the applied force and, e.g., the rate of tooth movement. This approach of comparing the absolute value of the force is not able to account for any variation between the cases, the individuals, type of teeth or direction of movement. Aspects of the present disclosure, however, are able to account for such case specific parameters by defining the applied force as a function of the case specific critical force Fc (or other suitable determinate point(s)). FIG. 34 illustrates one example embodiment of comparing forces according to aspects of the present disclosure. A first step identifies (540) the absolute force magnitudes for two different cases. For example the same absolute force magnitude of F=25 gm could be applied to two different teeth (tooth A and tooth B), each having a case specific critical force level (e.g. Fca=25 gm and Fcb=12.5 gm). The next step involves expressing (542) the absolute force magnitude as a function of the critical force Fca and Fcb. If in the given example F=25 gm which is equal to the critical force Fca and thus F=f(Fc)=1*Fca. However, it is twice the magnitude of the critical force Fcb and thus can be expressed as F=f(Fc)=2*Fcb. In the third step, the force F applied to the two different cases A and B is compared (544) by comparing the force F as a function of the critical force Fc:

$F=Fa=f(Fca)=1*Fc$ $F=Fb=f(Fcb)=2*Fc$ thus $Fa/Fb=(1*Fc)/(2*Fc)=½$ $2*Fa=Fb$

Even though the absolute magnitude of the force F is the same in both cases, the effective force for case B is twice as large as that in case A. Practically, this process can be used to compare the same force applied to a molar (case A) vs for example an incisor (case B) for which the critical force level is lower. The force magnitude is the same but the effect on the PDL and surrounding tissue might be much larger (twice that) of the same force applied to the molar in case A. This example is described with reference to an example scenario in which the relevant determinate point of the PDL behavior curve is the critical force. It should be appreciated that in other cases other points or ranges of points may be used.

Model Training Engine

The model training engine (31) described above with reference to FIG. 1A may be configured to perform or conduct a method for training a model for use in determining PDL behavior data points. This may include assimilating patient- and case-specific values of a critical orthodontic force for modelling periodontal ligament behavior. One example embodiment of a method for training a model for use in determining PDL behavior data points is described below with reference to FIG. 35. The method may be conducted by a suitable computing device which in some embodiments may form a part of or may provide a model training engine.

The method includes obtaining (560) a dataset including or based on one or both of measured PDL behavior data (9A) and associated metadata (11). This may include retrieving the dataset from a datastore (7) or compiling the dataset from data retrieved from the datastore (7). For example, the dataset may include a subset or selection of measured PDL behavior data (9A) and associated metadata. Alternatively, the dataset may include all of the available measured PDL behavior data and associated metadata. In some cases, the data set includes measured PDL behavior data and modelled PDL behavior data (or subsets/selections thereof).

The measured PDL behavior data (9A) includes force measurement data points and corresponding displacement measurement data points having been measured in-vivo while applying a force to a particular tooth of a human or animal subject. The metadata is associated with the human or animal subject from whom the measurements were taken and includes data points relating to one or more of physiological, biological, genetic and situational characteristics of the human or animal subject. The measured PDL behavior data and associated metadata may be captured or obtained by a measurement system (10) or may be made available to the datastore via another suitable mechanism.

The data points of the measured PDL behavior data are associated with the human or animal subject from whom they are obtained and with the tooth in respect of which they relate (i.e. in respect of which the force is applied and of which the displacement is measured). In one example implementation, the measured PDL behavior data may include an array for each subject and each tooth, the array including force and displacement measurement datapoints and associated timestamps corresponding to the time (real-clock or otherwise) and optionally date at which the measurements were made. As mentioned in the foregoing, the data points have components for each of six degrees of freedom. For example:

```
PDL_data(subject_ID, tooth_ID):
[yyyymmddhhmmssms,Ftx,Fty,Ftz,Dtx,Dty,Dtz,Fmx,
Fmy,Fmz,Dmx,Dmy,Dmz;
...;
...]
```

Each displacement measurement data point of the measured PDL behavior data may therefore be associated with the particular tooth of a particular subject to which a particular force is applied. In the context of PDL behavior, the displacement measurement data points may be considered dependent variables while the force measurement data points may be considered independent variables. Although the term "displacement measurement data point" is used herein, it should be appreciated that this data point may in fact be a position measurement data point which together with at least one other position measurement data point results in a displacement measurement data point. The term "displacement measurement data point" should therefore be interpreted to include one or more position measurements. The dataset may therefore include measured PDL behavior data and associated metadata for each of a large number of human or animal subjects from whom or on whom the measurements are obtained in-vivo. The dataset may be a large-scale data set including datapoints for hundreds of thousands of human and/or animal subjects. PDL behavior is based on physiological attributes, so measuring data points relating to PDL behavior (such as the force/displacement measurements) implicitly records physiological attributes without invasion or complexity that would otherwise be required to understand PDL behavior.

The data points may be associated with timestamps relating to the time at which the measurements were made. The data may for example include data points measured for a longer period of time (e.g. 3 hours or even 24 hours) with all data points being part of one continuous stream. In some cases, the data points may for example be measured on a tooth on Day 0 for a duration of 3 minutes, then stop, then on Day 5 we can take the same measurement for 3 minutes, then stop, then on Day 10 measure for 3 minutes, then stop, etc. The data can be used as one time series data set or each one of those 3 min data sets can be used individually for training a model. The data points may therefore be a continuous data stream with intermittent instances of that data stream over a long period of time, or could be intermittent data. As the bone starts to remodel, the tissue may become inflamed and based on this the curve may change to account for the changes of time.

The metadata points may include scores or other indicators of physiological, biological, genetic and situational characteristics of the human or animal subject. Selected physiological data points may include any physiological parameters affecting the PDL behavior, such as data points relating to one or more of: tooth and root morphology; PDL thickness and shape; blood pressure; health related data such as oral and tissue health, time in treatment journey (if applicable) and the like. Selected situational data points may include one or more of: socioeconomic status; one or more living standards measure (LSM) inputs; an LSM output; country, state, city of residence; country, state, city of birth; diet and the like. Selected biological data points may include one or more of: age; gender; ethnicity; species and the like. The metadata is associated with the human or animal subject from which the measured PDL behavior data is obtained, for example:

Metadata(human_ID): [gender,socio_economic, . . . ,health,age,diet,country_of_birth,country_of_residence . . . ]

The metadata may therefore include information about the human/animal subject for categorization of and comparison between different types of human/animal subjects. Characteristics or parameters such as these at least to some extent affect the PDL behavior and are related to orthodontic tooth movement. By including these characteristics or parameters in the dataset, a learning model can learn the behavior of the PDL based on the included characteristics/parameters and associated measurement data.

In some embodiments, the dataset therefore includes or is based on one or both of: measured PDL behavior data including data points having been measured in-vivo while applying a force to a particular tooth of each of a plurality of human or animal subjects; and, associated metadata for each of the plurality of human or animal subjects. Further, in some embodiments, the dataset includes or is based on one or both of: measured PDL behavior data including data points having been measured in-vivo while applying a force to each of a plurality of teeth of a human or animal subject; and, the associated metadata for the human or animal subject. In other embodiments, datasets may be retrieved on a per-tooth or per-subject basis.

The dataset may be a training dataset including one or more target attributes (i.e. that which is to be predicted) which, depending on implementation, may be either one or more force measurement data points, or one or more displacement measurement data points.

Obtaining the dataset may therefore include receiving the measurement data of an applied force and the measurement data of the resulting tooth displacement, such movement can be one or any combination of six degrees of freedom. The measurement data describing the PDL behavior can include the magnitude, direction, timestamps, or other parameters describing the applied stimulus and resulting tooth movement and can include data for one individual or a group of teeth.

The method includes training (562) a model using a learning algorithm which identifies patterns in or relationships between data points of the dataset. This may include identifying a relationship between force measurement data points and displacement measurement data points for, in some implementations, different teeth and/or different characteristics of the subject. Training the model may include using the learning algorithm to identify patterns in or relationships between the measured PDL behavior data points and/or metadata data points.

As mentioned above, the dataset may include one or more input attributes and one or more target attributes and the learning algorithm may be configured to find patterns in the dataset that map the one or more input attributes to the one or more target attributes. In one example implementation, the input attributes include one or more metadata data points and the other of: one or more force measurement data points, or one or more displacement measurement data points.

The method may include performing (564) feature processing to transform one or more data points of the dataset into features and compiling (566) the features into one or more feature vectors. This may include processing the measured PDL data and/or metadata to determine features for inclusion in the one or more feature vectors. The one or more feature vectors may include features relating to one or more of: force measurement data points, displacement measurement data points and metadata data points. Examples of features may include the force direction, force duration, rate of change of force, the gradient of the force data in relation to the displacement data, hysteresis effects, or recovery rates of displacement data amongst others. Training the model using the learning algorithm may then include using the learning algorithm to identify patterns in or relationships between the features in the one or more feature vectors. Training the model may further include determining feature weights for features of a feature vector. The method may therefore include creating a feature vector of the physiological parameters or characteristics and the tooth displacement of the one or more teeth for which the PDL behavior is described.

In some implementations, training the model using the learning algorithm includes training a plurality of different models using different learning algorithms and generating different feature vectors. A tooth-to-tooth feature vector including measured PDL behavior data for different teeth may for example be generated using a linear regression, segmented linear regression or similar algorithm for identifying a relationship in PDL behavior data between teeth. A rich feature vector including metadata-based features and PDL behavior-based features may be generated using a convolutional neural network (CNN) or similar model for identifying a relationship between these features. The model, which may be a machine learning model, is therefore trained to predict the tooth movement resulting from an applied force or stimulus to the one or more teeth (or vice versa) and may include a number of feature weights.

The method includes outputting (568) the model (33) for use in determining PDL behavior data points including required force data points for a desired displacement of a tooth of a patient or resultant displacement data points for an applied force to a tooth of a patient. Outputting the model may include outputting the feature weights for features of the one or more feature vectors. The model that is output is a computer-implementable artifact that models PDL behavior for a patient based on one or more of physiological, biological, genetic and situational characteristics of the patient. Outputting the model includes saving the model and optionally feature weights for future use. The final model is suitable for outputting a prediction of the behavior of the PDL when subject to a specific force or stimulus. The model may be output for access and use by a treatment plan engine (41), an appliance configuration engine (43) and optionally a point of care system (5) or other remote computing system via the interface component (23).

Referring now to FIG. 36, an example method for using a PDL behavior model (33) is illustrated. The method may be conducted by a computing device. The method includes receiving (570) a force vector data for one or more teeth, where such data can include the force magnitude, direction, point of application and can be in six degrees of freedom. In addition, such force data can describe the forces applied for a single or a group of teeth. The force vector data is input into the PDL behavior model (33) which uses the input to compute (572) and return an estimate for the behavior of the PDL and the related tooth displacement. Such resulting tooth displacement can be case, tooth and patient specific and can be for one or more teeth. The method includes returning (574) the estimated PDL behavior data and related tooth displacement for use in a software, which can be a treatment planning software, or appliance design software or other.

Aspects of the present disclosure therefore provide a process for developing a machine learning model to describe the behavior of the PDL and a process of using a trained machine learning model to determine an estimate of the behavior of the PDL when subject to a given stimulus. Aspects of the present disclosure relate to the assimilation of patient- and case-specific values of a critical orthodontic force. Input parameters may include metadata and patient information such as age, gender, ethnicity, and other factors. The corpus of critical orthodontic values used to produce output parameters relating to orthodontic treatment, including orthodontic treatment planning, staging of tooth movement, determining the maximum rate of tooth movement, duration of treatment and a model for clear aligners or other orthodontic appliances. This may include the use of Machine Learning (ML) and Artificial Intelligence (AI) methods to determine additional case specific values of critical orthodontic forces using the corpus of critical orthodontic values as input.

Treatment Plan Engine

Aspects of the present disclosure relate to methods and systems for orthodontic staging using critical orthodontic force parameters, including for example, automating and optimizing an orthodontic treatment plan staging based on critical orthodontic force data or other PDL behavior-based determinate points. The system and method may use known critical orthodontic force data or other PDL behavior-based determinate points as input. Outputs may include maximum tooth movement rates, optimal force to be applied to one or more tooth/teeth, a duration of treatment, a number of iterations required for orthodontic aligner treatment and an optimal path of movement of one or more tooth/teeth.

The treatment plan engine (41) described above with reference to FIG. 1A may for example be configured to perform or conduct a method for orthodontic treatment staging. This may for example include automating and optimizing an orthodontic treatment plan staging based on critical orthodontic force data or other PDL behavior-based determinate points.

Figure 37B:
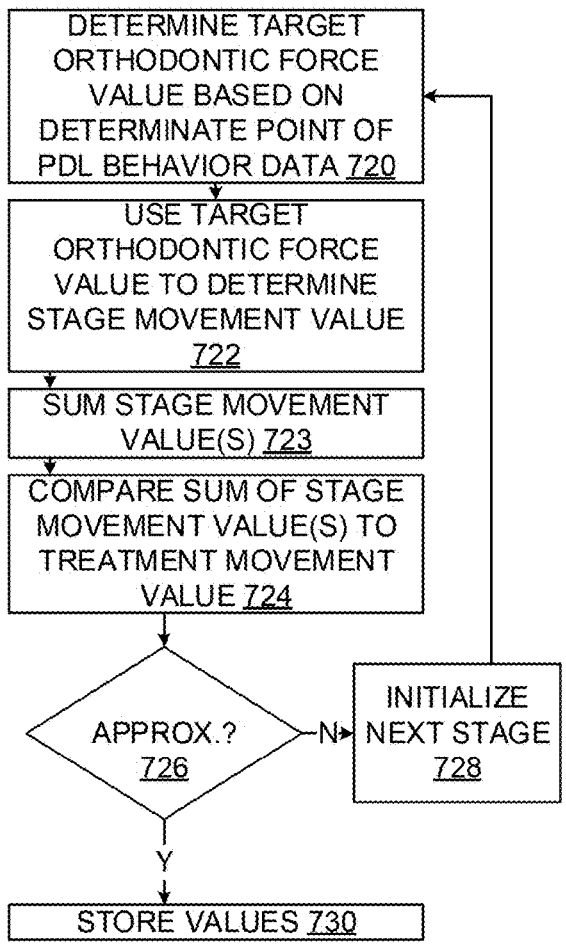
FIG. 37B is a flow diagram which illustrates a first example embodiment of a method for determining one or more stage movement values and corresponding stage force values based on a target orthodontic force value according to aspects of the present disclosure.
Figure 37A:
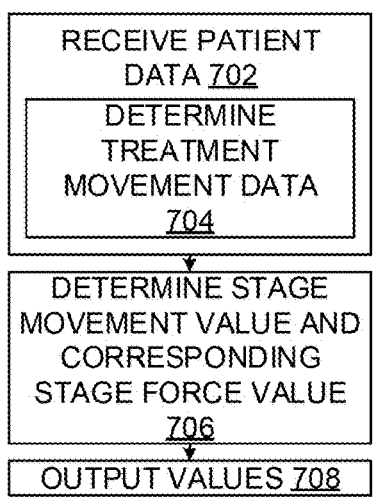
FIG. 37A is a flow diagram which illustrates one example embodiment of a method for orthodontic treatment staging according to aspects of the present disclosure.

FIG. 37A is a flow diagram which illustrates one example embodiment of a method for orthodontic treatment staging according to aspects of the present disclosure. The method may be conducted by a suitable computing device which in some embodiments may form a part of or may provide a treatment plan engine.

The method includes receiving (702) patient data (13) including patient treatment data and patient characteristic data. The patient data may be received from a point of care system (5) via a communication network (21) and/or interface component (23). The patient data may for example be input into a point of care system by a healthcare professional responsible for the treatment or correction of the patient's tooth or teeth. In other embodiments, the patient data (13) may be received from another source, such as a datastore (7) an interface component (23) or the like.

The patient characteristic data may for example include data points relating to one or more of physiological, biological, genetic and situational characteristics of the patient. The patient treatment data includes one or both of a tooth type indicator and a tooth position indicator associated with the tooth of the patient to be treated and treatment movement data which describes the required tooth movement to effect treatment or correction of the tooth. The treatment movement data includes one or more treatment movement values, each treatment movement value having components for each of six degrees of freedom.

In some embodiments, receiving patient data includes determining (704) treatment movement data for the patient. Determining treatment movement data may include determining required movement of the tooth based on the tooth's current condition or situation and its desired (or treated or corrected) condition or situation. Receiving patient treatment data may for example include receiving a tooth model with individual teeth and the planned movement of each individual tooth and using the model to determine the treatment movement value including direction and magnitude of movement of each individual tooth.

Receiving patient data thus includes receiving information about the intended movement of a specific tooth. This information may include the type of tooth and can include other patient data including the patient age, health, geographical location or ethnicity (as contained in the patient characteristic data).

Figure 37C:
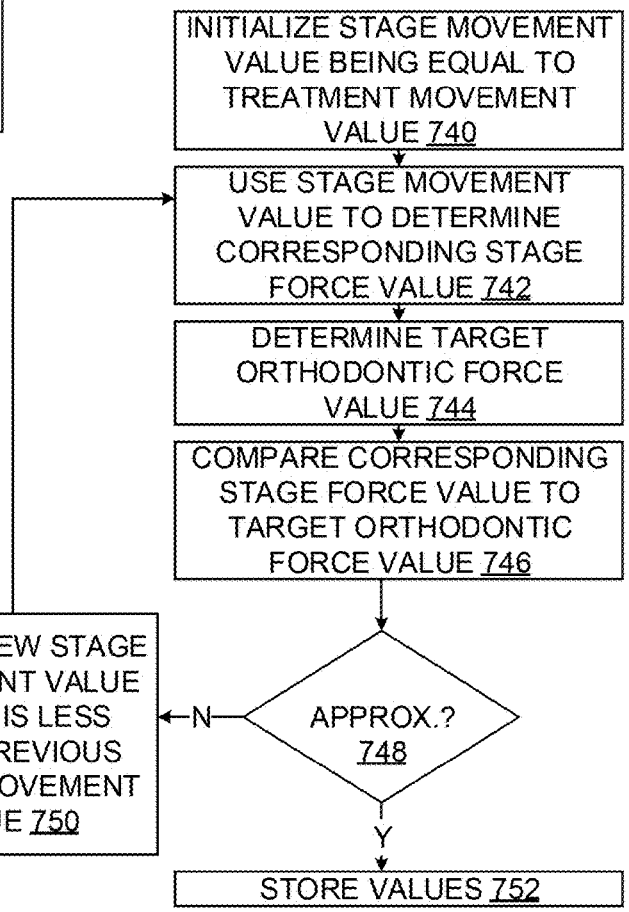
FIG. 37C is a flow diagram which illustrates a second example embodiment of a method for determining one or more stage movement values and corresponding stage force values based on a target orthodontic force value according to aspects of the present disclosure.

The method includes determining (706) one or more stage movement values and corresponding stage force values for each of one or more stages of a treatment plan. The sum of the one or more stage movement values approximates the treatment movement value such that treatment of the tooth is effected through completion of each of the stages of treatment. Each stage movement value and its corresponding stage force value is determined based on a target orthodontic force value, which is in turn based on one or more determinate points of PDL behavior data associated with at least a subset of the patient data. As mentioned in the foregoing, the PDL behavior data includes or is based on force measurement data points and corresponding displacement measurement data points having been measured in-vivo while applying a force to a particular tooth of a human or animal subject. FIGS. 37B and 37C are flow diagrams which illustrate two example embodiments for determining one or more stage movement values and corresponding stage force values based on a target orthodontic force value. As with the treatment movement value, each of the one or more stage movement values, stage force values and target orthodontic force values include components for each of six degrees of freedom. The treatment movement value, stage movement value, stage force value and target orthodontic force value may be time dependent.

The method includes outputting (708) the one or more stage movement values and corresponding stage force values as a treatment plan for treatment of the tooth. The stage movement values and stage treatment values may be output to one or more of: a point of care system (5), a datastore (7), an appliance configuration engine (43) and an interface module (23).

Referring now to FIG. 37B, in which a first example embodiment of a method for determining one or more stage movement values and corresponding stage force values based on a target orthodontic force value is illustrated.

In this example embodiment, the method includes determining (720) a target orthodontic force value based on one or more determinate points of the PDL behavior data associated with at least a subset of the patient data. In embodiments in which the PDL behavior data includes the PDL behavior model, determining the target orthodontic force value may include using the PDL behavior model to determine the one or more determinate points of the PDL behavior data and inputting the one or more determinate points into an algorithm that determines the target orthodontic force as a function of the one or more determinate points. Further inputs to the algorithm may include data points relating to one or more of time, magnitude, patient characteristic and patient treatment components of the algorithm. As mentioned in the foregoing, the algorithm may be optimized by iteratively updating the algorithm to optimize feedback data such that the target orthodontic force is an optimal orthodontic force. The feedback data may include one or more of: test rig feedback data points, patient feedback data points and treatment feedback data points. The feedback data is obtained during use or testing of an orthodontic appliance configured to apply a target orthodontic force.

The method includes using (722) the target orthodontic force value to determine a corresponding stage movement value. Determining the corresponding stage movement value may include using the PDL behavior data associated with the patient data. For example, in the case of the PDL behavior data being a PDL behavior model (33), this may include inputting the target orthodontic force value into the PDL behavior model (33) which in turn outputs movement data which corresponds to the target orthodontic force value. The movement data may be an approximation or estimation of the tooth movement that would result if the target orthodontic force were applied to the particular tooth of the particular patient.

The method includes summing (723) the stage movement values and comparing (724) the sum of the stage movement values to the treatment movement value and, if (726) sum of the stage movement values is less than the treatment movement value, the method repeats including initializing (728) a next treatment stage and determining (720, 722), for the next treatment stage, a target orthodontic force value and a corresponding stage movement value until the sum of stage movement values approximates the treatment movement value. If (726) or once the sum of the stage movement values approximates or equals the treatment movement value, the stage movement values and stage movement forces are stored (730) for output as a treatment plan for the patient.

FIG. 37C illustrates a second example embodiment of a method for determining one or more stage movement values and corresponding stage force values based on a target orthodontic force value.

The method includes initializing (740) a stage movement value being equal to the treatment movement value.

The method includes using (742) the stage movement value to determine a corresponding stage force value based on PDL behavior data associated with at least a subset of the patient data. Determining the corresponding stage force value may include using the PDL behavior data associated with the patient data. For example, in the case of the PDL behavior data being a PDL behavior model (33), this may include inputting the stage movement data into the PDL behavior model (33) which in turn outputs the corresponding stage force value. The force value may be an approximation or estimation of a force required to be applied to the tooth in order to result in or achieve movement of the particular tooth as described by the stage movement value.

The method includes determining (744) a target orthodontic force value that is based on one or more determinate points of the PDL behavior data. In embodiments in which the PDL behavior data includes the PDL behavior model, determining the target orthodontic force value may include using the PDL behavior model to determine the one or more determinate points of the PDL behavior data and inputting the one or more determinate points into an algorithm that determines the target orthodontic force as a function of the one or more determinate points. Further inputs to the algorithm may include data points relating to one or more of time, magnitude, patient characteristic and patient treatment components of the algorithm.

As mentioned in the foregoing, the algorithm may be optimized by iteratively updating the algorithm to optimize feedback data such that the target orthodontic force is an optimal orthodontic force. The feedback data may include one or more of: test rig feedback data points, patient feedback data points and treatment feedback data points. The feedback data is obtained during use or testing of an orthodontic appliance configured to apply a target orthodontic force.

The method includes comparing (746) the corresponding stage force value to the target orthodontic force value.

If (748) the corresponding stage force value exceeds the target orthodontic force value, the method includes defining (750) a new stage movement value which is less than the previous stage movement value and determining (742) a new corresponding stage force value based on the PDL behavior data for comparison (746) against the target orthodontic force value. The method will therefore repeat with successive new stage movement values until the corresponding stage force value approximates the target orthodontic force value. This may include re-determining the target orthodontic force value each time a new stage movement value is defined.

If or once (748) the stage force value approximates the target orthodontic force value, the method includes storing (752) the stage movement value and corresponding stage force value that approximates the target orthodontic force value for use in a treatment plan. The method may further include determining a number of required treatment stages by dividing the treatment movement value by the stage movement value so as to determine the number of stages required to effect treatment of the tooth by applying the target orthodontic force value for each stage.

The methods described above with reference to FIGS. 37A and 37B or 37C may be conducted for each tooth to be treated such that a case-, tooth- and patient-specific stage movement value and corresponding stage force value are determined for each tooth to be treated.

Figure 38:
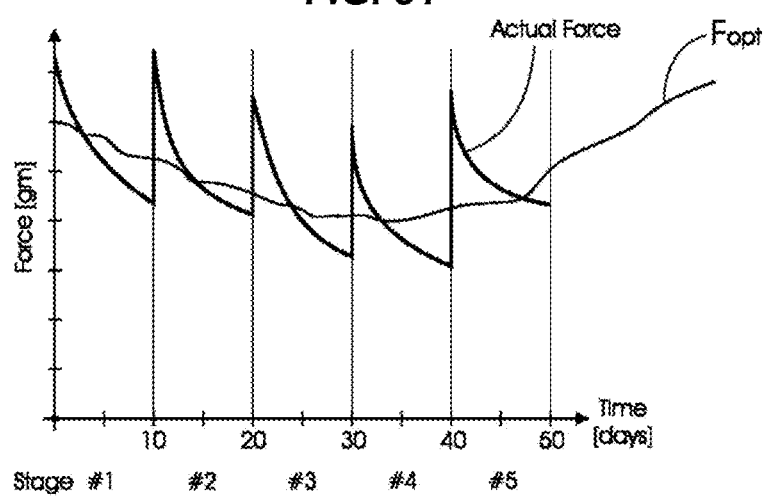
FIG. 38 is a chart which illustrates plots of a stage force value and associated target orthodontic force value over time for a plurality of stages of orthodontic treatment according to aspects of the present disclosure.

The methods described above provide for orthodontic staging using a target orthodontic force that is determined based on PDL behavior data that is case-, tooth- and patient-specific. FIG. 38 is a chart which illustrates example plots of a stage force value and associated target orthodontic force value over time for a plurality of stages of orthodontic treatment according to aspects of the present disclosure.

Appliance Configuration Engine

Aspects of the present disclosure relate to methods and systems for determining orthodontic appliance models using critical orthodontic force data as input. Outputs of the method include a material specification, size, shape, thickness, direction and geometry of features (e.g. ridges, cuts, ribs, bumps, springs, hatching, voids and spaces) on an orthodontic appliance. The output data of the model may be utilized for 3D printing of an orthodontic appliance or for instructing a robot to form or shape an orthodontic appliance or parts thereof, such as an arch wire. Aspects of the present disclosure relate to systems and methods used for designing an orthodontic appliance, the parameters, material properties and geometry of said appliance being optimized so as to apply a stimulus that represents an optimal force to one or more teeth, based at least to some extent on the behavior of the periodontal ligament.

The appliance configuration engine (43) described above with reference to FIG. 1A may for example be configured to perform or conduct a method for orthodontic appliance configuration. This may for example include conducting a method for designing an orthodontic appliance including conducting a method for preparing a specification for, designing, and producing an orthodontic clear aligner using critical orthodontic force parameters or comparable PDL behavior-based data points.

FIG. 39 is a flow diagram which illustrates one example embodiment of a method for orthodontic appliance configuration according to aspects of the present disclosure. The method may be conducted by a suitable computing device which in some embodiments may form a part of or may provide an appliance configuration engine.

The method may include receiving (590) patient data (13) including patient treatment data and patient characteristic data. The patient data may be received from a point of care system (5) via a communication network (21) and/or interface component (23). The patient data may for example be input into a point of care system by a healthcare professional responsible for the treatment or correction of the patient's tooth or teeth. In other embodiments, the patient data (13) may be received from another source, such as a datastore (7) an interface component (23) or the like.

The patient characteristic data may for example include data points relating to one or more of physiological, biological, genetic and situational characteristics of the patient. The patient treatment data includes one or both of a tooth type indicator and a tooth position indicator associated with the tooth of the patient to be treated and treatment movement data which describes the required tooth movement to effect treatment or correction of the tooth.

In some embodiments, receiving patient data includes determining (592) treatment movement data for the patient. This may for example include using a treatment plan engine (41) which determines the treatment movement data for one or more stages of treatment. Determining treatment movement data may include determining required movement of the tooth based on the tooth's current condition or situation and its desired (or treated or corrected) condition or situation. Receiving patient treatment data may for example include receiving a tooth model with individual teeth and the planned movement of each individual tooth and using the model to determine the treatment movement value including direction and magnitude of movement of each individual tooth.

Receiving patient data thus includes receiving information about the intended movement of a specific tooth. This information may include the type of tooth and can include other patient data including the patient age, health, geographical location or ethnicity (as contained in the patient characteristic data). The movement of one or more teeth can be specified by a treatment plan, which can either be described by an initial and a final position or can be described by one or more steps describing the transformation of each tooth object in space and in six degrees of freedom.

The method may include obtaining (593) a force value. In some embodiments, this may include obtaining a force value, for example a stage force value, from the treatment plan engine, the datastore, an interface module or the like. The stage force value approximates a target orthodontic force value having been determined based on patient data and PDL behavior data associated with the patient data, the patient data including patient treatment data and patient characteristic data, the patient treatment data at least including one or both of a tooth type indicator and a tooth position indicator associated with a tooth of a patient to be treated and a treatment movement value which describes the required tooth movement to effect treatment of the tooth.

In other embodiments, the obtaining the force value includes determining the force value using the patient data including patient treatment data and patient characteristic data. This may include determining (594) a target orthodontic force value based on at least a subset of the patient data (e.g. using the optimal force engine). For example, determining the target force value may include using a PDL behavior model to determine one or more determinate points of PDL behavior data associated with the patient data and inputting the one or more determinate points into an algorithm that determines the target orthodontic force as a function of the one or more determinate points.

Determining the target orthodontic force may therefore include defining an optimal force relative to the estimated PDL behavior curve. As has been explained in the foregoing, this can be done by identifying a determinate point on the curve, for example at which the PDL is estimated to reach a specific compression and defining such a point as a critical force level Fc. A case and tooth specific force can then be defined as a function of the critical force Fc. In addition, such a force can be a function of time and thus can vary over the duration of orthodontic treatment and can be different for each orthodontic appliance used throughout the duration of treatment.

The force value may therefore be the target orthodontic force value or the stage force value received from the treatment planning engine. The method includes using (596) the force value to determine configuration parameters for configuring an orthodontic appliance to apply the target orthodontic force value or stage force value, as the case may be (i.e., applying a force having magnitude and direction as represented by or corresponding to the relevant force value).

The configuration parameters may for example include specification for one or more of: stiffness, size, shape and material properties of individual portions or zones of an orthodontic appliance. In some embodiments, determining configuration parameters includes determining the geometry and material properties of the appliance so as to apply the target orthodontic force. In the case of an orthodontic appliance in the form of an aligner, for example, the configuration parameters may specify:

- the thickness of the appliance at specific zones through specification of size and shape parameters;
- the inclusion and configuration of features such as surface or sub-surface features of the appliance (e.g. ridges, cuts, ribs, bumps, springs, hatching, voids, spaces the like); and,
- the materials and their associated properties (e.g. rigid plastic materials, flexible plastic materials a combination of rigid and flexible plastics materials, etc.).

Referring briefly to FIG. 40, a cross-section through two example orthodontic appliances is illustrated, in which a first appliance (602) shown in FIG. 40(a) has a first shape through the section and a second appliance (604) shown in FIG. 40(b) has a second shape through the section. In the example embodiments illustrated, the first appliance has a constant thickness throughout the section, while the second appliance has different thicknesses at different portions or zones of the appliance. The second appliance for example has a thickened portion or zone (606) which is specifically shaped and dimensioned through the configuration parameters to apply the target orthodontic force value or stage force value, as the case may be, relevant to that tooth (608). The thickened portion or zone may have the effect of applying a greater force along the x-axis (610) compared for example to that force that would be applied along the x-axis by the appliance illustrated in FIG. 40(a). The thickened portion is provided in the lingual part of the appliance to increase the stiffness and act as a structural feature of the appliance. Similarly, there is a thicker section (607) near the incisal edge of the tooth to provide a greater stiffness and force that is applied to the tooth. The figure also shows a thinner section of the appliance toward the facial side of the tooth, which can provide a softer or more flexible function due to this part of the appliance having a lower stiffness.

Although not illustrated, an appliance can also be configured through configuration parameters to have different features in different locations of the appliance such as ridges, cuts, ribs, bumps, springs, hatching, voids, spaces thicker or thinner selections, extrusions, folds, or any other type of geometric variation. Such variations directly affect the performance and more specifically the stiffness of the appliance at the location at which they are placed. By controlling the geometry of the features and the geometry the stiffness of the appliance can be controlled and thereby the forces applied to the teeth.

In the case of an orthodontic appliance in the form of dental braces (650), for example as illustrated in FIG. 41, configuration parameters may include stiffness of wires (652, 654), which may in turn be configured through material properties, wire thickness and the like. The properties of the wire may change along its length such that different forces are applied to different teeth so as to apply a case, patient and tooth specific force to each tooth for optimal treatment. for example, the wire may have a first thickness for a first portion (658) thereof, a second thickness for a second portion (660) thereof and so on so as to apply a case, patient and tooth specific force to each tooth for optimal treatment. Configuration parameters may also include specification of an elastic band (656) (e.g. location, flexibility, thickness, etc.). Further configuration parameters may include the shape of the wire and more specifically bending of the wire along the arch as well as twisting of the wire to create torsion. These configuration parameters may be implemented by a robotic arch wire bending robot to shape the arch wire.

Returning to FIG. 39, the method includes outputting (598) the configuration parameters. The configuration parameters may be output to one or more of: a treatment plan engine (41); a point of care system (5); an interface module (23); and, a datastore (7). The method may be conducted or repeated for each tooth to be treated such that a tooth- and patient-specific configuration parameters are determined for each tooth to be treated. Outputting the configuration parameters may include outputting the configuration parameters for each tooth of the patient to be treated or corrected to an additive manufacturing machine to manufacture an orthodontic appliance configured to apply the target orthodontic force value or stage force value, as the case may be, to the teeth. For example, in some embodiments, outputting the configuration parameters includes outputting a 3D mesh or point cloud file (such as a stereolithography (STL) file) embodying the configuration parameters such that the file can be input into the additive manufacturing (or 3D printing) machine to manufacture an orthodontic appliance configured to apply the relevant target orthodontic force valued or stage force valued, as the case may be. As mentioned, each force value has a component for each of six degrees of freedom such that the different portions or zones of the orthodontic appliance will be shaped/configured differently to apply different forces in different directions/rotations.

Figure 42:
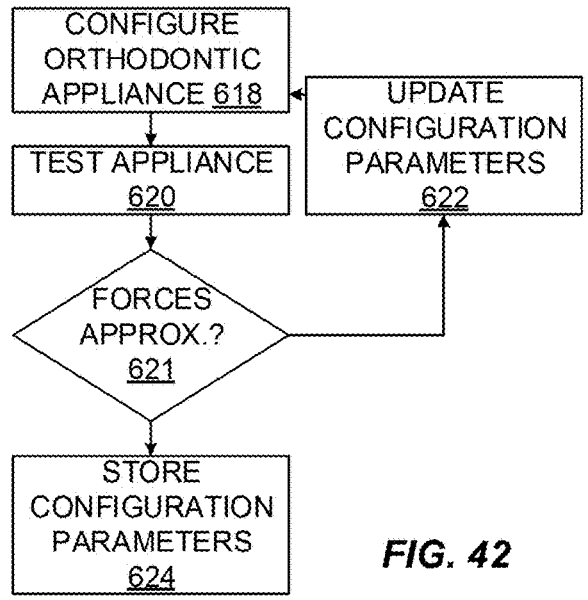
FIG. 42 is a flow diagram which illustrates an example method for evaluating configuration parameters according to aspects of the present disclosure.

In some embodiments, and referring now to FIG. 42, the method includes evaluating the output configuration parameters, including configuring (618) an orthodontic appliance in accordance with the configuration parameters (e.g. including setting an appliance geometry based on the configuration parameters), testing (620) the appliance to evaluate the difference between an actual orthodontic force applied by the appliance and the target orthodontic force value or stage force value, as the case may be (or target stiffness versus actual stiffness) and, if (621) the applied orthodontic force does not approximate the target orthodontic force value or stage force value, as the case may be, the method includes updating (622) the configuration parameters based on this difference. The evaluation may repeat until the applied orthodontic force approximates the target orthodontic force at which point the configuration parameters may be stored (624) as the final configuration parameters.

Aspects of the present disclosure therefore enable control of configuration parameters of an orthodontic appliance based on an optimal or target orthodontic force value. This allows for orthodontic treatment or correction based on an optimal orthodontic force that is determined based on PDL behavior data expected for that specific tooth of the specific patient. As mentioned in the foregoing, the PDL behavior data describes the force vs displacement relationship of the PDL. Aspects of the present disclosure may therefore improve appliance configuration technology b determining target orthodontic forces based on PDL data points that are patient, case and tooth specific. Aspects of the present disclosure enable the determination of orthodontic appliance configuration parameters using PDL behavior data which includes or is based on measurement data obtained from a large number of human or animal subjects in-vivo.

The appliance configuration engine (43) may therefore conduct a method for orthodontic appliance configuration including: receiving the direction and amount of movement of one or more teeth; determining the PDL behavior for that specific direction in three dimensional space; using a machine learning model that has been trained to provide an estimate of the force vs displacement relationship of the PDL, the behavior being based at least to some extent on the PDL behavior measured in-vivo; with reference to the PDL behavior in the given direction, determining a target or optimal orthodontic force; based on the determined target or optimal force, in the given direction, defining the desired appliance function; and, based on the desired appliance function, determining the size, shape and material properties of the orthodontic appliance.

Orthodontic Treatment System

Figure 43:
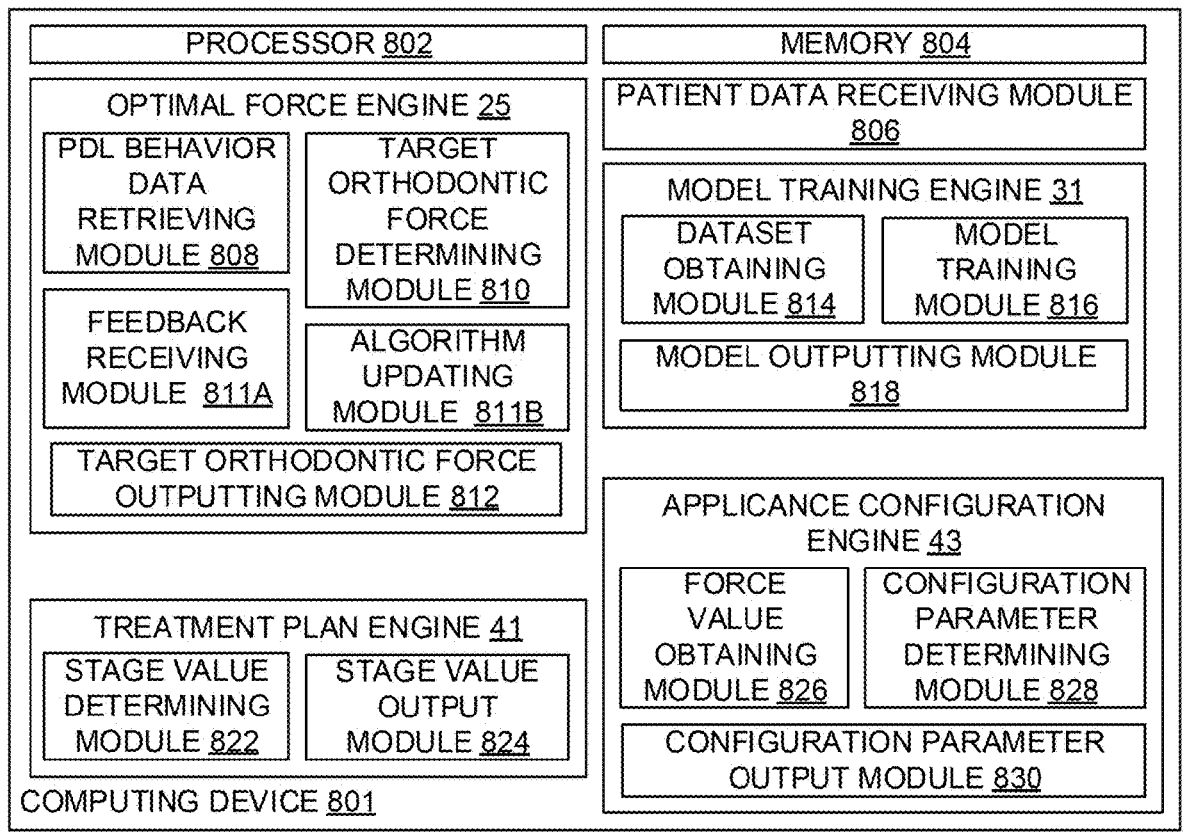
FIG. 43 is a block diagram which illustrates exemplary components which may be provided by an orthodontic treatment system according to aspects of the present disclosure.

Various modules may be provided for implementing the methods described above. FIG. 43 is a block diagram which illustrates exemplary modules which may be provided by an orthodontic treatment system (1) which may include a computing device (801).

The computing device (801) may include a processor (802) for executing the functions of modules described below, which may be provided by hardware or by software units executing on the computing device (801). The software units may be stored in a memory (804) and instructions may be provided to the processor (802) to carry out the functionality of the described modules. In some cases, for example in a cloud computing implementation, software units arranged to manage and/or process data on behalf of the computing device (801) may be provided remotely.

The system (1) may include a patient data receiving module (806) for receiving patient data associated with a patient. The patient data includes patient characteristic data and patient treatment data, the patient treatment data at least including one or both of a tooth type indicator and a tooth position indicator associated with a tooth of the patient to be corrected.

The system (1) may include a PDL behavior data retrieving module (808) for retrieving PDL behavior data associated with at least a subset of the patient data. As mentioned, the PDL behavior data includes or is based on force measurement data points and corresponding displacement measurement data points having been measured in-vivo while applying a force to a tooth of a human or animal subject.

The system (1) may include a target orthodontic force determining module (810) for determining a target orthodontic force value that is specific to the patient data by inputting the PDL behavior data into an algorithm which determines the target orthodontic force based on the PDL behavior data.

The system (1) may include a feedback receiving module (811A) for receiving feedback data obtained during use of an orthodontic appliance configured to apply a target orthodontic force to a tooth of a patient. The system (1) may include an algorithm updating module (811B) for updating the algorithm using the feedback data. The target orthodontic force determining module (810) may further be for using the updated algorithm to determine an updated value corresponding to an updated target orthodontic force for use in reconfiguring or replacing the orthodontic appliance so as to apply the updated target orthodontic force.

The system (1) may include a target orthodontic force outputting module (812) for outputting the target orthodontic force value.

The system (1) may include a dataset obtaining module (814) for obtaining a dataset including or based on one or both of measured PDL behavior data and associated metadata. The measured PDL behavior data includes force measurement data points and corresponding displacement measurement data points having been measured in-vivo while applying a force to a particular tooth of a human or animal subject. The metadata relating to the human or animal subject and including data points relating to one or more of physiological, biological and genetic characteristics of the human or animal subject.

The system (1) may include a model training module (816) for training a model using a learning algorithm which identifies patterns in or relationships between data points of the dataset. Training the module may include identifying a relationship between force measurement data points and displacement measurement data points.

The system (1) may include a model outputting module (818) for outputting the model for use in determining PDL behavior data points including required force data points for a desired displacement of a tooth of a patient or resultant displacement data points for an applied force to a tooth of a patient.

The PDL behavior curves illustrated in the accompanying Figures show example measurements for a single tooth of a single human/animal subject and for one of six possible degrees of freedom. It should be appreciated that for each human/animal subject, there may be obtained one PDL behavior curve for each tooth of the patient and for each of the six possible degrees of freedom.

The system (1) may include a stage value determining module (822) for determining one or more stage movement values and corresponding stage force values. Each stage force value is based on a target orthodontic force value that is based on one or more determinate points of PDL behavior data associated with at least a subset of the patient data. The sum of the one or more stage movement values approximates the treatment movement value received with the patient data.

The system (1) may include a stage value output module (824) for outputting the one or more stage movement values and corresponding stage force values as a treatment plan for treatment of the tooth.

The system (1) may include a force value obtaining module (826) for obtaining a force value which approximates a target orthodontic force value having been determined based on patient data and PDL behavior data associated with the patient data.

The system (1) may include a configuration parameter determining module (828) for using the force value to determine configuration parameters for configuring an orthodontic appliance to apply the force value (i.e., applying a force having magnitude and direction as represented by or corresponding to the force value) to the tooth of the patient.

The system (1) may include a configuration parameter output module (830) for outputting the configuration parameters.

Figure 44:
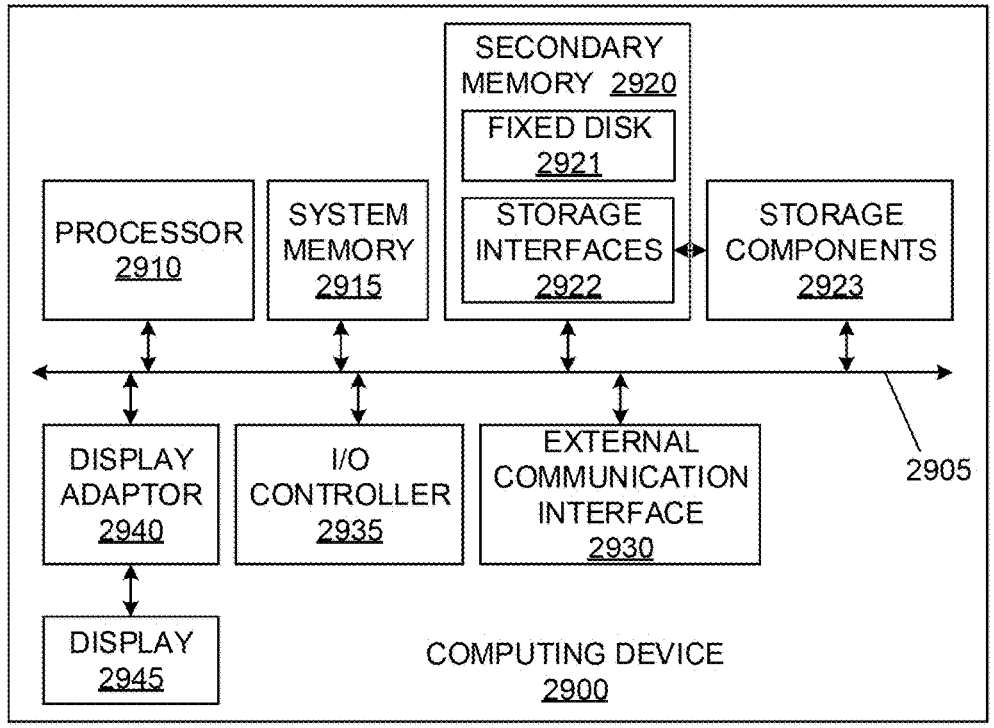
FIG. 44 illustrates an example of a computing device in which various aspects of the disclosure may be implemented.

FIG. 44 illustrates an example of a computing device (2900) in which various aspects of the disclosure may be implemented. The computing device (2900) may be embodied as any form of data processing device including a personal computing device (e.g. laptop or desktop computer), a server computer (which may be self-contained, physically distributed over a number of locations), a client computer, or a communication device, such as a mobile phone (e.g. cellular telephone), satellite phone, tablet computer, personal digital assistant or the like. Different embodiments of the computing device may dictate the inclusion or exclusion of various modules or subsystems described below.

The computing device (2900) may be suitable for storing and executing computer program code. The various participants and elements in the previously described system diagrams may use any suitable number of subsystems or modules of the computing device (2900) to facilitate the functions described herein. The computing device (2900) may include subsystems or modules interconnected via a communication infrastructure (2905) (for example, a communications bus, a network, etc.). The computing device (2900) may include one or more processors (2910) and at least one memory module in the form of computer-readable media. The one or more processors (2910) may include one or more of: CPUs, graphical processing units (GPUs), microprocessors, field programmable gate arrays (FPGAs), application specific integrated circuits (ASICs) and the like. In some configurations, a number of processors may be provided and may be arranged to carry out calculations simultaneously. In some implementations various subsystems or modules of the computing device (2900) may be distributed over a number of physical locations (e.g. in a distributed, cluster or cloud-based computing configuration) and appropriate software units may be arranged to manage and/or process data on behalf of remote devices.

The memory modules may include system memory (2915), which may include read only memory (ROM) and random access memory (RAM). A basic input/output system (BIOS) may be stored in ROM. System software may be stored in the system memory (2915) including operating system software. The memory modules may also include secondary memory (2920). The secondary memory (2920) may include a fixed disk (2921), such as a hard disk drive, and, optionally, one or more storage interfaces (2922) for interfacing with storage modules (2923), such as removable storage modules (e.g. magnetic tape, optical disk, flash memory drive, external hard drive, removable memory chip, etc.), network attached storage modules (e.g. NAS drives), remote storage modules (e.g. cloud-based storage) or the like.

The computing device (2900) may include an external communications interface (2930) for operation of the computing device (2900) in a networked environment enabling transfer of data between multiple computing devices (2900) and/or the Internet. Data transferred via the external communications interface (2930) may be in the form of signals, which may be electronic, electromagnetic, optical, radio, or other types of signal. The external communications interface (2930) may enable communication of data between the computing device (2900) and other computing devices including servers and external storage facilities. Web services may be accessible by and/or from the computing device (2900) via the communications interface (2930).

The external communications interface (2930) may be configured for connection to wireless communication channels (e.g., a cellular telephone network, wireless local area network (e.g. using Wi-Fi™), satellite-phone network, Satellite Internet Network, etc.) and may include an associated wireless transfer element, such as an antenna and associated circuitry.

The computer-readable media in the form of the various memory modules may provide storage of computer-executable instructions, data structures, program modules, software units and other data. A computer program product may be provided by a computer-readable medium having stored computer-readable program code executable by the central processor (2910). A computer program product may be provided by a non-transient or non-transitory computer-readable medium, or may be provided via a signal or other transient or transitory means via the communications interface (2930).

Interconnection via the communication infrastructure (2905) allows the one or more processors (2910) to communicate with each subsystem or module and to control the execution of instructions from the memory modules, as well as the exchange of information between subsystems or modules. Peripherals (such as printers, scanners, cameras, or the like) and input/output (I/O) devices (such as a mouse, touchpad, keyboard, microphone, touch-sensitive display, input buttons, speakers and the like) may couple to or be integrally formed with the computing device (2900) either directly or via an I/O controller (2935). One or more displays (2945) (which may be touch-sensitive displays) may be coupled to or integrally formed with the computing device (2900) via a display or video adapter (2940).

The foregoing description has been presented for the purpose of illustration; it is not intended to be exhaustive or to limit the invention to the precise forms disclosed. Persons skilled in the relevant art can appreciate that many modifications and variations are possible in light of the above disclosure.

Any of the steps, operations, modules or processes described herein may be performed or implemented with one or more hardware or software units, alone or in combination with other devices. In one embodiment, a software unit is implemented with a computer program product comprising a non-transient or non-transitory computer-readable medium containing computer program code, which can be executed by a processor for performing any or all of the steps, operations, or processes described. Software units or functions described in this application may be implemented as computer program code using any suitable computer language such as, for example, Python, Java™, C++, or Perl™ using, for example, conventional or object-oriented techniques. The computer program code may be stored as a series of instructions, or commands on a non-transitory computer-readable medium, such as a random access memory (RAM), a read-only memory (ROM), a magnetic medium such as a hard-drive, or an optical medium such as a CD-ROM. Any such computer-readable medium may also reside on or within a single computational apparatus, and may be present on or within different computational apparatuses within a system or network.

Flowchart illustrations and block diagrams of methods, systems, and computer program products according to embodiments are used herein. Each block of the flowchart illustrations and/or block diagrams, and combinations of blocks in the flowchart illustrations and/or block diagrams, may provide functions which may be implemented by computer readable program instructions. In some alternative implementations, the functions identified by the blocks may take place in a different order to that shown in the flowchart illustrations.

Some portions of this description describe the embodiments of the invention in terms of algorithms and symbolic representations of operations on information. These algorithmic descriptions and representations, such as accompanying flow diagrams, are commonly used by those skilled in the data processing arts to convey the substance of their work effectively to others skilled in the art. These operations, while described functionally, computationally, or logically, are understood to be implemented by computer programs or equivalent electrical circuits, microcode, or the like. The described operations may be embodied in software, firmware, hardware, or any combinations thereof.

The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention set forth in any accompanying claims.

Finally, throughout the specification and any accompanying claims, unless the context requires otherwise, the word 'comprise' or variations such as 'comprises' or 'comprising' will be understood to imply the inclusion of a stated integer or group of integers but not the exclusion of any other integer or group of integers.

REFERENCES

1. Ren Y, Maltha J C, Van't Hof M, Kuijpers-Jagtman A M. Optimum force magnitude for orthodontic tooth movement: a mathematic model. Am. J. Orthod. Dentofac. Orthop. 2004; 125:71-7.
2. Quinn R S, Yoshikawa D K. A reassessment of force magnitude in orthodontics. Am. J. Orthod. 1985; 88:252-60.
3. Bosshardt D D, Bergomi M, Vaglio G, Wiskott A. Regional structural characteristics of bovine periodontal ligament samples and their suitability for biomechanical tests. J. Anat. 2008; 212:319-29.
4. Cattaneo P M, Dalstra M, Melsen B. The finite element method: a tool to study orthodontic tooth movement. J. Dent. Res. 2005; 84:428-33.
5. Iwasaki L R, Haack J E, Nickel J C, Morton J. Human tooth movement in response to continuous stress of low magnitude. Am. J. Orthod. Dentofac. Orthop. 2000; 117:175-83.
6. Owman-Moll P, Kurol J, Lundgren D. Effects of a doubled orthodontic force magnitude on tooth movement and root resorptions. An inter-individual study in adolescents. Eur. J. Orthod. 1996; 18:141-50.
7. Ren Y, Maltha J C, Kuijpers-Jagtman A M. Optimum force magnitude for orthodontic tooth movement: a systematic literature review. Angle Orthod. 2003; 73:86-92.
8. van Leeuwen E J, Maltha J C, Kuijpers-Jagtman A M. Tooth movement with light continuous and discontinuous forces in beagle dogs. Eur. J. Oral Sci. 1999; 107:468-74.
9. Castellini P, Scalise L, Tomasini E P. Teeth mobility measurement: a laser vibrometry approach. J. Clin. Laser Med. Surg. 1998; 16:269-72.
10. Yoshida N, Koga Y, Kobayashi K, Yamada Y, Yoneda T. A new method for qualitative and quantitative evaluation of tooth displacement under the application of orthodontic forces using magnetic sensors. Med. Eng. Phys. 2000; 22:293-300.
11. Ziegler A, Keilig L, Kawarizadeh A, Jager A, Bourauel C. Numerical simulation of the biomechanical behaviour of multi-rooted teeth. Eur. J. Orthod. 2005; 27:333-9.
12. Sanctuary C S, Wiskott H W A, Justiz J, Botsis J, Belser U C. In vitro time-dependent response of periodontal ligament to mechanical loading. J. Appl. Physiol. 2005; 99:2369-78.
13. Papadopoulou K, Keilig L, Eliades T, Krause R, Jager A, Bourauel C. The time-dependent biomechanical behaviour of the periodontal ligament—An in vitro experimental study in minipig mandibular two-rooted premolars. Eur. J. Orthod. 2014; 36:9-15.
14. Jing Y, Han X L, Cheng B H, Bai D. Three-dimensional FEM analysis of stress distribution in dynamic maxillary canine movement. Chinese Sci. Bull. 2013; 58:2454-9.
15. Papadopoulou K, Hasan I, Keilig L, et al. Biomechanical time dependency of the periodontal ligament: A combined experimental and numerical approach. Eur. J. Orthod. 2013; 35:811-8.
16. Minch L. Material properties of periodontal ligaments. Postepy Hig. Med. Dosw. 2013; 67:1261-4.
17. Wakabayashi N, Ona M, Suzuki T, Igarashi Y. Nonlinear finite element analyses: advances and challenges in dental applications. J. Dent. 2008; 36:463-71.
18. Malemann H R. Tooth mobility: a review of clinical aspects and research findings. J. Periodontol. 1967; 38: Suppl:686-713.
19. Von Bohl M, Maltha J C, Von Den Hoff H, Kuijpers-Jagtman A M. Changes in the periodontal ligament after experimental tooth movement using high and low continuous forces in beagle dogs. Angle Orthod. 2004; 74:16-25.
20. Natali A N, Pavan P G, Scarpa C. Numerical analysis of tooth mobility: Formulation of a non-linear constitutive law for the periodontal ligament. Dent. Mater. 2004; 20:623-9.
21. Melsen B, Cattaneo P M, Dalstra M, Kraft D C. The Importance of Force Levels in Relation to Tooth Movement. Semin. Orthod. 2007; 13:220-33.
22. Kojima Y, Fukui H. Numerical simulations of canine retraction with T-loop springs based on the updated moment-to-force ratio. Eur. J. Orthod. 2012; 34:10-8.
23. Cattaneo P M, Dalstra M, Melsen B. Moment-to-force ratio, center of rotation, and force level: a finite element study predicting their interdependency for simulated orthodontic loading regimens. Am. J. Orthod. Dentofacial Orthop. 2008; 133:681-9.
24. Kawarizadeh A, Bourauel C, Jager A. Experimental and numerical determination of initial tooth mobility and material properties of the periodontal ligament in rat molar specimens. Eur. J. Orthod. 2003; 25:569-78.

The invention claimed is:

1. A method comprising:
obtaining a treatment plan for treatment of a tooth of a patient, the treatment plan including two or more stage force values, wherein each of the two or more stage force values is based on a target orthodontic force value that is based on one or more determinate points of periodontal ligament (PDL) behavior data;
for each of the two or more stage force values:
determining configuration parameters for configuring an orthodontic appliance to apply the stage force value to a tooth of the patient; and,
using the configuration parameters to manufacture an orthodontic appliance configured to apply the stage force value.

2. The method as claimed in claim 1, wherein each of the two or more stage force values is different.

3. The method as claimed in claim 1, wherein the target orthodontic force value takes into account time-dependent changes in the one or more determinate points.

4. The method as claimed in claim 1, wherein the one or more determinate points change throughout a duration of orthodontic tooth movement.

5. The method as claimed in claim 1, wherein the target orthodontic force value is specific to the patient, tooth and a stage of treatment regimen.

6. The method as claimed in claim 1, including determining the target orthodontic force value by inputting the one or more determinate points into an algorithm that determines the target orthodontic force value as a function of the one or more determinate points.

7. The method as claimed in claim 6, wherein the PDL behavior data includes a PDL behavior model, and wherein determining the target orthodontic force value includes using the PDL behavior model to determine one or more determinate points of the PDL behavior data.

8. The method as claimed in claim 7, wherein the PDL behavior model is trained using measured PDL behavior data.

9. The method as claimed in claim 6, wherein further inputs to the algorithm include data points relating to one or more of time, magnitude, patient characteristic and patient treatment components.

10. The method as claimed in claim 6, wherein the algorithm is optimized by iteratively updating the algorithm to optimize feedback data such that the target orthodontic force value is an optimal orthodontic force.

11. The method as claimed in claim 10, wherein the feedback data is obtained during use or testing of an orthodontic appliance configured to apply a target orthodontic force.

12. The method as claimed in claim 10, wherein the feedback data includes one or more of: patient feedback data points and treatment feedback data points.

13. The method as claimed in claim 1, wherein the PDL behavior data is associated with patient data including data points relating to time in treatment journey.

14. The method as claimed in claim 1, wherein the PDL behavior data includes or is based on force measurement data points and corresponding displacement measurement data points having been measured in-vivo while applying a force to a particular tooth of a human or animal subject.

15. An orthodontic appliance manufactured by the method as claimed in claim 1.

16. A set of orthodontic appliances manufactured by the method as claimed in claim 1, wherein each orthodontic appliance in the set of orthodontic appliances is configured to apply a different stage force value.

* * * * *